(12) United States Patent
Upadhayaya et al.

(10) Patent No.: US 11,279,703 B2
(45) Date of Patent: Mar. 22, 2022

(54) FUSED PYRIMIDINE COMPOUNDS AS BRD4 AND JAK2 DUAL INHIBITORS AND METHODS FOR USE THEREOF

(71) Applicant: APTOSE BIOSCIENCES INC., Mississauga (CA)

(72) Inventors: Ram Shankar Upadhayaya, Journalist Colony (IN); Raghava Kethiri, Bangalore (IN); Sachin Madan, Haryana (IN); Santosh Kumar Kotturi Rajaiah, Secunderabad (IN)

(73) Assignee: APTOSE BIOSCIENCES INC., Mississauga (CA)

( * ) Notice: Subject to any disclaimer, the term of this patent is extended or adjusted under 35 U.S.C. 154(b) by 14 days.

(21) Appl. No.: 16/465,880

(22) PCT Filed: Dec. 1, 2017

(86) PCT No.: PCT/CA2017/000258
§ 371 (c)(1),
(2) Date: May 31, 2019

(87) PCT Pub. No.: WO2018/098561
PCT Pub. Date: Jun. 7, 2018

(65) Prior Publication Data
US 2020/0095252 A1 Mar. 26, 2020

Related U.S. Application Data

(60) Provisional application No. 62/428,756, filed on Dec. 1, 2016.

(51) Int. Cl.
| | | |
|---|---|---|
| *C07D 487/04* | (2006.01) |
| *A61P 35/02* | (2006.01) |
| *C07D 401/12* | (2006.01) |
| *C07D 403/12* | (2006.01) |
| *C07D 403/14* | (2006.01) |
| *C07D 405/10* | (2006.01) |
| *C07D 417/10* | (2006.01) |
| *C07D 471/04* | (2006.01) |
| *C07D 471/18* | (2006.01) |
| *C07D 491/048* | (2006.01) |
| *C07D 495/04* | (2006.01) |
| *C07D 495/14* | (2006.01) |
| *C07D 519/00* | (2006.01) |
| *A61K 45/06* | (2006.01) |

(52) U.S. Cl.
CPC ............ *C07D 487/04* (2013.01); *A61P 35/02* (2018.01); *C07D 401/12* (2013.01); *C07D 403/12* (2013.01); *C07D 403/14* (2013.01); *C07D 405/10* (2013.01); *C07D 417/10* (2013.01); *C07D 471/04* (2013.01); *C07D 471/18* (2013.01); *C07D 491/048* (2013.01); *C07D 495/04* (2013.01); *C07D 495/14* (2013.01); *C07D 519/00* (2013.01); *A61K 45/06* (2013.01)

(58) Field of Classification Search
CPC .................................................... C07D 487/04
See application file for complete search history.

(56) References Cited

U.S. PATENT DOCUMENTS 8,586,580 B2    11/2013   Sim et al.

FOREIGN PATENT DOCUMENTS

| CA | 2723185 A1 | 10/2009 | |
|---|---|---|---|
| WO | 2009062258 A1 | 5/2009 | |
| WO | 2011062372 A2 | 5/2011 | |
| WO | 2015038417 A1 | 3/2015 | |
| WO | WO 2015/151006 A1 * | 10/2015 | ........... C07D 473/16 |
| WO | 2016022460 A1 | 2/2016 | |

OTHER PUBLICATIONS

Chemical Abstracts Registry No. 1152473-72-7, indexed in the Registry file on STN CAS Online Jun. 5, 2009. (Year: 2009).*
International Search Report and Written Opinion, PCT/CA2017/000258, dated Feb. 27, 2018, 11 pages.

* cited by examiner

*Primary Examiner* — Laura L Stockton
(74) *Attorney, Agent, or Firm* — Entralta; James F. Fleming; Peter D. Weinstein

(57) ABSTRACT

The present invention relates to fused pyrimidine compounds, particularly pyrrolopyrimidine and thienopyrimidine compounds and derivatives thereof, pharmaceutical compositions thereof, and methods of inhibiting BRD4 and/or JAK2, as well as methods of treating various diseases and conditions, such as cancer and leukemia, with such compounds. Bromodomain binding and JAK activity are included.

10 Claims, No Drawings

FUSED PYRIMIDINE COMPOUNDS AS BRD4 AND JAK2 DUAL INHIBITORS AND METHODS FOR USE THEREOF

CROSS-REFERENCE TO RELATED APPLICATIONS

This application is a 35 U.S.C. § 371 US national stage entry of International Application number PCT/CA2017/000258, filed Dec. 1, 2017. The contents of the aforementioned application are incorporated by reference herein.

This application claims priority to U.S. Provisional Application No. 62/428,756, filed on Dec. 1, 2016, the disclosure of which is hereby incorporated by reference in its entirety for all purposes

FIELD OF THE INVENTION

The present disclosure relates to fused pyrimidine compounds, particularly pyrrolopyrimidine compounds and derivatives thereof, pharmaceutical composition thereof, and methods of inhibiting BRD4 and JAK2, as well as methods of treating various disease and conditions, with such compounds.

BACKGROUND OF THE INVENTION

Bromodomain (BRD)-containing proteins are essential for the recognition of acetylated lysine (KAc) residues of histones during transcriptional activation. BRDs regulate the transcription of various oncogenes, such as c-Myc and Bcl-2. Thus, BRDs have emerged as promising drug targets for a number of disease pathways that are characterized by changes in the epigenetic cell signature. To date, only a few structurally diverse BRD inhibitors have been reported, all of which specifically target the KAc recognition sites of the bromodomain and extra terminal (BET) family of proteins (BRD2, BRD3, BRD4, and BRDT), each containing two tandem BRDs. BET-inhibitors exert a broad spectrum of desirable biological effects such as anticancer and anti-inflammatory properties. Recently, it was discovered that the BRD of BETs interact with diverse kinase inhibitors.

Janus kinase 2 (JAK2) is a non-receptor tyrosine kinase which catalyzes the transfer of a phosphate group from a nucleoside triphosphate donor, such as ATP, to tyrosine residues in proteins. JAK2 is involved in various processes such as cell growth, development, differentiation or histone modifications. Accordingly, gain-of-function mutations in JAK2 has been implicated in cancer cell growth and progression, formation of metastasis, and tumor neovascularization.

Dual targeting of bromondomains and kinases, such as BRD4 and JAK2, offers a promising new strategy to treat conditions mediated by bromodomain activity and tyrosine kinase activity.

SUMMARY OF THE INVENTION

Disclosed herein are fused pyrimidine compounds, particularly pyrrolopyrimidine compounds and derivatives thereof, which inhibit the activity of at least one bromodomain, the activity of at least one Janus kinase, or a combination thereof. In particular embodiments, the compounds inhibit the activity of BRD4, the activity of JAK2 tyrosine kinase, or a combination thereof. Thus, in particular embodiments, the disclosure provides for compounds which are dual BRD4 and JAK2 tyrosine kinase inhibitors.

In embodiments, the present disclosure provides for compounds according to formula (I):

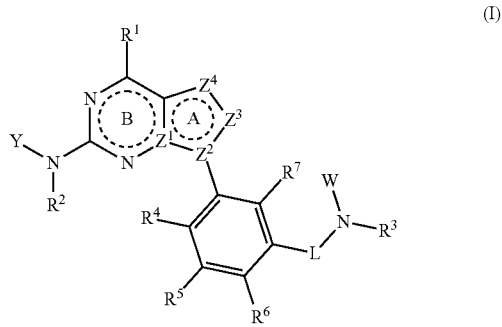

or a pharmaceutically acceptable salt or solvate thereof;
wherein:
$R^1$ is H, halogen, alkyl, haloalkyl, hydroxyl, alkylhydroxyl, alkoxy, haloalkoxy, or —$NR^aR^b$;
$R^2$ and $R^3$ are each independently H or alkyl;
$R^4$ and $R^5$ are each independently H, halogen, hydroxyl or alkyl;
$R^6$ and $R^7$ are each independently H, halogen, hydroxyl or alkyl; or alternatively, $R^6$ and $R^3$ together or $R^7$ and $R^3$ together forms a saturated, unsaturated, or partially saturated, 5- or 6-membered ring;
ring A and ring B are each aromatic;
$Z^1$ is C or N;
$Z^2$ is C, $CR^8$, or N;
$Z^3$ and $Z^4$ are each independently C, $CR^8$, N, or S;
provided that at least one of $Z^1$, $Z^2$, $Z^3$, and $Z^4$ is N or S and at most two of $Z^1$, $Z^2$, $Z^3$, and $Z^4$ is N;
$R^8$ is H, halogen, or alkyl;
L is a bond or —$CH_2$—;
W is —$S(O)_mR^9$, —$P(O)_2R^9$, or —$P(=S)_2R^9$;
$R^9$ is alkyl, cycloalkyl, or aryl, wherein cycloalkyl and aryl is optionally substituted with one or more of halogen or alkyl;
Y is selected from

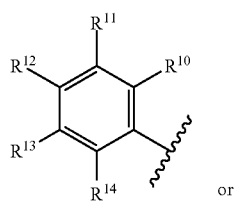

or

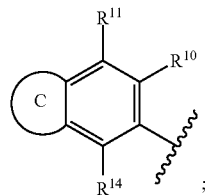

in $Y^1$ and $Y^2$, $R^{10}$ and $R^{14}$ are each independently H, halogen, hydroxyl, alkyl, or alkoxy;
in $Y^1$, $R^{11}$, $R^{12}$ and $R^{13}$ are each independently H, halogen, alkyl, alkoxy, heterocyclyl, —$(CH_2)_n$—$C(O)NR^aR^c$, —(CH₂)ₙ—NRᵃC(O)Rᵈ, —(CH₂)ₙ—C(O)(CH₂)ₙ—, —NRᵃRᵇ, —NRᵃ-alkylene-NRᵃRᵇ or —(CH₂)ₙ—C(O)NRᵃ-alkylene-NRᵃRᵇ; or in $Y^2$, $R^{11}$ is H, halogen, hydroxyl or alkyl;

in $Y^2$, ring C is a monocyclic, bicyclic, or tricyclic 5- to 12-membered heterocycle containing at least one atom selected from N, O, or S, wherein ring C is optionally substituted with $R^{15}$;

$R^a$ and $R^b$ are each independently, H or alkyl;

$R^c$ is H, alkyl, -alkyl-NRᵃRᵇ, or heterocyclyl;

$R^d$ is alkyl, -alkyl-NRᵃRᵇ, or heterocyclyl;

wherein heterocycyl in $R^{11}$, $R^{12}$, $R^{13}$, $R^c$, and $R^d$ is each independently optionally substituted with $R^{15}$;

$R^{15}$ is halogen, hydroxyl, alkyl, alkylhydroxyl, oxo, —C(O)-alkyl, —C(O)ORᵃ; —NRᵃC(O)-alkyl, —(CH₂)ₙ—C(O)NRᵃRᵇ, —NRᵃRᵇ; or —S(O)ₙ-alkyl, n is 0, 1, or 2; and m is 0, 1, or 2;

wherein the compound is not

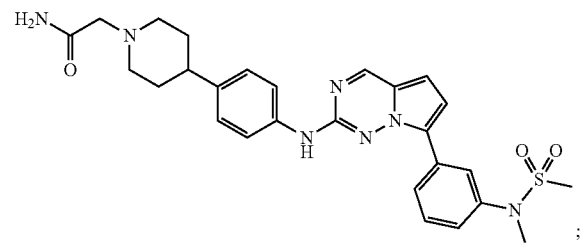

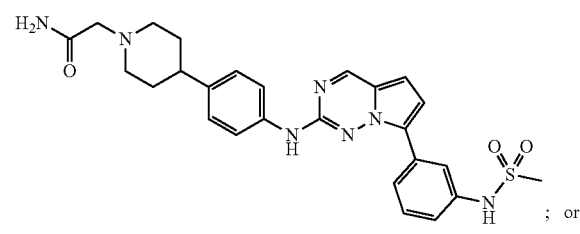

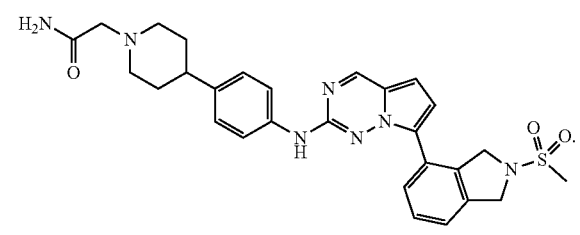

In embodiments, $Z^2$ is N and $Z^1$, $Z^3$, and $Z^4$ are each independently C or $CR^8$.

In embodiments, $Z^1$ is N and $Z^2$, $Z^3$, and $Z^4$ are each independently C or $CR^8$.

In embodiments, $Z^1$ and $Z^3$ are each N, and $Z^2$ and $Z^4$ are each independently C or $CR^8$.

In embodiments, $Z^1$ and $Z^4$ are each N, and $Z^3$ and $Z^4$ are each independently C or $CR^8$.

In embodiments, the compound of formula (I) has the structure according to formula (II)

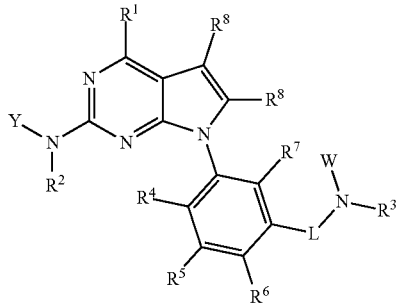

or a pharmaceutically acceptable salt or solvate thereof.

In embodiments, W is —S(O)₂R⁹.

In embodiments, $R^9$ is $C_1$-$C_6$ alkyl or $C_3$-$C_6$ alkyl, each optionally substituted.

In embodiments, L is a bond.

In embodiments, the compound of formula (I) has the structure according to formula (III)

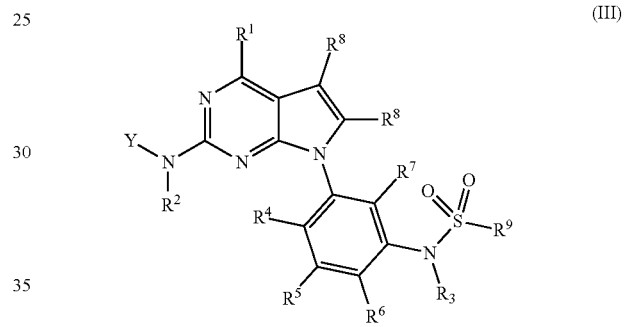

In embodiments, $R^2$ and $R^3$ are each H or $C_1$-$C_3$ alkyl.

In embodiments, $R^4$ and $R^5$ are each H.

In embodiments, $R^6$ and $R^7$ are each independently H or halogen.

In embodiments, $R^6$ and $R^3$ together forms a saturated, unsaturated, or partially saturated, 5- or 6-membered ring.

In embodiments, $R^6$ and $R^3$ together forms a saturated 5-membered ring.

In embodiments, $R^{10}$ and $R^{14}$ are each H.

In embodiments, at least one of $R^{11}$ and $R^{13}$ is a halogen.

In embodiments, Y is $Y^1$.

In embodiments, one of $R^{11}$, $R^{12}$ and $R^{13}$ is an optionally substituted heterocyclyl.

In embodiments, the heterocyclyl is selected from piperidine, piperazine, hexahydropyrimidine, morpholine, tetrahydropyran, thiane, or thiomorpholine, each optionally substituted.

In embodiments, the heterocyclyl is a bicycle.

In embodiments, the heterocyclyl is selected from

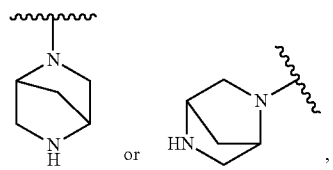 [SMILES: *N1CC2CC1CN2 ; *N1CC2CC1CN2]

each of which is optionally substituted with $R^{15}$.

In embodiments, one of $R^{11}$, $R^{12}$ and $R^{13}$ is —$(CH_2)_n$—C(O)$NR^aR^c$, —$(CH_2)_n$—$NR^aC(O)R^d$, —$(CH_2)_n$—C(O)(CH_2)—, —$NR^aR^b$, —$NR^a$-alkylene-$NR^aR^b$, or —$(CH_2)_n$—C(O)$NR^a$-alkylene-$NR^aR^b$.

In embodiments, one of $R^{11}$, $R^{12}$ and $R^{13}$ is —$NR^a$-alkylene-$NR^aR^b$ or —$(CH_2)_n$—C(O)$NR^a$-alkylene-$NR^aR^b$.

In embodiments, wherein Y is $Y^2$.

In embodiments, $Y^2$ is selected from:

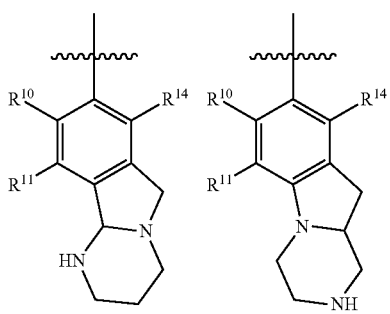

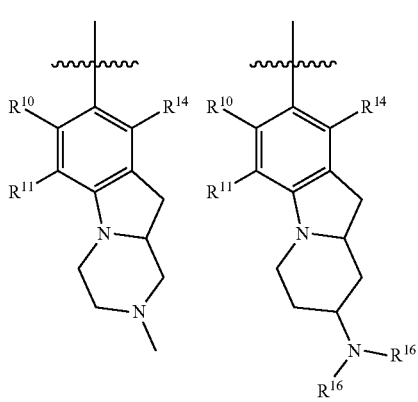

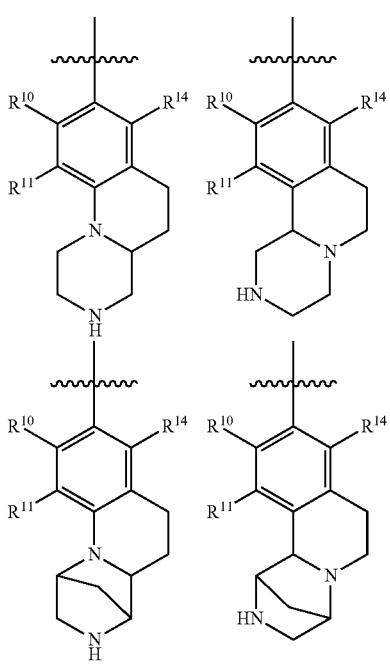

-continued

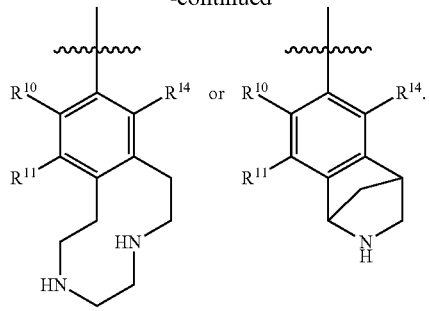

each of which is optionally substituted with $R^{15}$; and $R^{16}$ is H or $C_1$-$C_3$ alkyl.

In embodiments, $R^9$ is $C_1$-$C_6$ alkyl or $C_3$-$C_6$ alkyl, each optionally substituted.

In embodiments, the compound of formula (I) has the structure according to formula (IV)

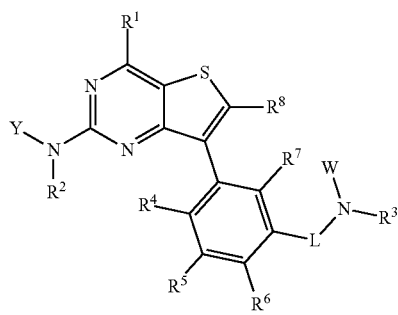

(IV)

or a pharmaceutically acceptable salt or solvate thereof.

In embodiments, W is —$S(O)_2R^9$.

In embodiments, $R^9$ is $C_1$-$C_6$ alkyl or $C_3$-$C_6$ alkyl, each optionally substituted.

In embodiments, L is a bond.

In embodiments, the compound of formula (I) has the structure has a structure according to formula (V)

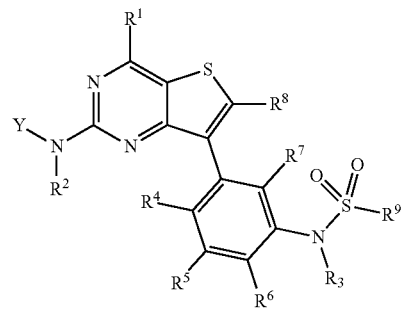

(V)

or a pharmaceutically acceptable salt or solvate thereof.

In embodiments, $R^2$ and $R^3$ are each H or $C_1$-$C_3$ alkyl. In embodiments, $R^4$ and $R^5$ are each H. In embodiments, $R^6$ and $R^7$ are each independently H or halogen. In embodiments, $R^{10}$ and $R^{14}$ are each H.

In embodiments, at least one of $R^{11}$ and $R^{13}$ is a halogen. In embodiments, Y is $Y^1$. In embodiments, one of $R^{11}$, $R^{12}$ and $R^{13}$ is an optionally substituted heterocyclyl. In embodiments, the heterocyclyl is selected from piperidine, piperazine, hexahydropyrimidine, morpholine, tetrahydropyran, thiane, or thiomorpholine, each optionally substituted. In embodiments, the heterocyclyl is a bicycle.

In embodiments, the heterocyclyl is selected from

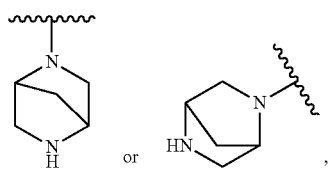 [SMILES: *N1CC2CC1CN2 ; *N1CC2CC1CN2]

each of which is optionally substituted with $R^{15}$.

In embodiments, one of R11, R12 and R13 is —(CH2)n-C(O)NRaRc, —(CH2)n-NRaC(O)Rd, —(CH2)n-C(O)(CH2)n-, —NRaRb, —NRa-alkylene-NRaRb, or —(CH2)n-C(O)NRa-alkylene-NRaRb;

In embodiments, one of R11, R12 and R13 is —NRa-alkylene-NRaRb or —(CH2)n-C(O)NRa-alkylene-NRaRb.

In embodiments, Y is Y2. In embodiments, $Y^2$ is selected from:

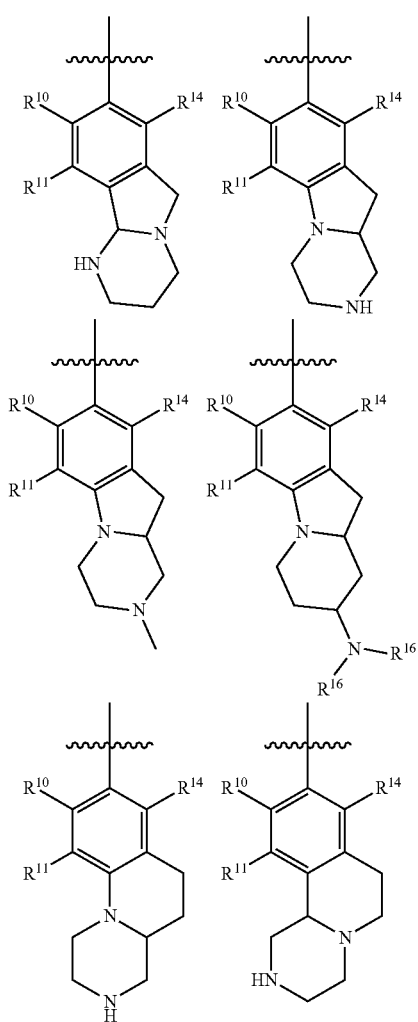

each of which is optionally substituted with $R^{15}$; and $R^{16}$ is H or $C_1$-$C_3$ alkyl.

In embodiments, the compound has a structure according to formula (X):

$$\text{(X)}$$

or a pharmaceutically acceptable salt or solvate thereof;
wherein:
$Z^1$, $Z^2$ and $Z^3$ are each S, N or $CR^8$, provided that at least one of $Z^1$, $Z^2$ or $Z^3$ is N or S and at most two of $Z^1$, $Z^2$ or $Z^3$ is N or S;

ring A and ring B are each aromatic;

V is $$\text{(V}^1\text{)}$$

or

-continued

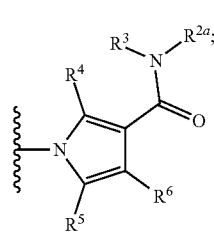
(V²)

L is a bond or —CH$_2$—;

W is —S(O)$_m$R$^9$, —P(O)$_2$R$^9$, or —P(=S)$_2$R$^9$;

R$^2$, R$^{2a}$ and R$^3$ are each independently H or alkyl;

R$^4$ and R$^5$ are each independently H, halogen, hydroxyl or alkyl;

R$^6$ and R$^7$ are each independently H, halogen, hydroxyl or alkyl; or alternatively, R$^6$ and R$^3$ together or R$^7$ and R$^3$ together forms a saturated, unsaturated, or partially saturated, 5- or 6-membered ring;

R$^8$ is H, halogen, or alkyl;

R$^9$ is alkyl, cycloalkyl, or aryl, wherein cycloalkyl and aryl is optionally substituted with one or more of halogen or alkyl;

Y is selected from

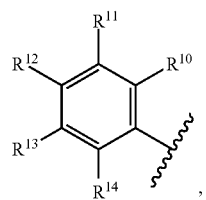
(Y¹)

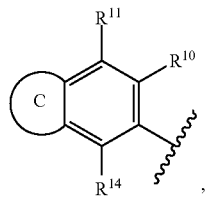
(Y²)

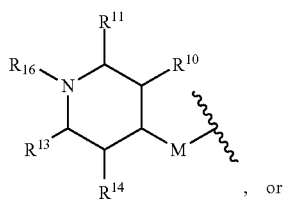
(Y³)

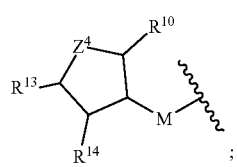
(Y⁴)

in Y¹ and Y², R$^{10}$ and R$^{14}$ are each independently H, halogen, hydroxyl or alkyl;

in Y¹, R$^{11}$, R$^{12}$ and R$^{13}$ are each independently H, halogen, alkyl, alkoxy, heterocyclyl, —(CH$_2$)$_n$—C(O)NR$^a$R$^c$,
—(CH$_2$)$_n$—NRaC(O)R$^d$, —(CH$_2$)$_n$—C(O)(CH$_2$)$_n$—,
—NR$^a$R$^b$, —NR$^a$-alkylene- NR$^a$R$^b$ or —(CH$_2$)$_n$—C(O)NR$^a$-alkylene-NR$^a$R$^b$; or in Y², R$^{11}$ is H, halogen, hydroxyl or alkyl;

in Y², ring C is a monocyclic, bicyclic, or tricyclic 5- to 12-membered heterocycle containing at least one atom selected from N, O, or S, wherein ring C is optionally substituted with in Y³, R$^{10}$, R$^{11}$, R$^{13}$ and R$^{14}$ are each H, halogen, hydroxyl or alkyl;

in Y³, R$^{16}$ is H or alkyl;

in Y⁴, R$^{10}$, R$^{13}$ and R$^{14}$ are each H, halogen, hydroxyl or alkyl;

in Y⁴, Z$^4$ is NR$^a$ or O;

in Y³ and Y⁴, M is a bond or —CH$_2$—;

R$^a$ and R$^b$ are each independently, H or alkyl;

R$^c$ is H, alkyl, -alkyl-NR$^a$R$^b$, or heterocyclyl;

R$^d$ is alkyl, -alkyl-NR$^a$R$^b$, or heterocyclyl;

wherein hetercocycyl in R$^{11}$, R$^{12}$, R$^{13}$, R$^c$, and R$^d$ is each independently optionally substituted with R$^{15}$;

R$^{15}$ is halogen, hydroxyl, alkyl, alkylhydroxyl, oxo, —C(O)-alkyl, —C(O)OR$^a$; —NR$^a$C(O)-alkyl, —(CH$_2$)$_n$—C(O)NR$^a$R$^b$, —NR$^a$R$^b$; or —S(O)$_n$-alkyl, n is 0, 1, or 2; and m is 0, 1, or 2.

In embodiments, Z$^1$, Z$^2$ and Z$^3$ are each S or CR$^8$, wherein exactly one of Z$^1$, Z$^2$ or Z$^3$ is S.

In embodiments, Z$^1$ is S.

In embodiments, Z$^3$ is S.

In embodiments, V is V$^2$.

In embodiments, R$^{2a}$ is H and R$^3$ is alkyl.

In embodiments, R$^{2a}$ is H and R$^3$ is C$_3$-C$_6$ cycloalkyl.

In embodiments, V is

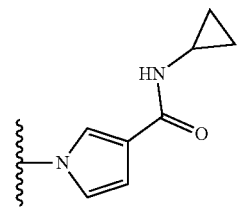

In embodiments, V is V$^1$.

In embodiments, W is —S(O)$_2$R$^9$.

In embodiments, R$^9$ is C$_1$-C$_6$ alkyl or C$_3$-C$_6$ alkyl, each optionally substituted.

In embodiments, L is a bond.

In embodiments, R$^4$ and R$^5$ are each H.

In embodiments, R$^6$ and R$^7$ are each independently H or halogen.

In embodiments, R$^6$ and R$^3$ together forms a saturated, unsaturated, or partially saturated, 5- or 6-membered ring.

In embodiments, R$^6$ and R$^3$ together forms a saturated 5-membered ring.

In embodiments, Y is Y$^1$.

In embodiments, one of R$^{11}$, R$^{12}$ and R$^{13}$ is an optionally substituted heterocyclyl.

In embodiments, the heterocyclyl is selected from piperidine, piperazine, hexahydropyrimidine, morpholine, tetrahydropyran, thiane, or thiomorpholine, each optionally substituted.

In embodiments, the heterocyclyl is a bicycle.

In embodiments, the heterocyclyl is selected from

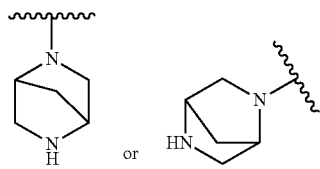

each of which is optionally substituted with $R^{15}$.

In embodiments, one of $R^{11}$, $R^{12}$ and $R^{13}$ is —$(CH_2)_n$—$C(O)NR^aR^c$, —$(CH_2)_n$—$NR^aC(O)R^d$, —$(CH_2)_n$—$C(O)(CH_2)_n$—, —$NR^aR^b$, —$NR^a$-alkylene-$NR^aR^b$, or —$(CH_2)_n$—$C(O)NR^a$-alkylene-$NR^aR^b$.

In embodiments, one of $R^{11}$, $R^{12}$ and $R^{13}$ is —$NR^a$-alkylene-$NR^aR^b$ or —$(CH_2)_n$—$C(O)NR^a$-alkylene-$NR^aR^b$.

In embodiments, Y is $Y^2$.

In embodiments, $Y^2$ is selected from:

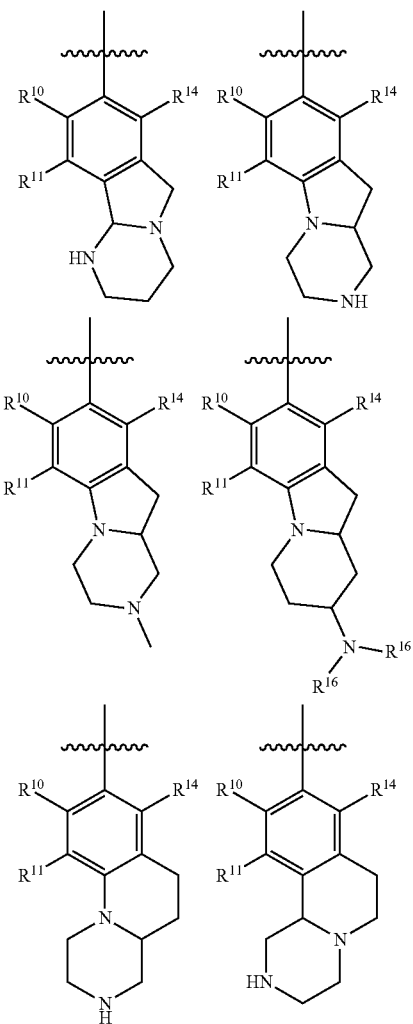

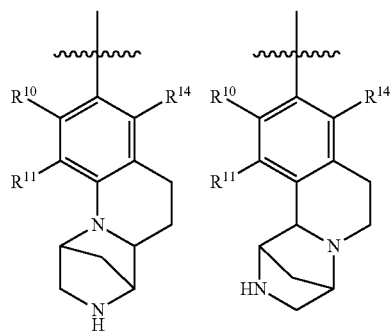

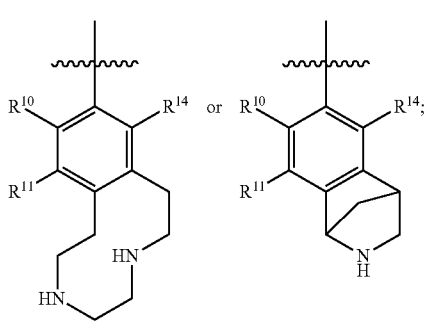

each of which is optionally substituted with $R^{15}$; and $R^{16}$ is H or $C_1$-$C_3$ alkyl.

In embodiments, Y is $Y^3$.

In embodiments, $R^{10}$, $R^{11}$, $R^{13}$ and $R^{14}$ are each H.

In embodiments, $R^{16}$ is H or methyl.

In embodiments, M is —$CH_2$—.

In embodiments, wherein Y is $Y^4$.

In embodiments, $R^{10}$, $R^{13}$ and $R^{14}$ are each H.

In embodiments, $Z^4$ is NH or $NCH_3$.

In embodiments, the compound is selected from:

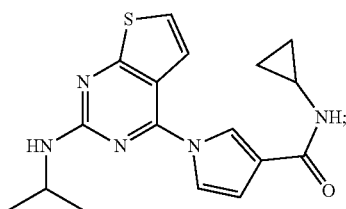

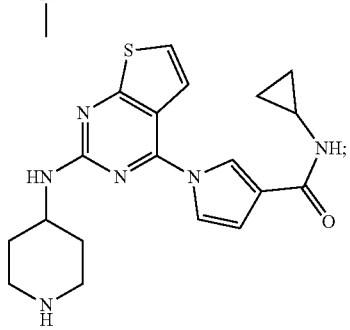

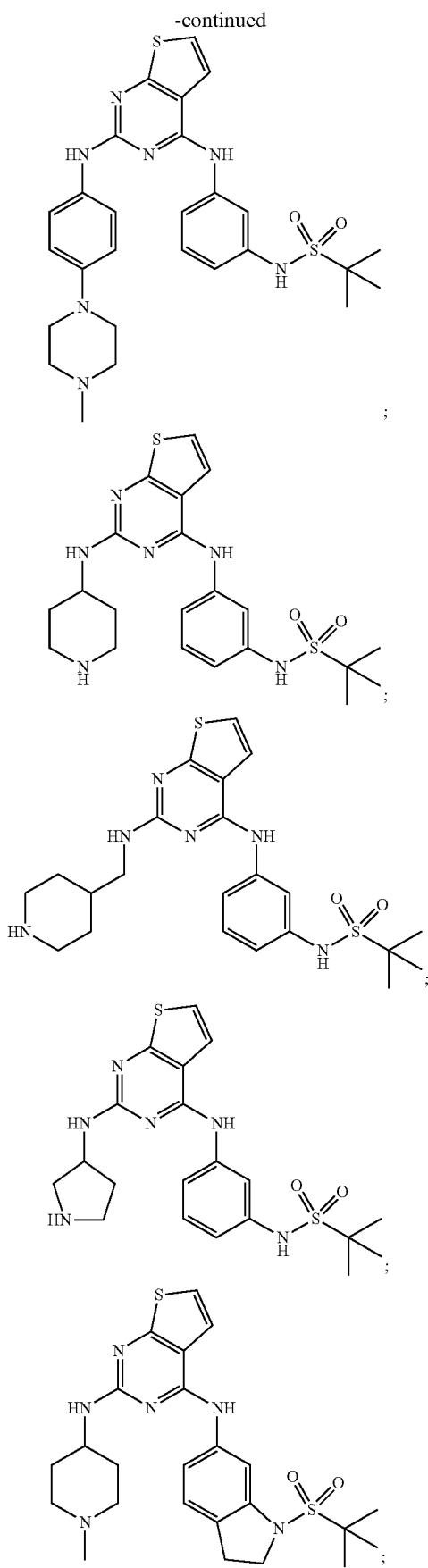

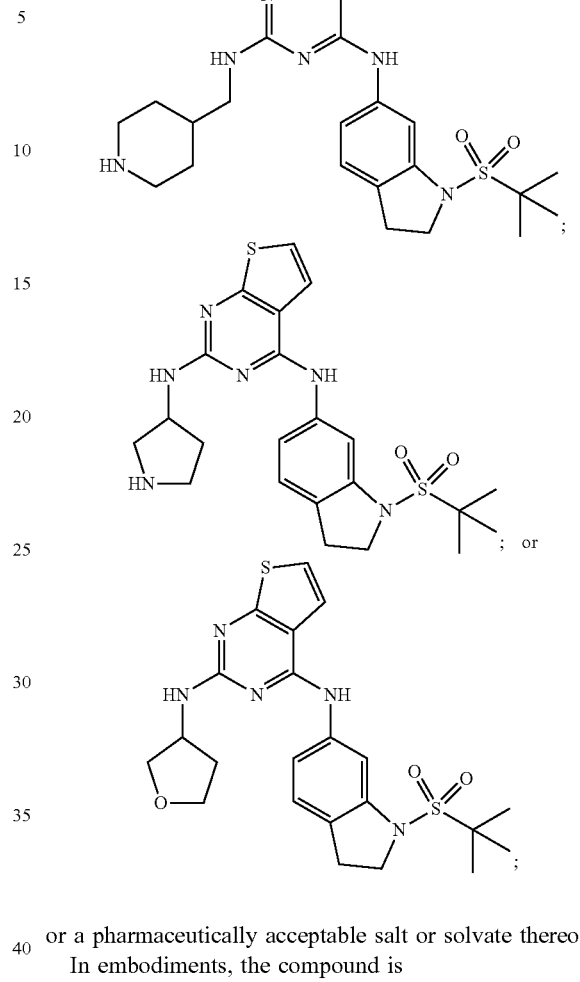

or a pharmaceutically acceptable salt or solvate thereof.

In embodiments, the compound is

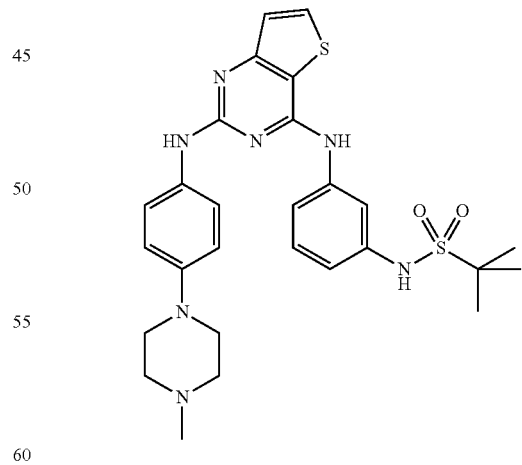

or a pharmaceutically acceptable salt or solvate thereof.

In embodiments, one or more compounds disclosed herein have BRD4-inhibiting activity corresponding to an $IC_{50}$ of 10 μM or less. In some embodiments, the compounds having BRD4-inhibiting activity do not have JAK2 tyrosine kinase inhibiting activity.

In embodiments, one or more compounds disclosed herein have JAK2 tyrosine kinase inhibiting activity corresponding to an $IC_{50}$ of 1.0 µM or less. In some embodiments, the compounds having JAK2 tyrosine kinase inhibiting activity do not have BRD4 inhibiting activity.

In embodiments, one or more compounds disclosed herein have BRD4-inhibiting activity corresponding to an $IC_{50}$ of 10 µM or less and JAK2 tyrosine kinase inhibiting activity corresponding to an $IC_{50}$ of 1.0 µM or less.

In one embodiment, the present disclosure provides a pharmaceutical composition comprising a pharmaceutically acceptable carrier or a pharmaceutically acceptable excipient and a compound disclosed herein or a pharmaceutically acceptable salt or solvate thereof.

In other embodiments, the present disclosure provides for method of treating a disease or condition responsive to the inhibition of a bromodomain-containing protein comprising administering to the subject in need thereof, a therapeutically effective amount of a compound of disclosed herein, or a pharmaceutically acceptable salt thereof. In embodiments, the bromodomain-containing protein is BRD4. In embodiments, wherein the subject is human. In embodiments, the disease or condition is cancer. In embodiments, the cancer is selected from one or more of the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. In embodiments, the present disclosure provides for a method of treating a disease or condition responsive to the inhibition of a JAK2 tyrosine kinase comprising administering to the subject in need thereof, a therapeutically effective amount of a compound disclosed herein, or a pharmaceutically acceptable salt thereof. In embodiments, wherein the subject is human. In embodiments, the disease or condition is cancer. In embodiments, the cancer is selected from one or more of the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

DETAILED DESCRIPTION

While the following terms are believed to be well understood by one of ordinary skill in the art, the following definitions are set forth to facilitate explanation of the presently disclosed subject matter.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a BRD4 and JAK2 dual inhibitor" refers to one or more inhibitors or at least one inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

As used herein, "inhibit" it conjugations thereof refers to a reduction in activity of a target, e.g., BRD4 or JAK2 tyrosine kinase. In some embodiments, "inhibit" refers to substantially complete loss of function or a reduction in activity (e.g., by about 1% or more). Thus, inhibit can include a reduction of activity within the range of from 1% to about 100%, including a values and subranges therein.

The terms below, as used herein, have the following meanings, unless indicated otherwise:

"Amino" refers to the —NH$_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkynyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkylcarbonyl group can be optionally substituted.

"Alkylhydroxyl" refers to a hydroxyl, as defined above, connected to an alkyl, as described above, through a single bond. Non-limiting examples of a an alkylhydroxyl include 1-hydroxypropyl, 1-hydroxybutyl, and the like.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$—$R_c$ where $R_b$ is an alkylene group as defined above and $R_c$ is one or more aryl radicals as defined above, for example, benzyl, diphenylmethyl and the like. Unless stated otherwise specifically in the specification, an aralkyl group can be optionally substituted.

"Aralkenyl" or "arylalkenyl" refers to a radical of the formula —$R_b$—$R_c$ where $R_b$ is an alkenylene group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$—$R_c$ where $R_b$ is an alkynylene group as defined above and $R_c$ is one or more aryl radicals as defined above. Unless stated otherwise specifically in the specification, an aralkynyl group can be optionally substituted.

"Cylic" refers to a ring structure. Cyclic rings can comprise from 3 to 20 atoms in the ring, wherein the atoms which form the ring can include at least one carbon and/or at least one heteroatom. Cyclic rings include monocyclic, bicyclic, and tricyclic ring systems, which may include fused or bridged ring systems. Unless stated otherwise specifically in the specification, a cyclic group can be optionally substituted.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Haloalkoxy" refers to an alkoxy radical, as defined above, that is substituted by one or more halo radicals, as defined above, e.g., 1-fluoropropoxy, 1-fluorobutoxy, and the like. Unless stated otherwise specifically in the specification, a haloalkoxyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclcyl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

"Heterocyclylalkyl" refers to a radical of the formula —$R_b$—$R_e$ where $R_b$ is an alkylene group as defined above and $R_e$ is a heterocyclyl radical as defined above. Unless stated otherwise specifically in the specification, a heterocycloalkylalkyl group can be optionally substituted.

"Heterocyclylalkenyl" refers to a radical of the formula —$R_b$—$R_e$ where $R^b$ is an alkenylene group as defined above and $R_e$ is a heterocyclyl radical as defined above. Unless stated otherwise specifically in the specification, a heterocycloalkylalkenyl group can be optionally substituted.

"Heterocyclylalkynyl" refers to a radical of the formula —$R_b$—$R_c$ where $R_b$ is an alkynylene group as defined above and $R_e$ is a heterocyclyl radical as defined above. Unless stated otherwise specifically in the specification, a heterocycloalkylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$—$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$—$R_f$ where $R_b$ is an alkynylene chain as defined above and $R_f$ is a heteroaryl radical as defined above. Unless stated otherwise specifically in the specification, a heteroarylalkynyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkylhydroxyl, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, haloalkoxy, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol "⊢" (hereinafter can be referred to as "a point of attachment bond") denotes a bond that is a point of attachment between two chemical entities, one of which is depicted as being attached to the point of attachment bond and the other of which is not depicted as being attached to the point of attachment bond. For example, "XY⊢" indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or "XY⊢" infers that when $R^3$ is "XY", the point of attachment bond is the same bond as the bond by which $R^3$ is depicted as being bonded to $CH_3$.

The following description includes information that may be useful in understanding the present invention. It is not an admission that any of the information provided herein is prior art or relevant to the presently claimed inventions, or that any publication specifically or implicitly referenced is prior art.

Compounds of the Present Disclosure

In embodiments, the present disclosure provides for a compound of formula (I'):

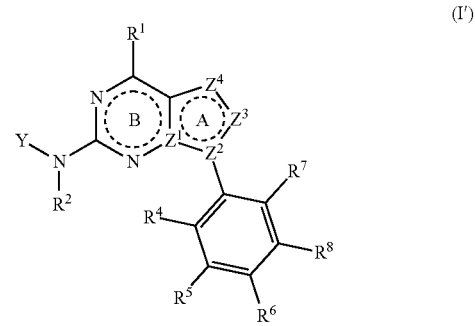

or a pharmaceutically acceptable salt or solvate thereof;
wherein:
$R^1$ is H, halogen, alkyl, haloalkyl, hydroxyl, alkylhydroxyl, alkoxy, haloalkoxy, or —$NR^aR^b$;
$R^2$ and $R^3$ are each independently H or alkyl;
$R^4$ and $R^5$ are each independently H, halogen, hydroxyl or alkyl;
one of $R^6$, $R^7$ or $R^8$ is

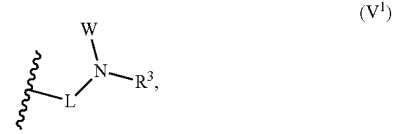

and remaining $R^6$, $R^7$ or $R^8$ are each independently H, halogen, hydroxyl or alkyl;
when $R^8$ is $V^1$, $R^6$ and $R^3$ together or $R^7$ and $R^3$ together can optionally form a saturated, unsaturated, or partially saturated, 5- or 6-membered ring;
when $R^6$ is $V^1$, $R^8$ and $R^3$ together can optionally form a saturated, unsaturated, or partially saturated, 5- or 6-membered ring;
ring A and ring B are each aromatic;
$Z^1$ is C or N;
$Z^2$ is C, $CR^8$, or N;
$Z^3$ and $Z^4$ are each independently C, $CR^8$, N, or S;
provided that at least one of $Z^1$, $Z^2$, $Z^3$, and $Z^4$ is N or S and at most two of $Z^1$, $Z^2$, $Z^3$, and $Z^4$ is N;
$R^8$ is H, halogen, or alkyl;
L is a bond or —$CH_2$—;
W is —$S(O)_mR^9$, —$P(O)_2R^9$, or —$P(=S)_2R^9$;
$R^9$ is alkyl, cycloalkyl, or aryl, wherein cycloalkyl and aryl is optionally substituted with one or more of halogen or alkyl;
Y is selected from

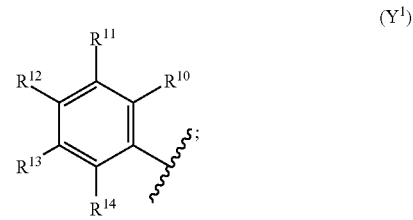

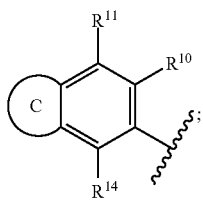

-M-carbocyclyl (Y⁵), or -M-heterocyclyl (Y⁶);

in $Y^1$ and $Y^2$, $R^{10}$ and $R^{14}$ are each independently H, halogen, hydroxyl, alkyl, alkoxy, $-NR^aR^a$;

in $Y^1$, $R^{11}$, $R^{12}$ and $R^{13}$ are each independently H, halogen, alkyl, alkoxy, $-(CH_2)_n$-heterocyclyl, $-(CH_2)_n-C(O)NR^aR^c$, $-(CH_2)_n-NR^aC(O)R^d$, $-(CH_2)_n-C(O)(CH_2)_n-$, $-NR^aR^b$, $-NR^a$-alkylene-$NR^aR^b$, or $-(CH_2)_n-C(O)NR^a$-alkylene-$NR^aR^b$; or in $Y^2$, $R^{11}$ is H, halogen, hydroxyl or alkyl;

in $Y^2$, ring C is a monocyclic, bicyclic, or tricyclic 5- to 12-membered heterocycle containing at least one atom selected from N, O, or S, wherein ring C is optionally substituted with $R^{15}$;

in $Y^5$, carbocycle is monocyclic or bicyclic ring, optionally substituted with one or more $R^{20}$;

in $Y^6$, heterocycle is monocyclic or bicyclic ring containing at least one atom selected from O, S, or N, optionally substituted with one or more $R^{20}$;

$R^{20}$ is each H, halogen, hydroxyl, alkyl, or oxo CN, $-C(O)NR^aR^b$, aralykyl, aryl, heteroaralkyl, heteroaryl;

in $Y^5$ and $Y^6$, M is a bond or $-CH_2-$;

$R^a$ and $R^b$ are each independently, H or alkyl;

$R^c$ is H, alkyl, -alkyl-$NR^aR^b$, or heterocyclyl;

$R^d$ is alkyl, -alkyl-$NR^aR^b$, or heterocyclyl;

wherein hetercocycyl in $R^{11}$, $R^{12}$, $R^{13}$, $R^c$, and $R^d$ is each independently optionally substituted with $R^{15}$;

$R^{15}$ is halogen, hydroxyl, alkyl, alkylhydroxyl, oxo, $-C(O)$-alkyl, $-C(O)OR^a$; $-NR^aC(O)$-alkyl, $-(CH_2)_n-C(O)NR^aR^b$, $-NR^aR^b$; or $-S(O)_n$-alkyl, n is 0, 1, or 2; and m is 0, 1, or 2.

In embodiments, the present disclosure provides for compounds according to formula (I):

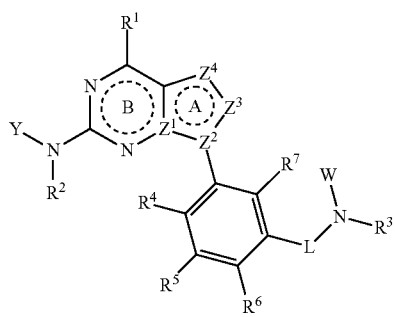

or a pharmaceutically acceptable salt or solvate thereof; wherein:

$R^1$ is H, halogen, alkyl, haloalkyl, hydroxyl, alkylhydroxyl, alkoxy, haloalkoxy, or $-NR^aR^b$;

$R^2$ and $R^3$ are each independently H or alkyl;

$R^4$ and $R^5$ are each independently H, halogen, hydroxyl or alkyl;

$R^6$ and $R^7$ are each independently H, halogen, hydroxyl or alkyl; or alternatively, $R^6$ and $R^3$ together or $R^7$ and $R^3$ together forms a saturated, unsaturated, or partially saturated, 5- or 6-membered ring;

ring A and ring B are each aromatic;

$Z^1$ is C or N;

$Z^2$ is C, $CR^8$, or N;

$Z^3$ and $Z^4$ are each independently C, $CR^8$, N, or S;

provided that at least one of $Z^1$, $Z^2$, $Z^3$, and $Z^4$ is N or S and at most two of $Z^1$, $Z^2$, $Z^3$, and $Z^4$ is N;

$R^8$ is H, halogen, or alkyl;

L is a bond or $-CH_2-$;

W is $-S(O)_mR^9$, $-P(O)_2R^9$, or $-P(=S)_2R^9$;

$R^9$ is alkyl, cycloalkyl, or aryl, wherein cycloalkyl and aryl is optionally substituted with one or more of halogen or alkyl;

Y is selected from

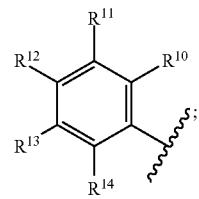

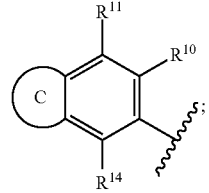

in $Y^1$ and $Y^2$, $R^{10}$ and $R^{14}$ are each independently H, halogen, hydroxyl, alkyl, or alkoxy;

in $Y^1$, $R^{11}$, $R^{12}$ and $R^{13}$ are each independently H, halogen, alkyl, alkoxy, heterocyclyl, $-(CH_2)_n-C(O)NR^aR^c$, $-(CH_2)_n-NR^aC(O)R^d$, $-(CH_2)_n-C(O)(CH_2)_n-$, $-NR^aR^b$, $-NR^a$-alkylene-$NR^aR^b$ or $-(CH_2)_n-C(O)NR^a$-alkylene-$NR^aR^b$; or in $Y^2$, $R^{11}$ is H, halogen, hydroxyl or alkyl;

in $Y^2$, ring C is a monocyclic, bicyclic, or tricyclic 5- to 12-membered heterocycle containing at least one atom selected from N, O, or S, wherein ring C is optionally substituted with $R^{15}$;

$R^a$ and $R^b$ are each independently, H or alkyl;

$R^c$ is H, alkyl, -alkyl-$NR^aR^b$, or heterocyclyl;

$R^d$ is alkyl, -alkyl-$NR^aR^b$, or heterocyclyl;

wherein hetercocycyl in $R^{11}$, $R^{12}$, $R^{13}$, $R^c$, and $R^d$ is each independently optionally substituted with $R^{15}$;

$R^{15}$ is halogen, hydroxyl, alkyl, alkylhydroxyl, oxo, $-C(O)$-alkyl, $-C(O)OR^a$; $-NR^aC(O)$-alkyl, $-(CH_2)_n-C(O)NR^aR^b$, $-NR^aR^b$; or $-S(O)_n$-alkyl, n is 0, 1, or 2; and m is 0, 1, or 2;

wherein the compound is not

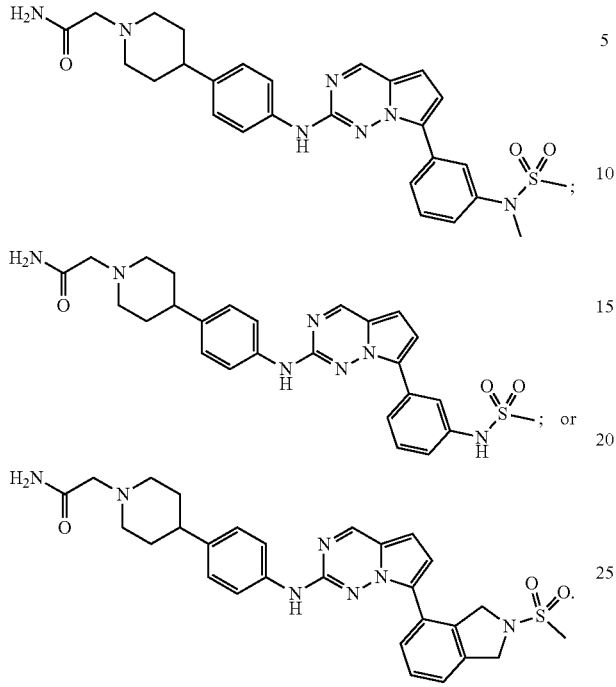

In embodiments, $Z^2$ is N and $Z^1$, $Z^3$, and $Z^4$ are each independently C or $CR^8$.

In embodiments, $Z^1$ is N and $Z^2$, $Z^3$, and $Z^4$ are each independently C or $CR^8$.

In embodiments, $Z^1$ and $Z^3$ are each N, and $Z^2$ and $Z^4$ are each independently C or $CR^8$.

In embodiments, $Z^1$ and $Z^4$ are each N, and $Z^3$ and $Z^4$ are each independently C or $CR^8$.

In embodiments, the compound of formula (I) has the structure has a structure according to formula (II)

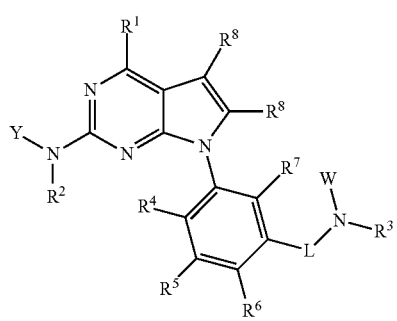

(II)

or a pharmaceutically acceptable salt or solvate thereof.

In embodiments, W is $—S(O)_2R^9$.

In embodiments, $R^9$ is $C_1$-$C_6$ alkyl or $C_3$-$C_6$ alkyl, each optionally substituted.

In embodiments, L is a bond.

In embodiments, the compound of formula (I) has the structure according to formula (III)

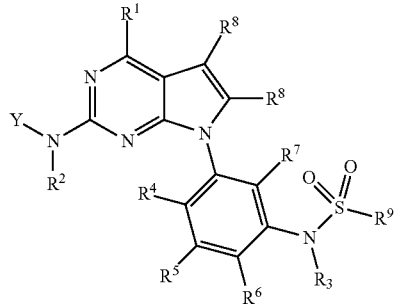

(III)

In embodiments, $R^2$ and $R^3$ are each H or $C_1$-$C_3$ alkyl.

In embodiments, $R^4$ and $R^5$ are each H.

In embodiments, $R^6$ and $R^7$ are each independently H or halogen.

In embodiments, $R^6$ and $R^3$ together forms a saturated, unsaturated, or partially saturated, 5- or 6-membered ring.

In embodiments, $R^6$ and $R^3$ together forms a saturated 5-membered ring.

In embodiments, $R^{10}$ and $R^{14}$ are each H.

In embodiments, at least one of $R^{11}$ and $R^{13}$ is a halogen.

In embodiments, Y is $Y^1$.

In embodiments, one of $R^{11}$, $R^{12}$ and $R^{13}$ is an optionally substituted heterocyclyl.

In embodiments, the heterocyclyl is selected from piperidine, piperazine, hexahydropyrimidine, morpholine, tetrahydropyran, thiane, or thiomorpholine, each optionally substituted.

In embodiments, the heterocyclyl is a bicycle.

In embodiments, the heterocyclyl is selected from

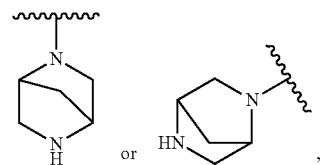 [SMILES: *N1CC2CC1CN2 ; *N1CC2CC1CN2]

each of which is optionally substituted with $R^{15}$.

In embodiments, one of $R^{11}$, $R^{12}$ and $R^{13}$ is $—(CH_2)_n—C(O)NR^aR^c$, $—(CH_2)_n—NR^aC(O)R^d$, $—(CH_2)_n—C(O)(CH_2)_n—$, $—NR^aR^b$, $—NR^a$-alkylene-$NR^aR^b$, or $—(CH_2)_n—C(O)NR^a$-alkylene-$NR^aR^b$.

In embodiments, one of $R^{11}$, $R^{12}$ and $R^{13}$ is $—NR^a$-alkylene-$NR^aR^b$ or $—(CH_2)_n—C(O)NR^a$-alkylene-$NR^aR^b$.

In embodiments, wherein Y is $Y^2$.

In embodiments, $Y^2$ is selected from:

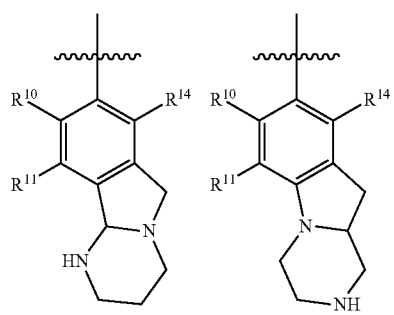

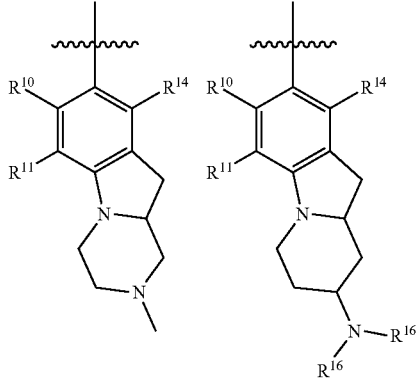

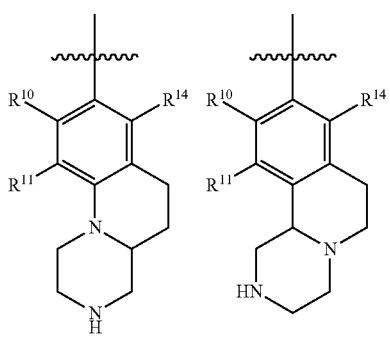

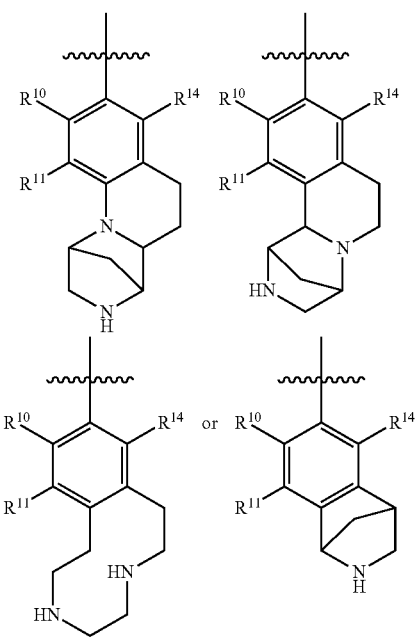

each of which is optionally substituted with $R^{15}$; and $R^{16}$ is H or $C_1$-$C_3$ alkyl.

In embodiments, $R^9$ is $C_1$-$C_6$ alkyl or $C_3$-$C_6$ alkyl, each optionally substituted.

In embodiments, the compound of formula (I) has the structure according to formula (IV)

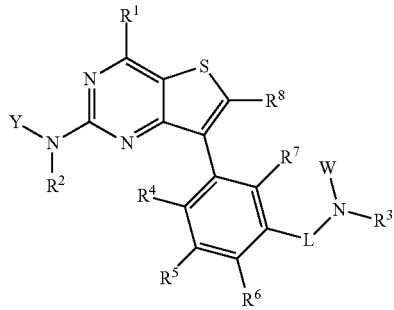

(IV)

or a pharmaceutically acceptable salt or solvate thereof.

In embodiments, W is —S(O)$_2$R$^9$.

In embodiments, $R^9$ is $C_1$-$C_6$ alkyl or $C_3$-$C_6$ alkyl, each optionally substituted.

In embodiments, L is a bond.

In embodiments, the compound of formula (I) has the structure has a structure according to formula (V)

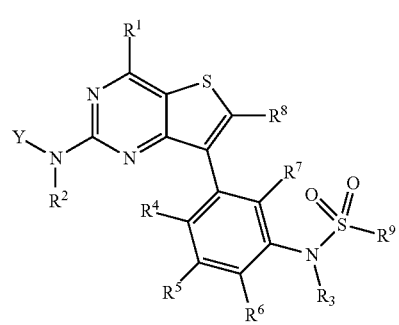

(V)

or a pharmaceutically acceptable salt or solvate thereof.

In embodiments, $R^2$ and $R^3$ are each H or $C_1$-$C_3$ alkyl. In embodiments, $R^4$ and $R^5$ are each H. In embodiments, $R^6$ and $R^7$ are each independently H or halogen. In embodiments, $R^{10}$ and $R^{14}$ are each H.

In embodiments, at least one of $R^{11}$ and $R^{13}$ is a halogen. In embodiments, Y is Y. In embodiments, one of $R^{11}$, $R^{12}$ and $R^{13}$ is an optionally substituted heterocyclyl. In embodiments, the heterocyclyl is selected from piperidine, piperazine, hexahydropyrimidine, morpholine, tetrahydropyran, thiane, or thiomorpholine, each optionally substituted. In embodiments, the heterocyclyl is a bicycle.

In embodiments, the heterocyclyl is selected from

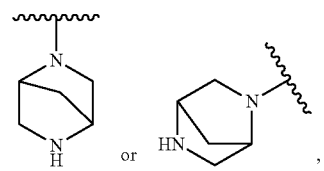 [SMILES: *N1CC2CC1CN2 ; *N1CC2CC1CN2]

each of which is optionally substituted with $R^{15}$.

In embodiments, one of R11, R12 and R13 is —(CH2)n-C(O)NRaRc, —(CH2)n-NRaC(O)Rd, —(CH2)n-C(O)(CH2)n-, —NRaRb, —NRa-alkylene-NRaRb, or —(CH2)n-C(O)NRa-alkylene-NRaRb;

In embodiments, one of R11, R12 and R13 is —NRa-alkylene-NRaRb or —(CH2)n-C(O)NRa-alkylene-NRaRb.

In embodiments, Y is Y2. In embodiments, $Y^2$ is selected from:

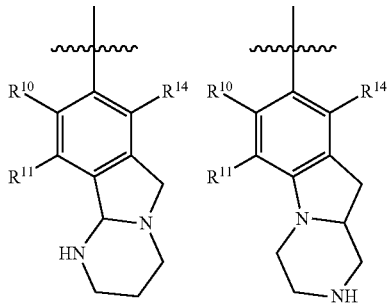
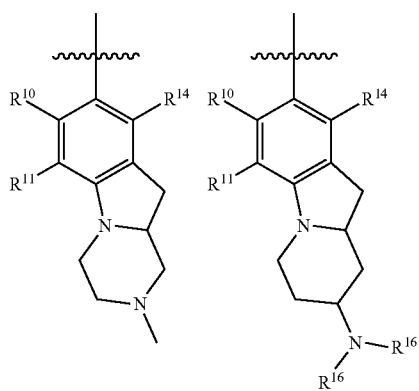
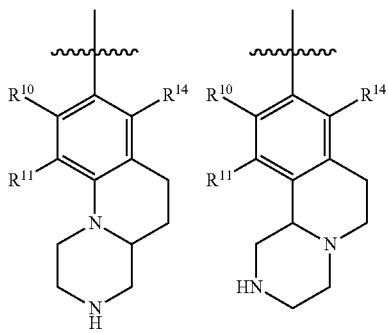
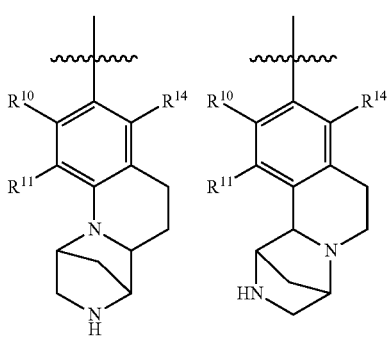
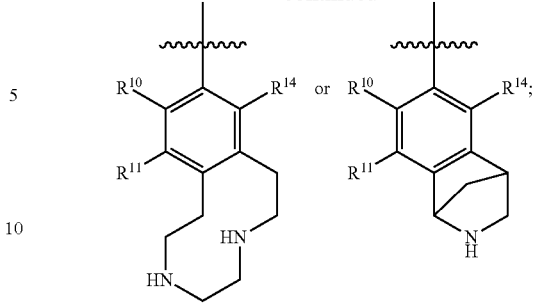

each of which is optionally substituted with $R^{15}$; and $R^{16}$ is H or $C_1$-$C_3$ alkyl.

In embodiments, the disclosure provides for a compound according to formula (X'):

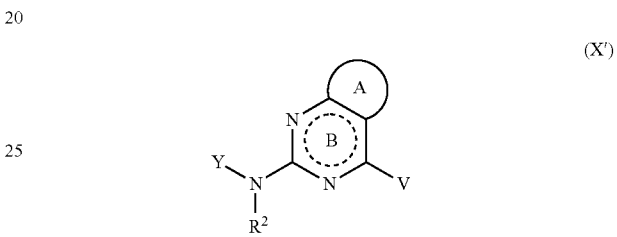

(X')

or a pharmaceutically acceptable salt or solvate thereof; wherein:
Ring A is 5- or 6-membered ring selected from heteroaryl, heterocyclyl, aryl, or carbocylyl;
ring A and ring B are each aromatic;
V is

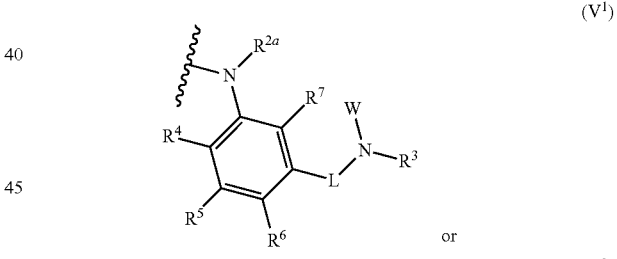

(V¹)

or

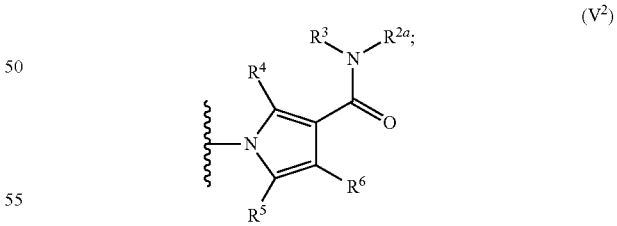

(V²)

L is a bond or —$CH_2$—;
W is —$S(O)_mR^9$, —$P(O)_2R^9$, or —$P(=S)_2R^9$;
$R^2$, $R^{2a}$ and $R^3$ are each independently H or alkyl;
$R^4$ and $R^5$ are each independently H, halogen, hydroxyl or alkyl;
$R^6$ and $R^7$ are each independently H, halogen, hydroxyl or alkyl; or
alternatively, $R^6$ and $R^3$ together or $R^7$ and $R^3$ together forms a saturated, unsaturated, or partially saturated, 5- or 6-membered ring;

R[8] is H, halogen, or alkyl;

R[9] is alkyl, cycloalkyl, or aryl, wherein cycloalkyl and aryl is optionally substituted with one or more of halogen or alkyl;

Y is selected from

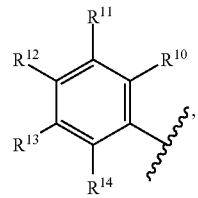
(Y[1])

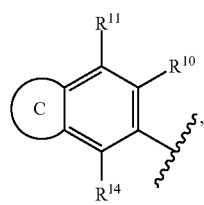
(Y[2])

-M-carbocyclyl (Y[5]), or -M-heterocyclyl (Y[6]);

in Y[1] and Y[2], R[10] and R[14] are each independently H, halogen, hydroxyl or alkyl;

in Y[1], R[11], R[12] and R[13] are each independently H, halogen, alkyl, alkoxy, heterocyclyl, —(CH$_2$)$_n$—C(O)NR$^a$R$^c$, —(CH$_2$)$_n$—NR$^a$C(O)R$^d$, —(CH$_2$)$_n$—C(O)(CH$_2$)$_n$—, —NR$^a$R$^b$, —NR$^a$-alkylene-NR$^a$R$^b$ or —(CH$_2$)$_n$—C(O)NR$^a$-alkylene-NR$^a$R$^b$; or in Y[2], R[11] is H, halogen, hydroxyl or alkyl;

in Y[2], ring C is a monocyclic, bicyclic, or tricyclic 5- to 12-membered heterocycle containing at least one atom selected from N, O, or S, wherein ring C is optionally substituted with R[15];

in Y[5], carbocycle is monocyclic or bicyclic ring, optionally substituted with one or more R[20];

in Y[6], heterocycle is monocyclic or bicyclic ring containing at least one atom selected from O, S, or N, optionally substituted with one or more R[20];

R[20] is each H, halogen, hydroxyl, alkyl, or oxo CN, —C(O)NR$^a$R$^b$, aralykyl, aryl, heteroaralkyl, heteroaryl;

in Y[5] and Y[6], M is a bond or —CH$_2$—;

R$^a$ and R$^b$ are each independently, H or alkyl;

R$^c$ is H, alkyl, -alkyl-NR$^a$R$^b$, or heterocyclyl;

R$^d$ is alkyl, -alkyl-NR$^a$R$^b$, or heterocyclyl;

wherein heterocycyl in R[11], R[12], R[13], R$^c$, and R$^d$ is each independently optionally substituted with R[15];

R[15] is halogen, hydroxyl, alkyl, alkylhydroxyl, oxo, —C(O)-alkyl, —C(O)OR$^a$; —NR$^a$C(O)-alkyl, —(CH$_2$)$_n$—C(O)NR$^a$R$^b$, —NR$^a$R$^b$; or —S(O)$_n$-alkyl, n is 0, 1, or 2; and m is 0, 1, or 2.

In embodiments, the compound has a structure according to formula (X):

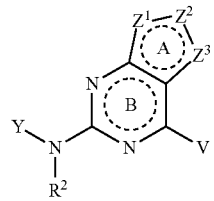
(X)

or a pharmaceutically acceptable salt or solvate thereof;

wherein:

Z[1], Z[2] and Z[3] are each S, N or CR[8], provided that at least one of Z[1], Z[2] or Z[3] is N or S and at most two of Z[1], Z[2] or Z[3] is N or S;

ring A and ring B are each aromatic;

V is

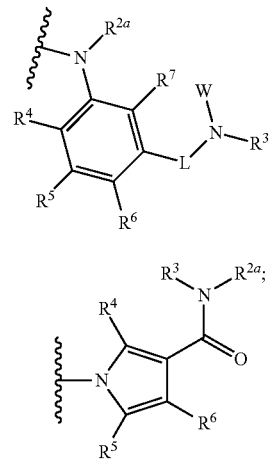

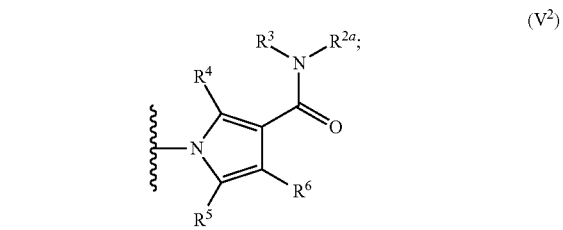

L is a bond or —CH$_2$—;

W is —S(O)$_m$R[9], —P(O)$_2$R[9], or —P(=S)$_2$R[9];

R[2], R[2a] and R[3] are each independently H or alkyl;

R[4] and R[5] are each independently H, halogen, hydroxyl or alkyl;

R[6] and R[7] are each independently H, halogen, hydroxyl or alkyl; or alternatively, R[6] and R[3] together or R[7] and R[3] together forms a saturated, unsaturated, or partially saturated, 5- or 6-membered ring;

R[8] is H, halogen, or alkyl;

R[9] is alkyl, cycloalkyl, or aryl, wherein cycloalkyl and aryl is optionally substituted with one or more of halogen or alkyl;

Y is selected from

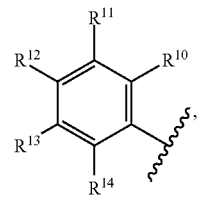
(Y[1])

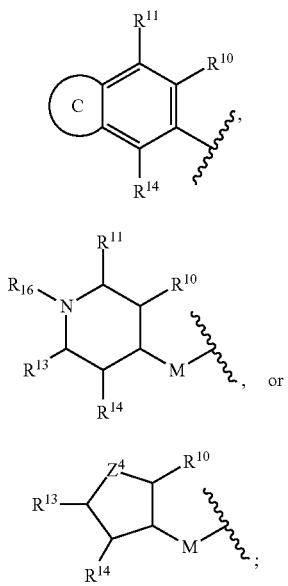

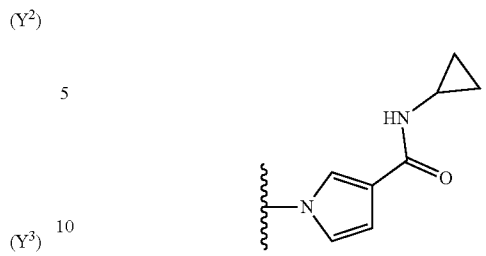

in Y$^1$ and Y$^2$, R$^{10}$ and R$^{14}$ are each independently H, halogen, hydroxyl or alkyl;

in Y$^1$, R$^{11}$, R$^{12}$ and R$^{13}$ are each independently H, halogen, alkyl, alkoxy, heterocyclyl, —(CH$_2$)$_n$—C(O)NR$^a$R$^c$, —(CH$_2$)$_n$—NR$^a$C(O)R$^d$, —(CH$_2$)$_n$—C(O)(CH$_2$)$_n$—, —NR$^a$R$^b$, —NR$^a$-alkylene-NR$^a$R$^b$ or —(CH$_2$)$_n$—C(O)NR$^a$-alkylene-NR$^a$R$^b$; or in Y$^2$, R$^{11}$ is H, halogen, hydroxyl or alkyl;

in Y$^2$, ring C is a monocyclic, bicyclic, or tricyclic 5- to 12-membered heterocycle containing at least one atom selected from N, O, or S, wherein ring C is optionally substituted with R$^{15}$;

in Y$^3$, R$^{10}$, R$^{11}$, R$^{13}$ and R$^{14}$ are each H, halogen, hydroxyl or alkyl;

in Y$^3$, R$^{16}$ is H or alkyl;

in Y$^4$, R$^{10}$, R$^{13}$ and R$^{14}$ are each H, halogen, hydroxyl or alkyl;

in Y$^4$, Z$^4$ is NR$^a$ or O;

in Y$^3$ and Y$^4$, M is a bond or —CH$_2$—;

R$^a$ and R$^b$ are each independently, H or alkyl;

R$^c$ is H, alkyl, -alkyl-NR$^a$R$^b$, or heterocyclyl;

R$^d$ is alkyl, -alkyl-NR$^a$R$^b$, or heterocyclyl;

wherein hetercocycyl in R$^{11}$, R$^{12}$, R$^{13}$, R$^c$, and R$^d$ is each independently optionally substituted with R$^{15}$;

R$^{15}$ is halogen, hydroxyl, alkyl, alkylhydroxyl, oxo, —C(O)-alkyl, —C(O)OR$^a$; —NR$^a$C(O)-alkyl, —(CH$_2$)$_n$—C(O)NR$^a$R$^b$, —NR$^a$R$^b$; or —S(O)$_n$-alkyl, n is 0, 1, or 2; and m is 0, 1, or 2.

In embodiments, Z$^1$, Z$^2$ and Z$^3$ are each S or CR$^8$, wherein exactly one of Z$^1$, Z$^2$ or Z$^3$ is S.

In embodiments, Z$^1$ is S.

In embodiments, Z$^3$ is S.

In embodiments, V is V$^2$.

In embodiments, R$^{2a}$ is H and R$^3$ is alkyl.

In embodiments, R$^{2a}$ is H and R$^3$ is C$_3$-C$_6$ cycloalkyl.

In embodiments, V is

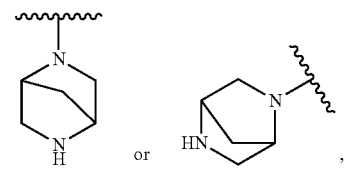 [SMILES: *N1CC2CC1CN2 ; *N1CC2CC1CN2]

In embodiments, V is V$^1$.

In embodiments, W is —S(O)$_2$R$^9$.

In embodiments, R$^9$ is C$_1$-C$_6$ alkyl or C$_3$-C$_6$ alkyl, each optionally substituted.

In embodiments, L is a bond.

In embodiments, R$^4$ and R$^5$ are each H.

In embodiments, R$^6$ and R$^7$ are each independently H or halogen.

In embodiments, R$^6$ and R$^3$ together forms a saturated, unsaturated, or partially saturated, 5- or 6-membered ring.

In embodiments, R$^6$ and R$^3$ together forms a saturated 5-membered ring.

In embodiments, Y is Y$^1$.

In embodiments, one of R$^{11}$, R$^{12}$ and R$^{13}$ is an optionally substituted heterocyclyl.

In embodiments, the heterocyclyl is selected from piperidine, piperazine, hexahydropyrimidine, morpholine, tetrahydropyran, thiane, or thiomorpholine, each optionally substituted.

In embodiments, the heterocyclyl is a bicycle.

In embodiments, the heterocyclyl is selected from

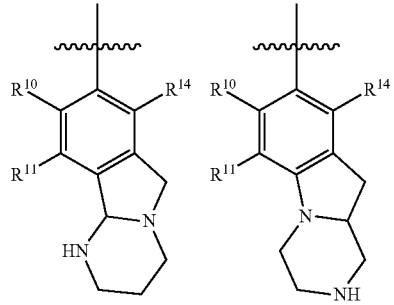

each of which is optionally substituted with R$^5$.

In embodiments, one of R$^{11}$, R$^{12}$ and R$^{13}$ is —(CH$_2$)$_n$—C(O)NR$^a$R$^c$, —(CH$_2$)$_n$—NR$^a$C(O)R$_d$, —(CH$_2$)$_n$—C(O)(CH$_2$)$_n$—, —NR$^a$R$^b$, —NR$^a$-alkylene-NR$^a$R$^b$, or —(CH$_2$)$_n$—C(O)NR$^a$-alkylene-NR$^a$R$^b$.

In embodiments, one of R$^{11}$, R$^{12}$ and R$^{13}$ is —NR$^a$-alkylene-NR$^a$R$^b$ or —(CH$_2$)$_n$—C(O)NR$^a$-alkylene-NR$^a$R$^b$.

In embodiments, Y is Y$^2$.

In embodiments, Y$^2$ is selected from:

37

-continued

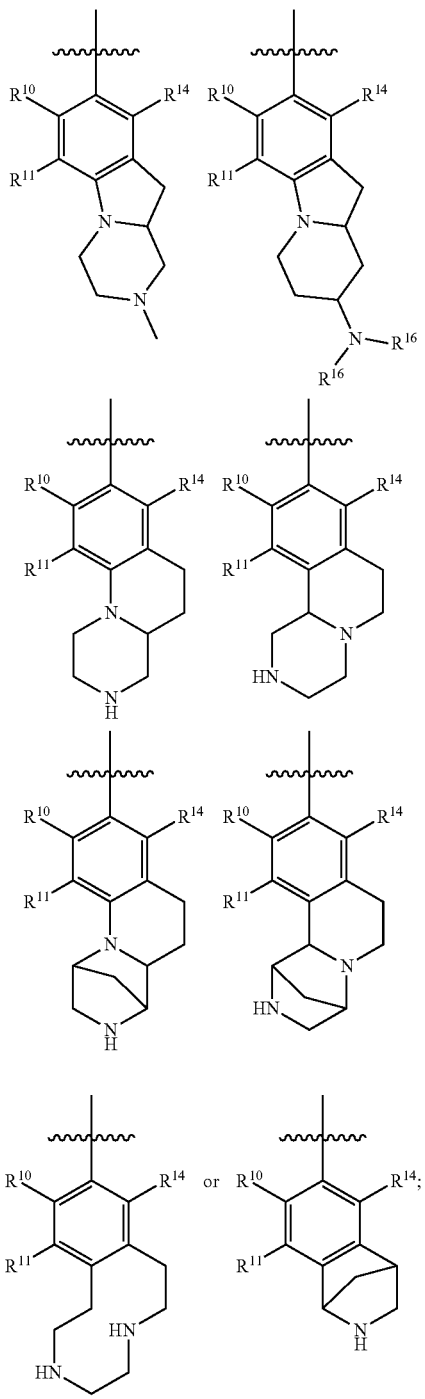

each of which is optionally substituted with $R^{15}$; and $R^{16}$ is H or $C_1$-$C_3$ alkyl.

In embodiments, Y is $Y^3$.
In embodiments, $R^{10}$, $R^{11}$, $R^{13}$ and $R^{14}$ are each H.
In embodiments, $R^{16}$ is H or methyl.
In embodiments, M is —$CH_2$—.
In embodiments, wherein Y is $Y^4$.
In embodiments, $R^{10}$, $R^{13}$ and $R^{14}$ are each H.
In embodiments, $Z^4$ is NH or $NCH_3$.

38

In embodiments, the compound is selected from:

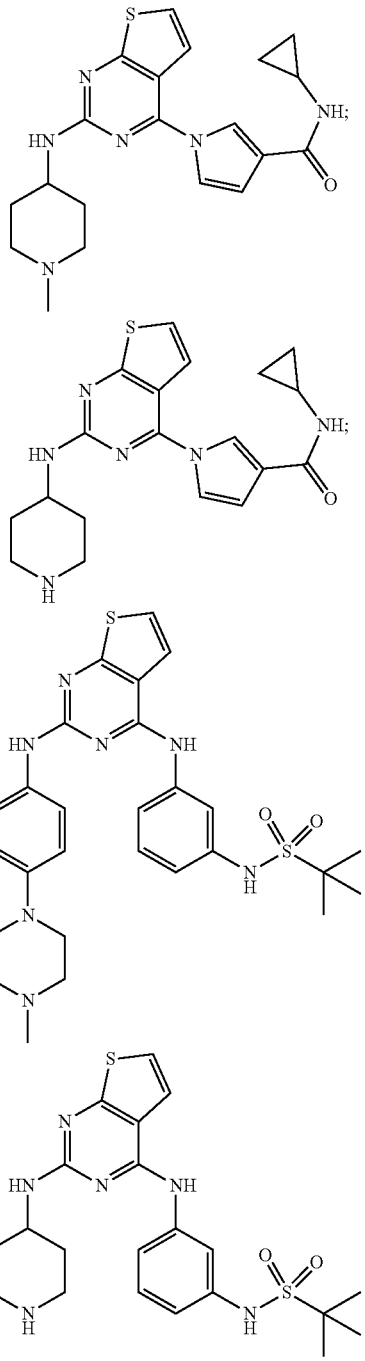

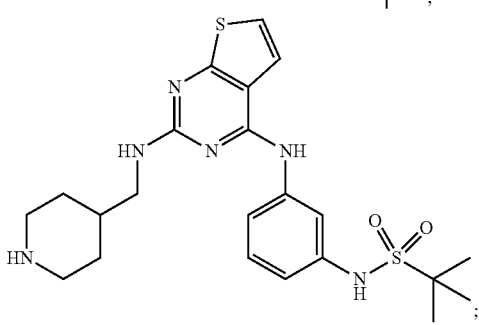

-continued

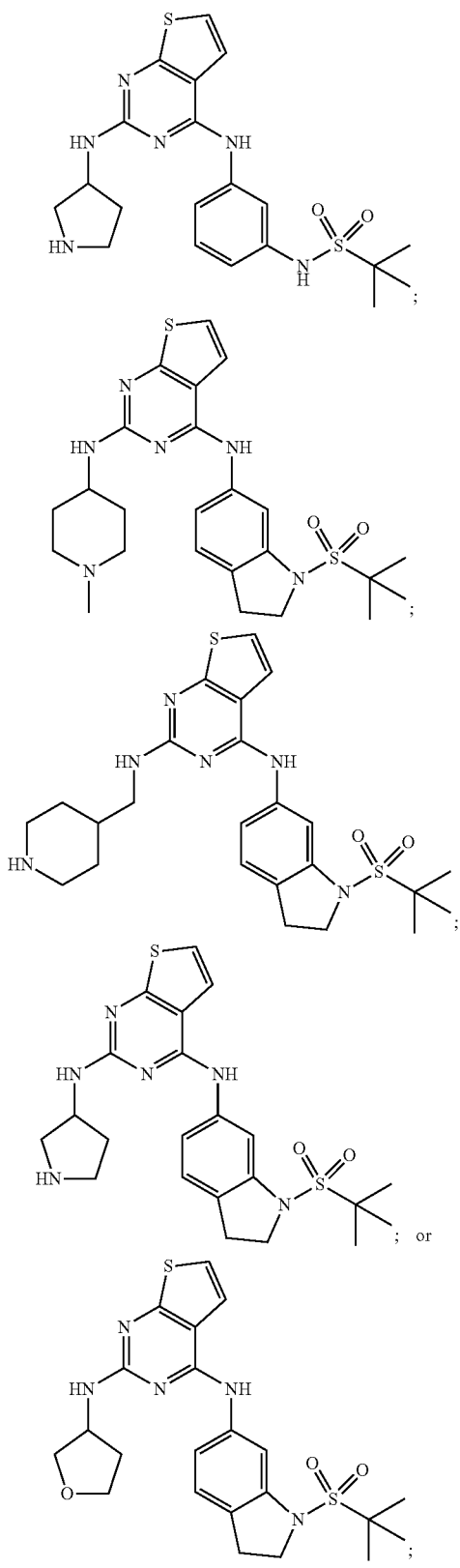

or a pharmaceutically acceptable salt or solvate thereof.

In embodiments, the compound is

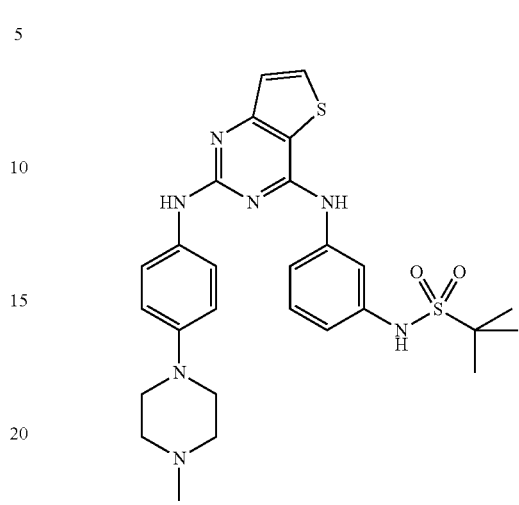

or a pharmaceutically acceptable salt or solvate thereof.

In embodiments, compounds disclosed herein have a BRD4-inhibiting activity corresponding to an IC50 of about 20 μM or less, 10 μM or less, about 5 μM or less, about 1 μM or less, or about 0.1 μM or less. In some embodiments, the compounds with a BRD4-inhibiting activity corresponding to an IC50 of about 0.1 μM or less may have a structure according to formula (IV).

In some embodiments, the compounds with a BRD4-inhibiting activity corresponding to an IC50 of about 0.1 μM or less may include the compounds of Table 1:

TABLE 1

| Structure | BRD4 IC50 (μM) |
|---|---|
| 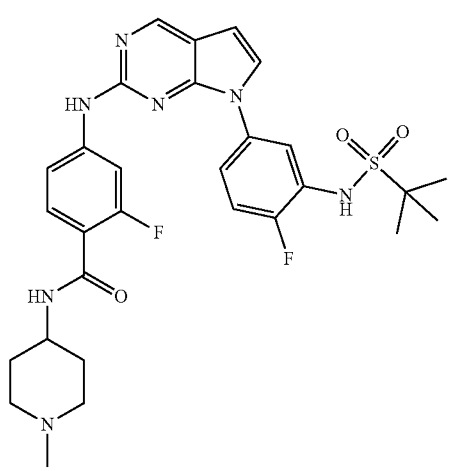 [SMILES: CN1CCC(NC(=O)c2ccc(Nc3ncc4ccn(-c5ccc(F)c(NS(=O)(=O)C(C)(C)C)c5)c4n3)cc2F)CC1] | 0.094 |

TABLE 1-continued

| Structure | BRD4 IC50 (μM) |
|---|---|
| [structure: pyrrolopyrimidine with NH-phenyl-F-piperidine-N(CH3)2 and N-phenyl-F-NHSO2-tBu] | 0.063 |
| [structure: thienopyrimidine with HN-piperidine·HCl and NH-phenyl-NHSO2-tBu] | 0.094 |
| [structure: pyrrolopyrimidine with NH-phenyl-F-piperazine·HCl and N-phenyl-F-NHSO2-tBu] | 0.006 |

In some embodiments, the compounds of the present disclosure exhibit BRD4-inhibitory activity, but are inactive against or show negligible inhibition against JAK2 tyrosine kinase. In such embodiments, the compounds may include the compounds of Table 2.

TABLE 2

| Structure | BRD4 IC50 (μM) |
|---|---|
| [structure: thienopyrimidine with HN-piperidine and NH-phenyl-NHSO2-tBu] | 0.094 |
| [structure: thienopyrimidine with HN-phenyl-piperazine-N-methyl and NH-phenyl-NHSO2-tBu] | 0.388 |
| [structure: thienopyrimidine with HN-CH2-piperidine and NH-phenyl-NHSO2-tBu] | 1.2 |
| [structure: thienopyrimidine with HN-pyrrolidine and NH-phenyl-NHSO2-tBu] | 1.7 |

TABLE 2-continued

| Structure | BRD4 IC50 (μM) |
|---|---|
| (structure) | 0.16 |
| (structure) | 1.0 |
| (structure) | 3.2 |
| (structure) | 2.6 |

TABLE 2-continued

| Structure | BRD4 IC50 (μM) |
|---|---|
| (structure) | 0.450 |
| (structure) | 0.399 |

In embodiments, compounds disclosed herein have a JAK2 tyrosine kinase inhibiting activity corresponding to an IC50 of about 5 μM or less, about 1.0 μM or less, about 0.1 μM or less, about 0.01 μM or less, about 0.005 μM or less, or less or about 0.001 μM or less. In some embodiments, the compounds with a JAK2 tyrosine kinase inhibiting activity corresponding to an IC50 of about 0.005 μM or less may have a structure according to formula (III).

In specific embodiments, the compound with a JAK2 tyrosine kinase inhibiting activity corresponding to an IC50 of about 0.005 μM or less may include at least one of the following compounds of Table 3:

TABLE 3

| Structure | JAK2 IC50 (μM) |
|---|---|
| (structure) | 0.0025 |

TABLE 3-continued

| Structure | JAK2 IC50 (μM) |
|---|---|
| (structure) | 0.003 |
| (structure) ·HCl | 0.002 |
| (structure) | 0.0043 |
| (structure) | 0.0044 |
| (structure) | 0.0048 |
| (structure) | 0.003 |
| (structure) | 0.005 |

In other specific embodiments, the compounds having a JAK2 tyrosine kinase inhibiting activity corresponding to an IC50 of about 0.001 μM or less may include the compounds of Table 4.

TABLE 4

| Structure | JAK2 IC50 (μM) |
|---|---|
| 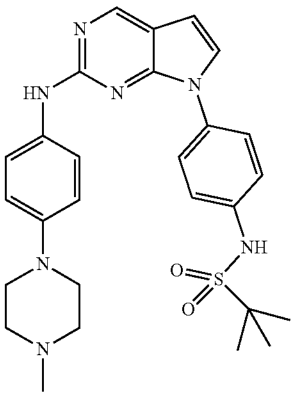 [SMILES: CN1CCN(c2ccc(Nc3ncc4ccn(-c5ccc(NS(=O)(=O)C(C)(C)C)cc5)c4n3)cc2)CC1] | 0.0007 μM |
| 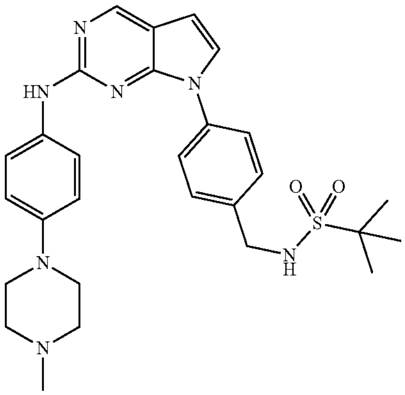 [SMILES: CN1CCN(c2ccc(Nc3ncc4ccn(-c5ccc(CNS(=O)(=O)C(C)(C)C)cc5)c4n3)cc2)CC1] | 0.00018 μM |
| 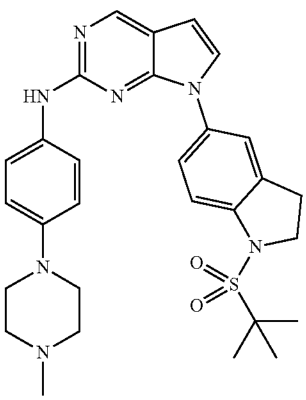 [SMILES: CN1CCN(c2ccc(Nc3ncc4ccn(-c5ccc6c(c5)CCN6S(=O)(=O)C(C)(C)C)c4n3)cc2)CC1] | 0.0006 μM |

In embodiments, compounds disclosed herein have a BRD4-inhibiting activity corresponding to an IC50 of about 10 μM or less and a JAK2 tyrosine kinase inhibiting activity corresponding to an IC50 of about 1.0 μM or less, or a BRD4-inhibiting activity corresponding to an IC50 of about 5 μM or less and a JAK2 tyrosine kinase inhibiting activity corresponding to an IC50 of about 0.1 μM or less, or a BRD4-inhibiting activity corresponding to an IC50 of about 1 μM or less about a JAK2 tyrosine kinase inhibiting activity corresponding to an IC50 of 0.01 or less. In some embodiments, the compounds having a BRD4-inhibiting activity corresponding to an IC50 of about 1.0 μM or less and a JAK2 tyrosine kinase inhibiting activity corresponding to an IC50 of about 0.005 μM or less may have a structure according to formula (VI):

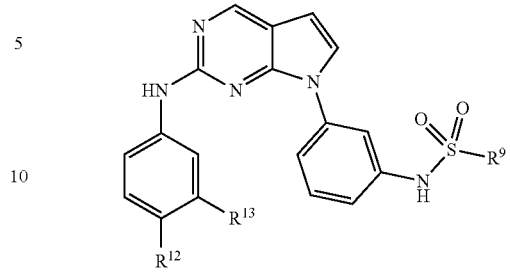

(VI)

wherein:

$R^9$ is alkyl, cycloalkyl, or aryl, wherein cycloalkyl and aryl is optionally substituted with one or more of halogen or alkyl; and $R^{12}$ and $R^{13}$ are each independently H, halogen, alkyl, heterocyclyl, $-(CH_2)_n-C(O)NR^aR^c$, $-(CH_2)_n-NR^aC(O)R^d$, $-(CH_2)_n-C(O)(CH_2)_n-$, $-NR^aR^b$, $-NR^a$-alkylene-$NR^aR^b$, or $-(CH_2)_n-C(O)NR^a$-alkylene-$NR^aR^b$.

$R^a$ and $R^b$ are each independently, H or alkyl;

$R^c$ is H, alkyl, -alkyl-$NR^aR^b$, or heterocyclyl;

$R^d$ is alkyl, -alkyl-$NR^aR^b$, or heterocyclyl; and wherein:

hetercocycyl in $R^{12}$, $R^c$, and $R^d$ is each independently optionally substituted with $R^{15}$;

$R^{15}$ is halogen, hydroxyl, alkyl, alkylhydroxyl, oxo, $-C(O)$-alkyl, $-C(O)OR^a$; $-NR^aC(O)$-alkyl, $-(CH_2)_n-C(O)NR^aR^b$, $-NR^aR^b$; or $-S(O)_n$-alkyl, n is 0, 1, or 2; and m is 0, 1, or 2.

In specific embodiments, the compounds having a BRD4-inhibiting activity corresponding to an IC50 of 1.0 LM or less and with a JAK2 tyrosine kinase inhibiting activity corresponding to an IC50 of 0.005 μM or less may include compounds of Table 5.

TABLE 5

| Structure | BRD4 IC50 (μM) | JAK2 IC50 (μM) |
|---|---|---|
| 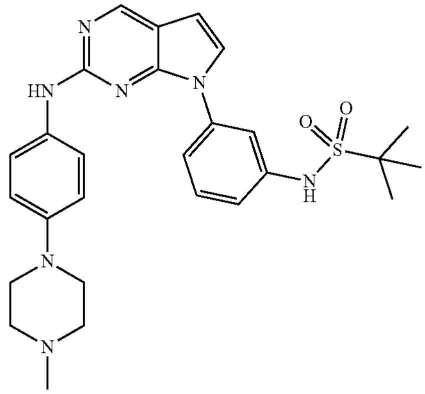 [SMILES: CN1CCN(c2ccc(Nc3ncc4ccn(-c5cccc(NS(=O)(=O)C(C)(C)C)c5)c4n3)cc2)CC1] | 0.22 | 0.0074 |

TABLE 5-continued

| Structure | BRD4 IC50 (μM) | JAK2 IC50 (μM) |
|---|---|---|
| 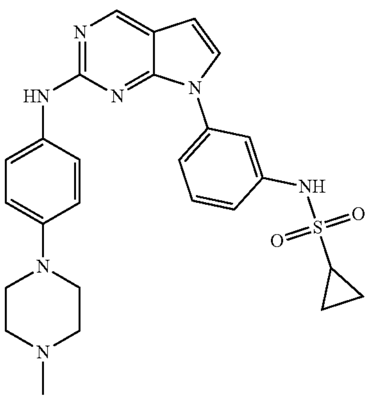 [SMILES: CN1CCN(c2ccc(Nc3ncc4ccn(-c5cccc(NS(=O)(=O)C6CC6)c5)c4n3)cc2)CC1] | 0.355 | 0.0025 |
| 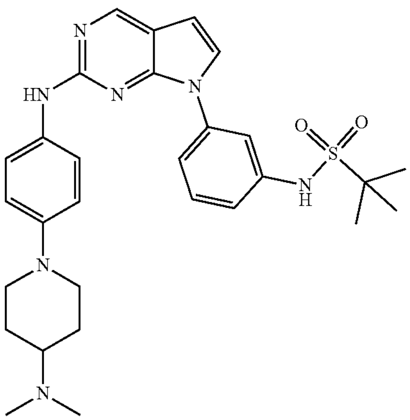 [SMILES: CN(C)C1CCN(c2ccc(Nc3ncc4ccn(-c5cccc(NS(=O)(=O)C(C)(C)C)c5)c4n3)cc2)CC1] | 0.173 | 0.0073 |
| 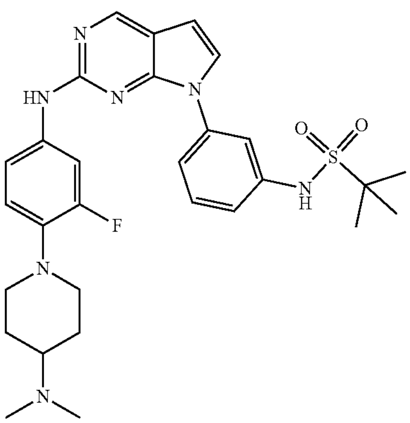 [SMILES: CN(C)C1CCN(c2ccc(Nc3ncc4ccn(-c5cccc(NS(=O)(=O)C(C)(C)C)c5)c4n3)cc2F)CC1] | 0.131 | 0.003 |

In embodiments, the compound of the present disclosure may be selected from one or more of the compounds from Table 6 appended hereto.

Pharmaceutical Compositions and Formulations

In embodiments, the present disclosure provides for pharmaceutical compositions which inhibit the activity of at least one bromodomain, such as a bromodomain on BRDT, BRD2, BRD3, or BRD4. In embodiments, the present disclosure provides for pharmaceutical compositions which inhibit the activity of at least one Janus kinase, such JAK1, JAK2, or JAK3. In embodiments, the present disclosure provides for pharmaceutical compositions which inhibit the activity at least one bromodomain and the activity of at least one Janus Kinase. In particular embodiments, the pharmaceutical compositions of the present disclosure inhibit the activity of BRD4 and the activity of JAK2 tyrosine kinase.

In one embodiment, a pharmaceutical composition comprises one or more compounds of formula (I') (I), (II), (III), (IV), (V), (VI), (X'), or (X), or a pharmaceutically acceptable salt or solvate thereof. In some embodiments, one or more of the compounds of formula (I') (I), (II), (III), (IV), (V), (VI), (X'), or (X), or a pharmaceutically acceptable salt or solvate thereof inhibits the activity at least one bromodomain, such as a bromodomain on BRDT, BRD2, BRD3, or BRD4. In other embodiments, one or more of the compounds of formula (I') (I), (II), (III), (IV), (V), (VI), (X'), or (X), or a pharmaceutically acceptable salt or solvate thereof inhibits the activity of a at least one Janus tyrosine kinase. In another embodiment, the or more of the compounds of formula (I') (I), (II), (III), (IV), (V), (VI), (X'), or (X), or a pharmaceutically acceptable salt or solvate thereof is a dual inhibitor of BRD4 activity and of JAK2 tyrosine kinase activity.

In one embodiment of the present disclosure, a pharmaceutical composition comprises a therapeutically effective amount of one or more compounds of formula (I') (I), (II), (III), (IV), (V), (VI), (X'), or (X), or a pharmaceutically acceptable salt or solvate thereof.

In a specific embodiment, a pharmaceutical composition, as described herein, comprises one or more compounds selected from Table 1, or a pharmaceutically acceptable salt or solvate thereof. In another specific embodiment, a pharmaceutical composition as described herein comprise one or more compounds selected from Table 2, or a pharmaceutically acceptable salt or solvate thereof. In yet another specific embodiment, a pharmaceutical composition as described herein comprise one or more compounds selected from Table 3, or a pharmaceutically acceptable salt or solvate thereof. In still another specific embodiment, a pharmaceutical composition as described herein comprise one or more compounds selected from Table 4, or a pharmaceutically acceptable salt or solvate thereof. In still another specific embodiment, a pharmaceutical composition as described herein comprise one or more compounds selected from Table 5, or a pharmaceutically acceptable salt or solvate thereof. In another specific embodiment, a pharmaceutical composition as described herein comprise one or more compounds selected from Table 6, or a pharmaceutically acceptable salt or solvate thereof.

In one embodiment, a pharmaceutical composition described herein does not contain:

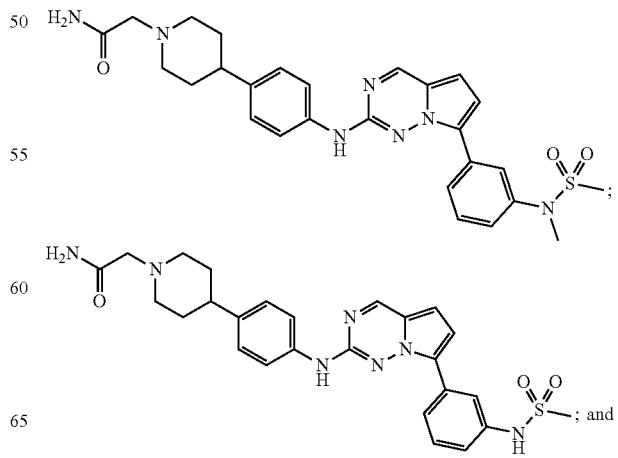

-continued

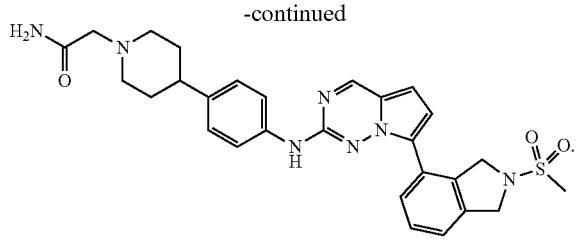

In one embodiment, a pharmaceutical composition, as described herein, comprising one or more compounds of formula ((I') (I), (II), (III), (IV), (V), (VI), (X'), or (X), or a pharmaceutically acceptable salt or solvate thereof, further comprises one or more additional therapeutically active agents. In one embodiment, one or more additional therapeutically active agents are selected from therapeutics useful for treating cancer.

In a further embodiment of the present disclosure, a pharmaceutical composition comprising one or more compounds of formula (I') (I), (II), (III), (IV), (V), (VI), (X'), or (X), or a pharmaceutically acceptable salt or solvate thereof, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more compounds of formula (I') (I), (II), (III), (IV), (V), (VI), (X'), or (X), or a pharmaceutically acceptable salt or solvate thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a compound of formula (I') (I), (II), (III), (IV), (V), (VI), (X'), or (X), or a pharmaceutically acceptable salt or solvate thereof, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 µM and preferably 0.05 µM phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of formula (I') (I), (II), (III), (IV), (V), (VI), (X'), or (X), or a pharmaceutically acceptable salt or solvate thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or compounds, or pharmaceutically acceptable salts or derivatives thereof, are administered orally, nasally, transdermally, pulmonary, inhalationally, buccally, sublingually, intraperitoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the compound is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of formula (I') (I), (II), (III), (IV), (V), (VI), (X'), or (X), or a pharmaceutically acceptable salt or solvate thereof are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of the compound of formula (I') (I), (II), (III), (IV), (V), (VI), (X'), and/or (X), or a pharmaceutically acceptable salt or solvate thereof, or compounds disclosed in Table 1, Table 2, Table 3, Table 4, Table 5, and/or Table 6, or a pharmaceutically acceptable salt or solvate thereof, can be administered at about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compounds or pharmaceutical compositions of the present disclosure may be manufactured and/or administered in single or multiple unit dose forms.

Methods

The present disclosure relates to the use of one or more compounds disclosed herein, or a pharmaceutically acceptable salt thereof, which can inhibit the activity of at least one bromodomain, e.g., a bromondomain on BRDT, BRD2, BRD3, or BRD4. The present disclosure also relates to the use of one or more compounds disclosed herein, or a pharmaceutically acceptable salt thereof, which can inhibit the tyrosine kinase activity of at least one Janus kinase, e.g., JAK1, JAK2, or JAK3. Further, the present disclosure relates to the use of one or more compounds disclosed herein, or a pharmaceutically acceptable salt thereof, which can inhibit the activity of at least one bromodomain (e.g., such as a bromondomain on BRDT, BRD2, BRD3, or BRD4) and the tyrosine kinase activity of at least one Janus kinase (e.g., JAK1, JAK2, or JAK).

More particularly, the present disclosure relates to the use of one or more compounds of formula (I') (I), (II), (III), (IV), (V), (VI), (X'), or (X), or a pharmaceutically acceptable salt or solvate thereof, which can inhibit BRD4 activity, JAK2 tyrosine kinase activity, or a combination thereof. In one embodiment, one or compounds of formula (I') (I), (II), (III), (IV), (V), (VI), (X'), or (X), or a pharmaceutically acceptable salt or solvate thereof, which may inhibit both BRD4 activity and JAK2 tyrosine kinase activity.

In one embodiment, the compounds described herein may be used to treat a cancer selected from one or more of the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In another embodiment the cancer may be selected from one or more of the group consisting of Acute Lymphoblastic Leukemia, Acute Myeloid Leukemia, Adrenocortical Carcinoma, AIDS-Related Cancers, Kaposi Sarcoma, Lymphoma, Anal Cancer, Appendix Cancer, Astrocytomas, Childhood Atypical Teratoid/Rhabdoid Tumor, Basal Cell Carcinoma, Skin Cancer (Nonmelanoma), Childhood Bile Duct Cancer, Extrahepatic Bladder Cancer, Bone Cancer, Ewing Sarcoma Family of Tumors, Osteosarcoma and Malignant Fibrous Histiocytoma, Brain Stem Glioma, Brain Tumors, Embryonal Tumors, Germ Cell Tumors, Craniopharyngioma, Ependymoma, Bronchial Tumors, Burkitt Lymphoma (Non-Hodgkin Lymphoma), Carcinoid Tumor, Gastrointestinal Carcinoma of Unknown Primary, Cardiac (Heart) Tumors, Lymphoma, Primary, Cervical Cancer, Childhood Cancers, Chordoma, Chronic Lymphocytic Leukemia, Chronic Myelogenous Leukemia, Chronic Myeloproliferative Neoplasms Colon Cancer, Colorectal Cancer, Cutaneous T-Cell Lymphoma, Ductal Carcinoma In Situ, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Intraocular Melanoma, Retinoblastoma, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors, Extragonadal Cancer, Ovarian Cancer, Testicular Cancer, Gestational Trophoblastic Disease, Glioma, Brain Stem Cancer, Hairy Cell Leukemia, Head and Neck Cancer, Heart Cancer, Hepatocellular (Liver) Cancer, Histiocytosis, Langerhans Cell Cancer, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Renal Cell Cancer, Wilms Tumor and Other Childhood Kidney Tumors, Langerhans Cell Histiocytosis, Laryngeal Cancer, Leukemia, Chronic Lymphocytic Cancer, Chronic Myelogenous Cancer, Hairy Cell Cancer, Lip and Oral Cavity Cancer, Liver Cancer (Primary), Lobular Carcinoma In Situ (LCIS), Lung Cancer, Non-Small Cell Cancer, Small Cell Cancer, Lymphoma, Cutaneous T-Cell (Mycosis Fungoides and Sézary Syndrome), Hodgkin Cancer, Non-Hodgkin Cancer, Macroglobulinemia, Waldenström, Male Breast Cancer, Malignant Fibrous Histiocytoma of Bone and Osteosarcoma, Melanoma, Intraocular (Eye) Cancer, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia, Acute, Myeloma Multiple, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Epithelial Cancer, Low Malignant Potential Tumor, Pancreatic Cancer, Pancreatic Neuroendocrine Tumors (Islet Cell Tumors), Papillomatosis, Paraganglioma, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Rectal Cancer, Renal Cell (Kidney) Cancer, Retinoblastoma, Rhabdomyosarcoma, Salivary Gland Cancer, Sarcoma, Ewing Cancer, Kaposi Cancer, Osteosarcoma (Bone Cancer), Soft Tissue Cancer, Uterine Cancer, Sézary Syndrome, Skin Cancer, Childhood Melanoma, Merkel Cell Carcinoma, Nonmelanoma, Small Cell Lung Cancer, Small Intestine Cancer, Soft Tissue Sarcoma, Squamous Cell Carcinoma, Skin Cancer (Nonmelanoma), Childhood Squamous Neck Cancer with Occult Primary, Metastatic Cancer, Stomach (Gastric) Cancer, T-Cell Lymphoma, Cutaneous Cancer, Testicular Cancer, Throat Cancer, Thymoma and Thymic Carcinoma, Thyroid Cancer, Transitional Cell Cancer of the Renal Pelvis and Ureter, Unknown Primary, Carcinoma of Childhood, Unusual Cancers of Childhood, Urethral Cancer, Uterine Cancer, Endometrial Cancer, Uterine Sarcoma, Vaginal Cancer, Vulvar Cancer, Waldenström Macroglobulinemia, Wilms Tumor, and Women's Cancers.

In a specific embodiment, the cancer is leukemia.

Having now generally described the invention, the same will be more readily understood through reference to the following examples, which are provided by way of illustration and are not intended to be limiting of the present invention.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

EXAMPLES

Example 1: Bromodomain Binding and IC50 Calculation

An AlphaLisa assay was used to observe bromodomain binding and measure IC50s for the compounds disclosed herein. An AlphaLisa assay is a bead-based assay used to detect interactions between bromodomains and polyacetylated histone peptides. Donor and acceptor beads bound to target and ligand are brought into proximity by this protein-protein interaction. Excitation of the donor beads provokes the release of singlet oxygen that triggers a cascade of energy transfer reactions in the acceptor beads, resulting in a sharp peak of light emission at 615 nm.

Equipment Required
1. 384-well Optiplate from Perkin elmer (cat #6007299)
2. Plate centrifuge
3. Plate shaker
4. 96-well v-bottomed plates from Corning (Cat #3363)
5. Single channel and multi-channel pipettes
6. Microplate reader (Pherastar)

Stock and Final Assay Concentrations (FAC)
1. All reference and test compounds are made at a concentration of 10 mM in DMSO. Compounds are serially diluted in DMSO and a FAC starting from 10 µM to 10 point 3 fold serial dilutions is arrived. FAC of DMSO is 1%.
2. Enzyme stock and FAC

| Enzyme | Stock concentration in µM | FAC in nM |
|---|---|---|
| BRD4-BD1 | 123.6 | 5 |
| BRD4-BD2 | 91.1 | 20 |
| BRD2-BD1 | 34.0 | 15 |
| BRD3-BD! | 23.8 | 8 |
| BRDT-BD1 | 76.2 | 15 |

BRD4-BD1 GST tagged: BPS bioscience Cat: 31040
BRD4-BD2 GST tagged: BPS bioscience Cat: 31041
BRD2-BD1 GST tagged: BPS bioscience Cat: 31021
BRD3-BD1 GST tagged: BPS bioscience Cat: 31032
BRDT-BD1 GST tagged: BPS bioscience Cat: 31108

3. Biotinylated substrate (Acetylated histone H4, biotinylated substrate—cat no. AS64989-025, Anaspec) stock and FAC

| Enzyme | Sub-Stock concentration in μM | FAC in nM |
|---|---|---|
| BRD4-BD1 | 36.65 | 25 |
| BRD4-BD2 | 36.65 | 50 |
| BRD2-BD1 | 36.65 | 50 |
| BRD3-BD! | 36.65 | 35 |
| BRDT-BD1 | 36.65 | 50 |

4. Acceptor and donor beads stock and FAC

| Bead | Stock concentration in mg/ml | Working Stock in μg/ml |
|---|---|---|
| Glutathione Acceptor | 5 | 25 |
| Streptavidin Donor | 5 | 50 |

Glutathione Acceptor beads: Perkin Elmer Cat: AL109M
Streptavidin Donor beads: Perkin Elmer Cat: 6760002
5. Buffers
For the enzyme and substrate dilution following buffer is used (for 50 ml)
HEPES: 50 mM 2.5 ml
NaCl: 25 mM 1.25 ml
DTT: 10 mM 0.05 ml
BSA: 0.1% 0.05 g
MilliQ water: 45.7 ml
For dilution of acceptor and donor beads AlphaLISA 5× epigenetics Buffer Perkin Elmer (Cat: AL008C) is used at 1× concentration.

Procedure
1. Add 20 μl of the diluted compound to each well of the 384-well opti plate
2. Tap the plate gently
3. Add 10 μl of the enzyme to each well of the opti plate
4. Cover with plate sealer
5. Spin the plate briefly (640 rpm for 30 s) in a plate centrifuge.
6. Incubate the plate at room temperature for 10 minutes
7. Add 10 μl of the substrate
8. Cover with plate sealer
9. Spin the plate briefly (640 rpm for 30 s) in a plate centrifuge.
10. Cover with plate sealer and incubate at room temperature for 1 hour
11. After incubation, transfer 10 μl of reaction mix to fresh wells of a 384-well plate.
12. Add 10 μl acceptor bead from working stock.
13. Cover with plate sealer
14. Spin the plate briefly (640 rpm for 30 s) in a plate centrifuge.
15. Cover with plate sealer and incubate at room temperature for 30 minutes
16. Add 10 μl donor bead from working stock (in dark).
17. Cover with plate sealer
18. Spin the plate briefly (640 rpm for 30 s) in a plate centrifuge.
19. Cover with plate sealer and incubate at room temperature for 15-30 minutes
20. Read the plate in pherastar (alpha screen protocol)

Calculations
The percent inhibition is calculated in the excel analysis template and the IC50 values are subsequently determined using a sigmoidal dose-response curve (variable slope) using GraphPad Prism® 5 software.

Example 2: JAK Activity and IC50 Calculation

A kinase assay with HTRF was used to observe JAK activity and calculate the IC50s of compounds disclosed herein. HTRF is an enzymatic assay used to determine the amount of phosphorylated peptide. FRET (Fluorescence Resonance Energy Transfer) is based on the transfer of energy between two fluorophores—a donor and an acceptor—when in close proximity. Molecular interactions between biomolecules can be assessed by coupling each partner with a fluorescent label and by detecting the level of energy transfer. The amount of phopshorylated peptide can be detected using a combination of a Eu 3+Cryptate labeled anti-phospho residue antibody, SA-XL665 and a biotinylated substrate. The signal is proportional to the concentration of phospho-residues.

Equipment Required
1. 384-well black plate from Corning (cat #3575)
2. Plate centrifuge
3. Plate shaker
4. 96-well v-bottomed plates from Corning (Cat #3363)
5. Single channel and multi-channel pipettes
6. Microplate reader (Pherastar)]

Stock and Final Assay Concentrations (FAC)
1. All reference and test compounds are made at a concentration of 10 mM in DMSO. Compounds are serially diluted in DMSO and a FAC starting from 10 μM to 10 point 3 fold serial dilutions is arrived. For Ruxolitinib the starting FAC is 1 μM. FAC of DMSO is 1%.
2. Enzyme stock and FAC

| Enzyme | Stock concentration in μM | FAC in nM |
|---|---|---|
| JAK1 | 3.12 | 10 |
| JAK2 | 6 | 0.5 |
| JAK3 | 5.34 | 1 |

JAK-1: Invtirogen Cat: PR8767C
JAK-2: Invtirogen Cat: PR7820B
JAK-3: Invtirogen Cat: PR7507B
3. Substrate (synthetic peptide-Biotinylated-N-terminal tag-EQEDEPEGDYFEWLE from Biopeptide) stock and FAC

| Enzyme | Stock concentration in mM | FAC in nM |
|---|---|---|
| JAK1 | 1 | 500 |
| JAK2 | 1 | 250 |
| JAK3 | 1 | 500 |

4. ATP stock and FAC

| Enzyme | Stock concentration in mM | FAC in nM |
|---|---|---|
| JAK1 | 10 | 25000 |
| JAK2 | 10 | 500 |
| JAK3 | 10 | 500 |

Adenosine 5'-triphosphate disodium salt hydrate: Sigma Cat: A26209
5. HTRF reagent stock and FAC
Streptavidin-XL665 (Cisbio Cat: 610SAXAC): 1 mg/mL, streptavidin concentration is 16.6 µM Conc. in assay: 12 nM (based on streptavidin concentration)
Europium-W1024-PT-66 Anti Phospho Tyrosine Ab (Perkin Elmer Cat: AD0068): Conc. in assay: 0.1 nM [100 ug/ml stock (3.125 uM)].
HTRF mix:
HTRF buffer: 25 mL
SA-XL665: 18 µL
Eu-PT66Ab: 1 µl
6. Buffers
Base buffer (for 50 ml)

| | |
|---|---|
| HEPES 60 mM | 3 ml |
| NaCl 50 mM | 2.5 ml |
| MgCl2 20 mM | 1 mL |
| MnCl2 5 mM | 250 µL |
| DTT 1M | 100 µL |
| BSA (5%) | 500 µL |
| Sodium orthovandate 0.1M | 50 µL |
| Milli Q water pH 7.4 | 42.6 ml |

HTRF buffer:
50 mM Tris-HCl, pH—7.5
100 mM NaCl
0.1% BSA
0.05% Tween20
0.5 mM EDTA
Procedure
To a 384 well black-plate:
1. Add 17 µL of the buffer to each well of the 384-well black plate
2. Add 8 µl of the diluted compound to each well of the 384-well plate
3. Add 5 µl of the enzyme to each well of the plate
4. Add 10 µl of the substrate and ATP mix to all the wells
5. Cover with plate sealer
6. Spin the plate briefly (640 rpm for 30 s) in a plate centrifuge.
7. Incubate at room temperature for 1 hour on shaker
8. After incubation, transfer 5 µl of reaction mix to fresh wells of a 384-well plate. Add 37.5 µL of the HTRF mix to these wells.
9. Incubate the plate at room temperature on shaker for 45 minutes.
10. Take the reading in Pherastar in HTRF mode (ext 337 nm, em 665 & 620 nm)

Calculations

The percent inhibition is calculated in the excel analysis template and the IC50 values are subsequently determined using a sigmoidal dose-response curve (variable slope) using GraphPad Prism® 5 software.

TABLE 6

| Structure | BRD4(1) IC50 (µM) | JAK2 IC50 (µM) | BRD4(2) IC50 (µM) | BRD2(1) IC50 (µM) | BRD3(1) IC50 (µM) | BRDT(1) IC50 (µM) | JAK1 IC50 (µM) | JAK3 IC50 (µM) |
|---|---|---|---|---|---|---|---|---|
| 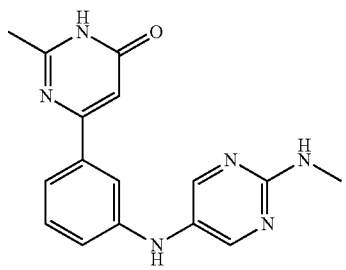 | NA | NA | | | | | | |
| 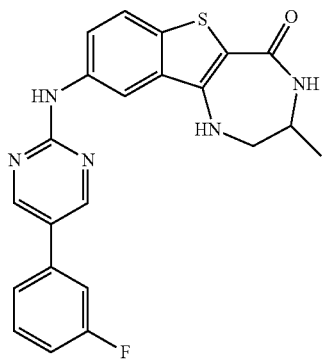 [SMILES: CC1CNc2c(sc3ccc(Nc4ncc(-c5cccc(F)c5)cn4)cc23)C(=O)N1] | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 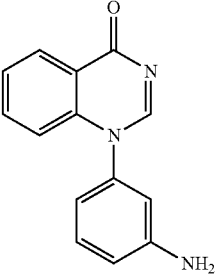 [SMILES: Nc1cccc(-n2cnc(=O)c3ccccc32)c1] | NA | NA | | | | | | |
| 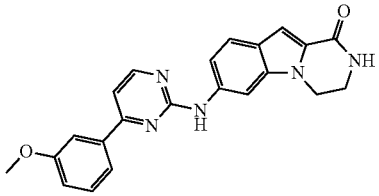 [SMILES: COc1cccc(-c2ccnc(Nc3ccc4cc5n(c4c3)CCNC5=O)n2)c1] | NA | NA | | | | | | |
| 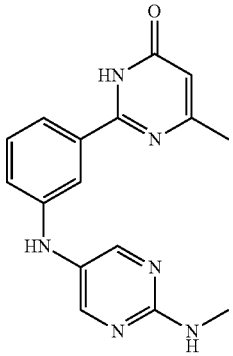 [SMILES: CNc1ncc(Nc2cccc(-c3nc(C)cc(=O)[nH]3)c2)cn1] | NA | NA | | | | | | |
| 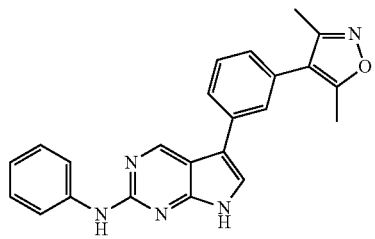 [SMILES: Cc1noc(C)c1-c1cccc(-c2c[nH]c3nc(Nc4ccccc4)ncc23)c1] | NA | NA | | | | | | |
| 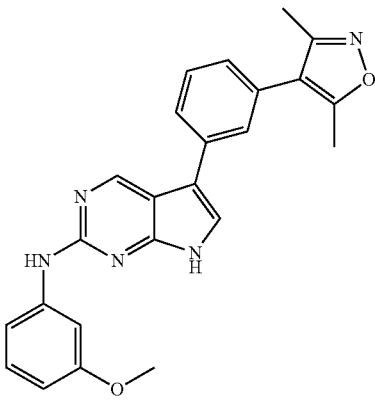 [SMILES: COc1cccc(Nc2ncc3c(-c4cccc(-c5c(C)noc5C)c4)c[nH]c3n2)c1] | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 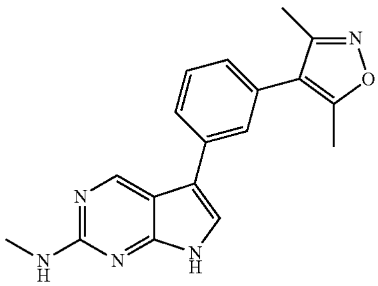 [SMILES: CNc1ncc2c(-c3cccc(-c4c(C)noc4C)c3)c[nH]c2n1] | 10.00 | NA | | | | | | |
| 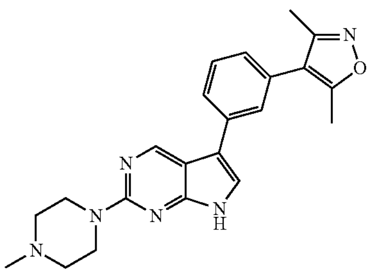 [SMILES: Cc1noc(C)c1-c1cccc(-c2c[nH]c3nc(N4CCN(C)CC4)ncc23)c1] | 7.19 | NA | | | | | | |
| | NA | NA | | | | | | |
| | NA | NA | | | | | | |
| | NA | NA | | | | | | |
| | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 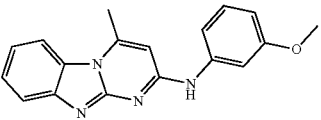 [SMILES: COc1cccc(Nc2cc(C)n3c(n2)nc2ccccc23)c1] | NA | NA | | | | | | |
| 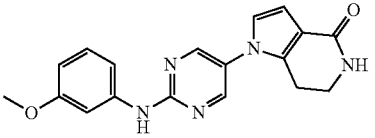 [SMILES: COc1cccc(Nc2ncc(-n3ccc4c3CCNC4=O)cn2)c1] | NA | NA | | | | | | |
| 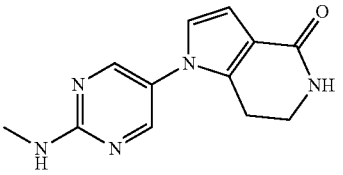 [SMILES: CNc1ncc(-n2ccc3c2CCNC3=O)cn1] | NA | NA | | | | | | |
| 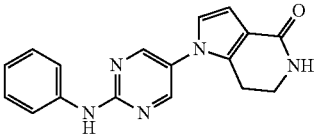 [SMILES: O=C1NCCc2c1ccn2-c1cnc(Nc2ccccc2)nc1] | 1.78 | NA | | | | | | |
| 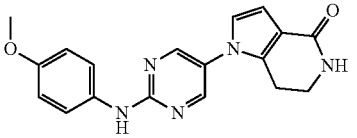 [SMILES: COc1ccc(Nc2ncc(-n3ccc4c3CCNC4=O)cn2)cc1] | 9.74 | NA | | | | | | |
| 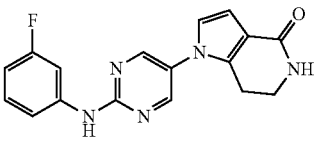 [SMILES: O=C1NCCc2c1ccn2-c1cnc(Nc2cccc(F)c2)nc1] | NA | NA | | | | | | |
| 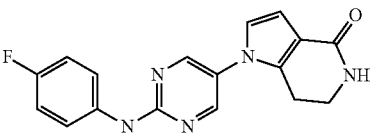 | 11.18 | NA | | | | | | |
| 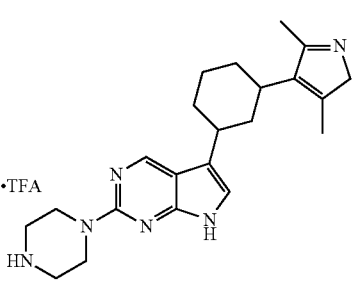 [SMILES: CC1=NCC(C)=C1C1CCCC(c2c[nH]c3nc(N4CCNCC4)ncc23)C1] | 4.06 | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| | NA | NA | | | | | | |
| | NA | NA | | | | | | |
| | NA | NA | | | | | | |
| | NA | NA | | | | | | |
| | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| | NA | NA | | | | | | |
| | NA | NA | | | | | | |
| | NA | 6.78 | | | | | | |
| | NA | NA | | | | | | |
| | NA | NA | | | | | | |
| | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
|  | NA | NA |  |  |  |  |  |  |
|  | NA | NA |  |  |  |  |  |  |
|  | NA | 0.0038 |  |  |  |  |  |  |
| 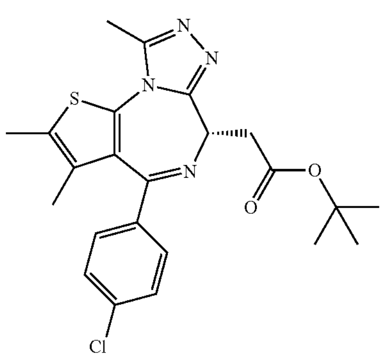 [SMILES: Cc1sc2c(c1C)C(c1ccc(Cl)cc1)=N[C@@H](CC(=O)OC(C)(C)C)c1nnc(C)n1-2] | 0.224 | NA |  |  |  |  |  |  |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure) | 0.211 | 0.012 | | | | | | |
| (structure) | NA | NA | | | | | | |
| (structure) | NA | NA | | | | | | |
| (structure) | NA | NA | | | | | | |
| (structure) | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure) | 4.89 | NA | | | | | | |
| (structure) | NA | 0.546 | | | | | | |
| (structure) | NA | NA | | | | | | |
| (structure) | NA | NA | | | | | | |
| (structure) | NA | NA | | | | | | |
| (structure) | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 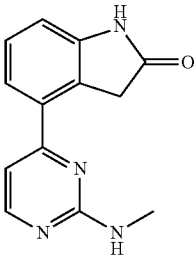 [SMILES: CNc1nccc(-c2cccc3c2CC(=O)N3)n1] | NA | NA | | | | | | |
| 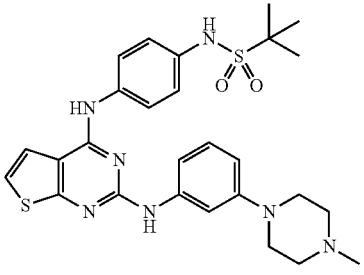 [SMILES: CN1CCN(c2cccc(Nc3nc(Nc4ccc(NS(=O)(=O)C(C)(C)C)cc4)c4ccsc4n3)c2)CC1] | NA | NA | | | | | | |
| 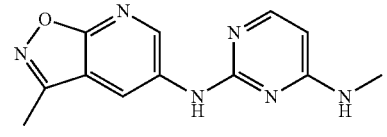 [SMILES: CNc1ccnc(Nc2cnc3onc(C)c3c2)n1] | NA | NA | | | | | | |
| 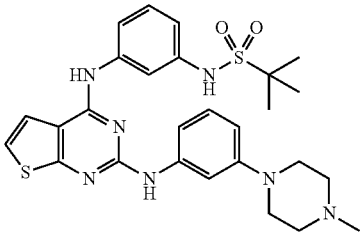 [SMILES: CN1CCN(c2cccc(Nc3nc(Nc4cccc(NS(=O)(=O)C(C)(C)C)c4)c4ccsc4n3)c2)CC1] | 5.02 | NA | | | | | | |
| 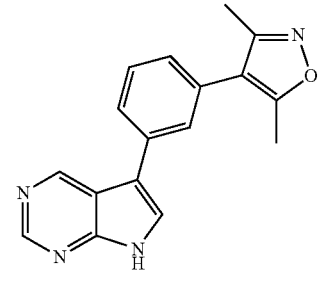 [SMILES: Cc1noc(C)c1-c1cccc(-c2c[nH]c3ncncc23)c1] | NA | NA | | | | | | |
| 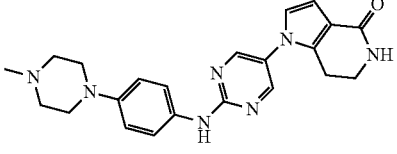 | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | NA | NA | | | | | | |
| *structure* | NA | NA | | | | | | |
| *structure* | NA | NA | | | | | | |
| *structure* | NA | NA | | | | | | |
| *structure* | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| [structure] | NA | NA | | | | | | |
| [structure] | NA | 2.25 | | | | | | |
| [structure] | 3.61 | NA | | | | | | |
| [structure] | NA | NA | | | | | | |
| [structure] | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 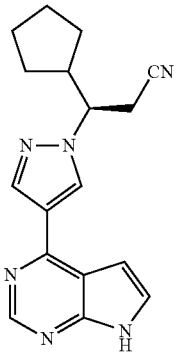 [SMILES: N#CC[C@H](C1CCCC1)n1cc(-c2ncnc3[nH]ccc23)cn1] | NA | #REF! | | | | | | |
| 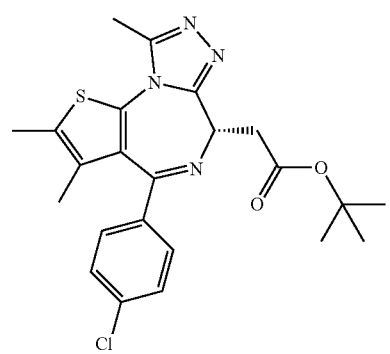 [SMILES: Cc1sc2c(c1C)C(c1ccc(Cl)cc1)=N[C@@H](CC(=O)OC(C)(C)C)c1nnc(C)n1-2] | 0.103 | NA | | | | | | |
| 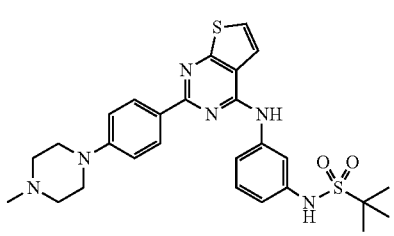 [SMILES: CN1CCN(c2ccc(-c3nc(Nc4cccc(NS(=O)(=O)C(C)(C)C)c4)c4ccsc4n3)cc2)CC1] | NA | NA | | | | | | |
| 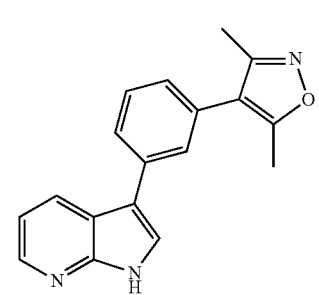 [SMILES: Cc1noc(C)c1-c1cccc(-c2c[nH]c3ncccc23)c1] | NA | NA | | | | | | |
| 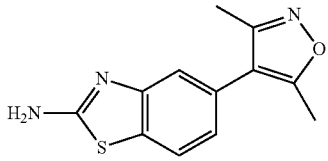 [SMILES: Cc1noc(C)c1-c1ccc2sc(N)nc2c1] | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *(structure)* | NA | NA | | | | | | |
| *(structure)* | NA | NA | | | | | | |
| *(structure)* | 5.72 | 5.92 | | | | | | |
| *(structure)* | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| [structure] ·HCl | 7.40 | NA | | | | | | |
| [structure] ·HCl | 0.094 | NA | | | | | | |
| [structure] | NA | NA | | | | | | |
| [structure] | 0.609 | NA | | | | | | |
| [structure] | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 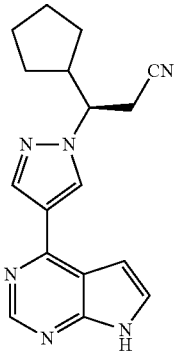 | NA | 0.0013 | | | | | | |
| 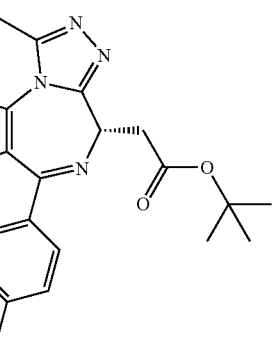 | 0.114 | NA | | | | | | |
| 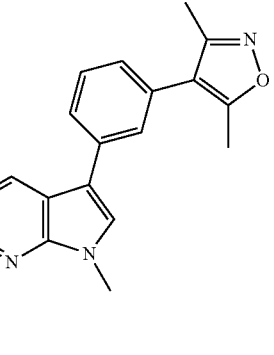 | 4.40 | NA | | | | | | |
| 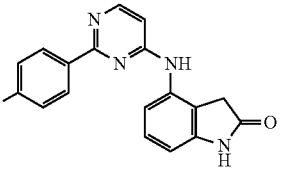 | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| [structure] ·HCl | 0.344 | NA | | | | | | |
| [structure] | NA | NA | | | | | | |
| [structure] | NA | NA | | | | | | |
| [structure] | NA | NA | | | | | | |
| [structure] | NA | NA | | | | | | |
| [structure] | 0.376 | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 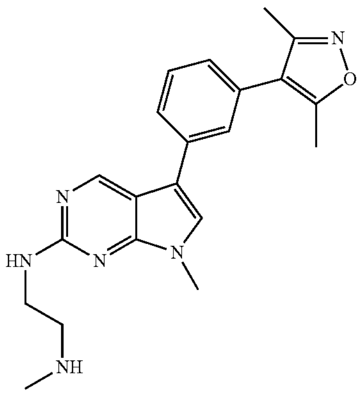 [SMILES: CNCCNc1ncc2c(-c3cccc(-c4c(C)noc4C)c3)cn(C)c2n1] | 7.50 | NA | | | | | | |
| | NA | 0.387 | | | | | | |
| | NA | NA | | | | | | |
| | NA | NA | | | | | | |
| | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| [structure] ·HCl | 3.23 | NA | | | | | | |
| [structure] ·HCl | NA | NA | | | | | | |
| [structure] | 4.56 | NA | | | | | | |
| [structure] | 0.64 | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | NA | NA | | | | | | |
| *structure* | NA | NA | | | | | | |
| *structure* | 2.39 | NA | | | | | | |
| *structure* | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 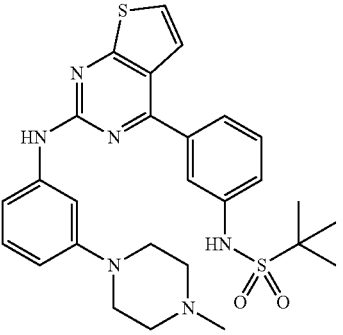 [SMILES: CN1CCN(c2cccc(Nc3nc(-c4cccc(NS(=O)(=O)C(C)(C)C)c4)c4ccsc4n3)c2)CC1] | NA | NA | | | | | | |
| 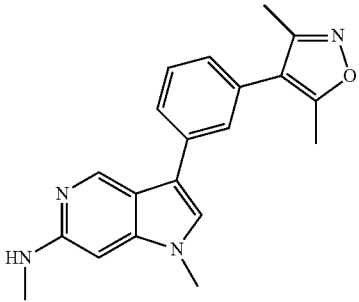 [SMILES: CNc1cc2c(cn1)c(-c1cccc(-c3c(C)noc3C)c1)cn2C] | NA | NA | | | | | | |
| 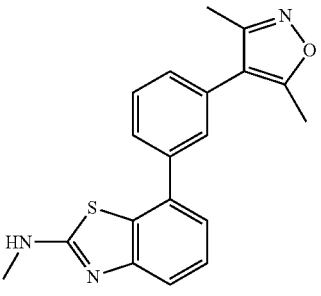 [SMILES: CNc1nc2cccc(-c3cccc(-c4c(C)noc4C)c3)c2s1] | NA | NA | | | | | | |
| 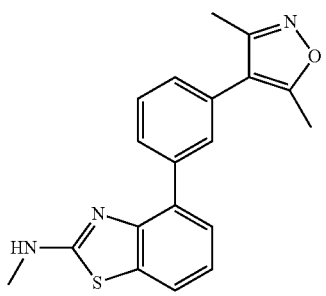 [SMILES: CNc1nc2c(-c3cccc(-c4c(C)noc4C)c3)cccc2s1] | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *[structure]* | NA | NA | | | | | | |
| *[structure]* | 2.86 | 4.65 | | | | | | |
| *[structure]* | NA | NA | | | | | | |
| *[structure]* | 0.22 | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 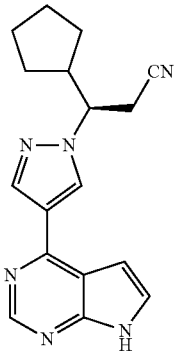 [SMILES: N#CC[C@H](C1CCCC1)n1cc(-c2ncnc3[nH]ccc23)cn1] | NA | 0.0013 | | | | | | |
| 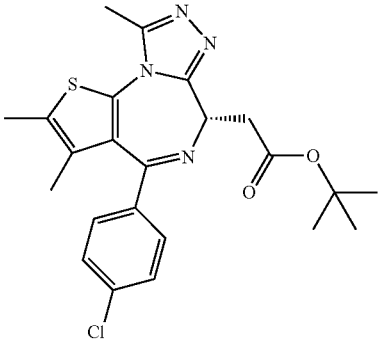 [SMILES: Cc1sc2c(c1C)C(c1ccc(Cl)cc1)=N[C@@H](CC(=O)OC(C)(C)C)c1nnc(C)n1-2] | 0.089 | NA | | | | | | |
| 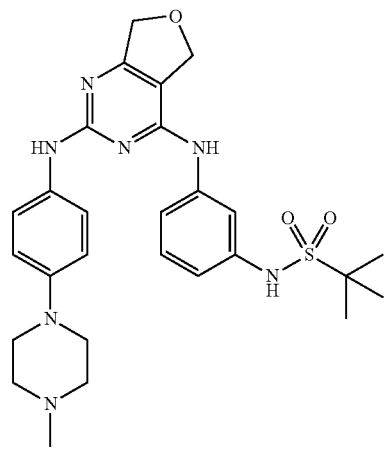 [SMILES: CN1CCN(c2ccc(Nc3nc4c(c(Nc5cccc(NS(=O)(=O)C(C)(C)C)c5)n3)COC4)cc2)CC1] | 0.526 | NA | | | | | | |
| 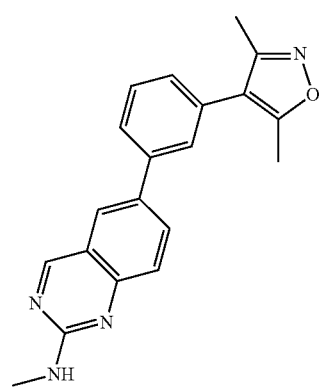 [SMILES: CNc1ncc2cc(-c3cccc(-c4c(C)noc4C)c3)ccc2n1] | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 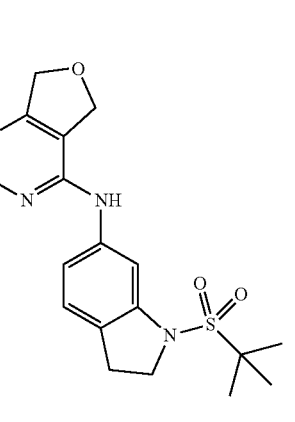 | 1.098 | NA | | | | | | |
| 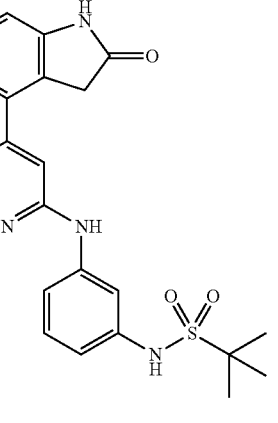 | 1.58 | NA | | | | | | |
| 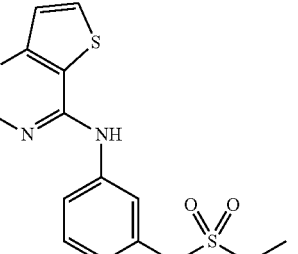 | NA | NA | | | | | | |
| 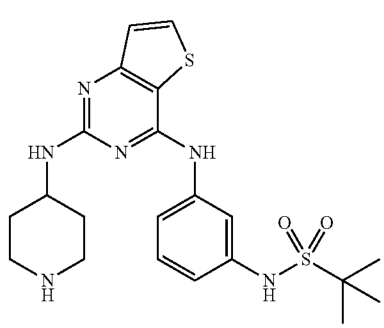 [SMILES: CC(C)(C)S(=O)(=O)Nc1cccc(Nc2nc(NC3CCNCC3)nc3ccsc23)c1] | 0.608 | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| [furo-pyrimidine with N-methylpiperidinyl-amino and phenyl-tert-butylsulfonamide] | 2.32 | NA | | | | | | |
| [thieno-pyrimidine with piperidinyl-amino and indoline-tert-butylsulfonyl] | NA | NA | | | | | | |
| [5-methylpyrimidine with 4-(N-methylpiperazinyl)phenyl-amino and phenyl-tert-butylsulfonamide] | 0.18 | 0.01 | | | | | | |
| [5-methylpyrimidine with 4-(N-methylpiperazinyl)phenyl-amino and pyrrole-N-cyclopropylcarboxamide] | NA | 0.030 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| | NA | NA | | | | | | |
| 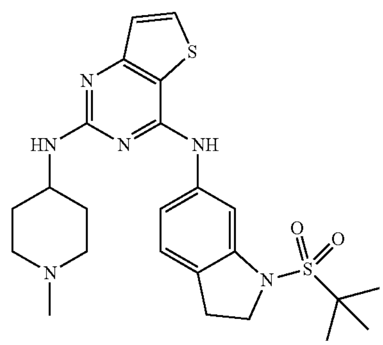 [SMILES: CN1CCC(Nc2nc(Nc3ccc4c(c3)N(S(=O)(=O)C(C)(C)C)CC4)c3sccc3n2)CC1] | 2.114 | NA | | | | | | |
| | NA | NA | | | | | | |
| | NA | NA | | | | | | |
| | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 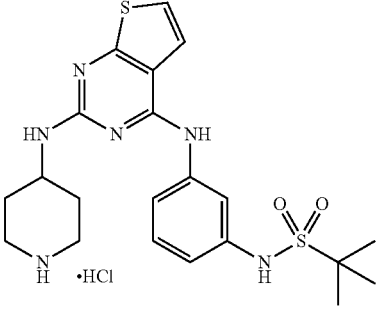 | 0.094 | NA | 0.309 | 0.458 | 0.248 | Data aw | | |
| 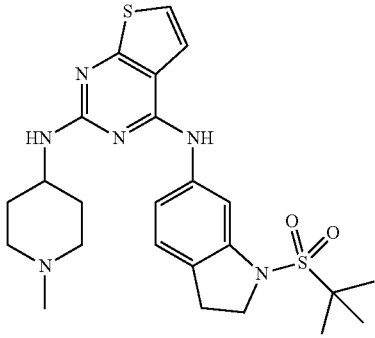 [SMILES: CN1CCC(Nc2nc(Nc3ccc4c(c3)N(S(=O)(=O)C(C)(C)C)CC4)c3ccsc3n2)CC1] | 0.16 | NA | 0.293 | 0.776 | 0.331 | Data aw | | |
| 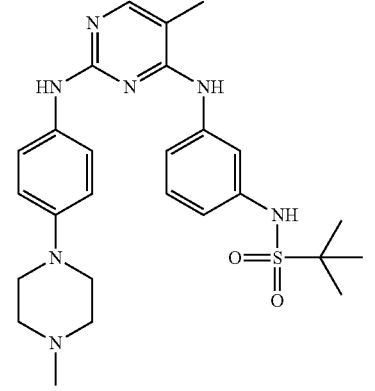 | 0.21 | 0.01 | 0.013 | 0.373 | 0.213 | Data aw | | |
| 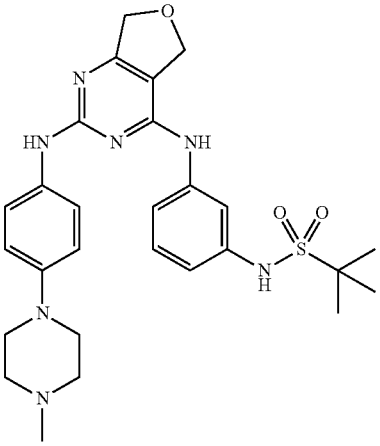 [SMILES: CN1CCN(c2ccc(Nc3nc4c(c(Nc5cccc(NS(=O)(=O)C(C)(C)C)c5)n3)COC4)cc2)CC1] | | | 1.005 | 1.77 | 2.47 | Data aw | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 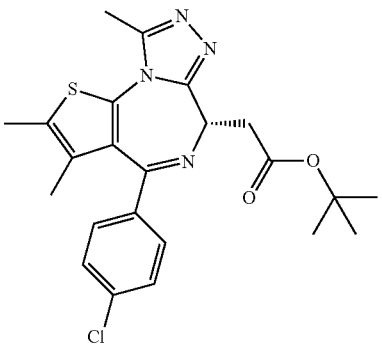 [SMILES: Cc1sc2c(c1C)C(c1ccc(Cl)cc1)=N[C@@H](CC(=O)OC(C)(C)C)c1nnc(C)n1-2] |  |  | 0.021 | 0.063 | 0.08 | Data aw |  |  |
| 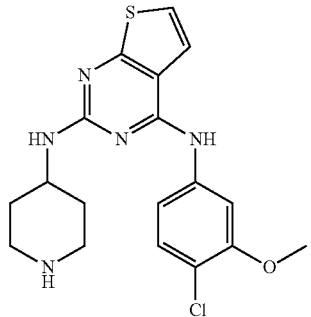 [SMILES: COc1cc(Nc2nc(NC3CCNCC3)nc3sccc23)ccc1Cl] | NA | NA |  |  |  |  |  |  |
| 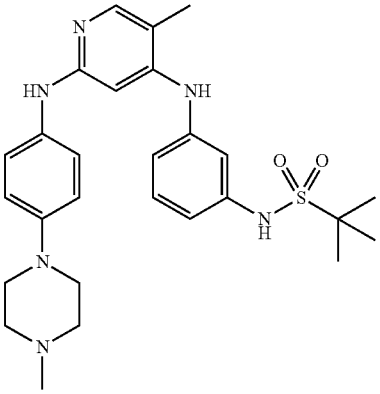 [SMILES: Cc1cnc(Nc2ccc(N3CCN(C)CC3)cc2)cc1Nc1cccc(NS(=O)(=O)C(C)(C)C)c1] | 6.31 | NA |  |  |  |  |  |  |
| 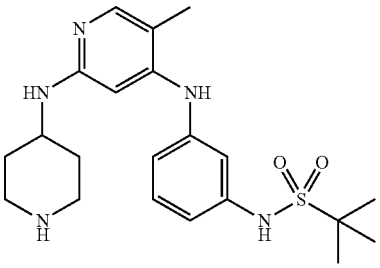 | NA | NA |  |  |  |  |  |  |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 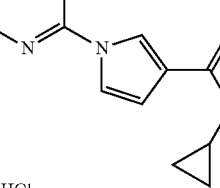 | NA | NA | | | | | | |
| 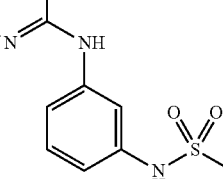 | NA | NA | | | | | | |
| 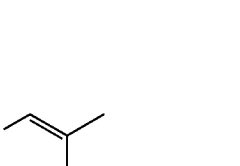 | 1.34 | NA | | | | | | |
| 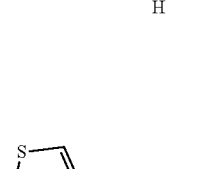 | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (thieno[3,2-d]pyrimidine with 3,3-difluorocyclobutylamino and tert-butylsulfonyl-indoline) | NA | NA | | | | | | |
| (thieno[3,2-d]pyrimidine with cyclohexylamino and tert-butylsulfonamido-phenyl) | NA | NA | | | | | | |
| (thieno[3,2-d]pyrimidine with pyrrolidin-3-ylamino and tert-butylsulfonyl-indoline) | 2.75 | NA | | | | | | |
| (thieno[3,2-d]pyrimidine with piperidin-4-ylmethylamino and tert-butylsulfonyl-indoline) | 2.17 | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| [structure] | NA | NA | | | | | | |
| [structure] | 2.67 | NA | | | | | | |
| [structure] | NA | NA | | | | | | |
| [structure] | 2.38 | NA | | | | | | |
| [structure] | NA | NA | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 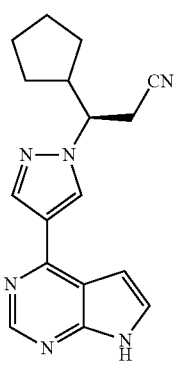 [SMILES: N#CC[C@H](C1CCCC1)n1cc(-c2ncnc3[nH]ccc23)cn1] | NA | 0.0031 | | | | | | |
| 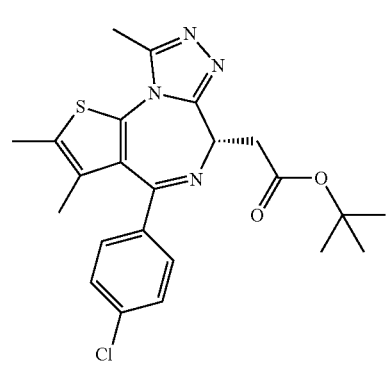 [SMILES: Cc1sc2c(c1C)C(c1ccc(Cl)cc1)=N[C@@H](CC(=O)OC(C)(C)C)c1nnc(C)n1-2] | 0.019 | NA | | | | | | |
| 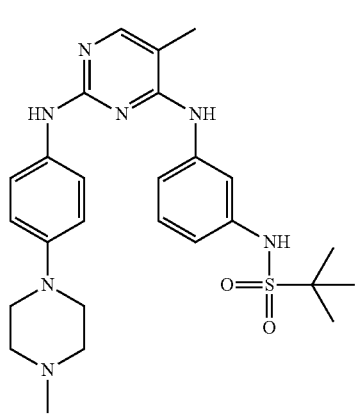 [SMILES: Cc1cnc(Nc2ccc(N3CCN(C)CC3)cc2)nc1Nc1cccc(NS(=O)(=O)C(C)(C)C)c1] | 0.221 | 0.007 | | | | | | |
| 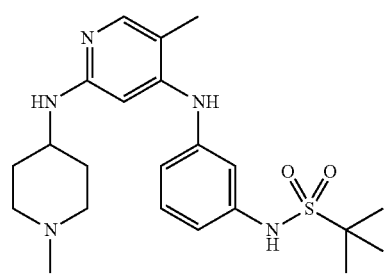 [SMILES: Cc1cnc(NC2CCN(C)CC2)cc1Nc1cccc(NS(=O)(=O)C(C)(C)C)c1] | NA | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | NA | NA | | | | | | |
| *structure* | 1.83 | NA | | | | | | |
| *structure* | 2.20 | NA | | | | | | |
| *structure* | 0.133 | 0.008 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 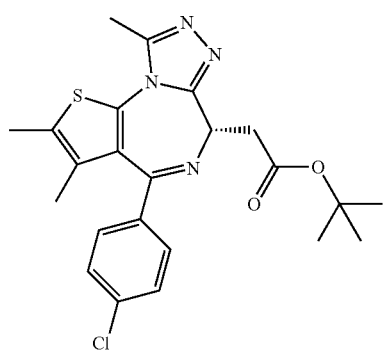 [SMILES: Cc1sc2c(c1C)C(c1ccc(Cl)cc1)=N[C@@H](CC(=O)OC(C)(C)C)c1nnc(C)n1-2] | 0.096 | NA | | | | | | |
| 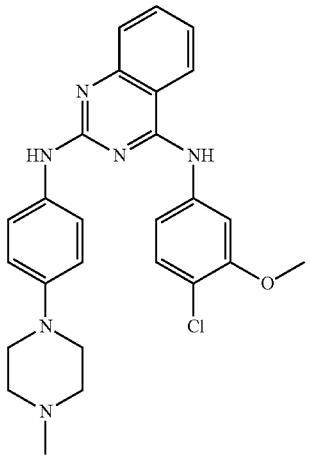 [SMILES: COc1cc(Nc2nc(Nc3ccc(N4CCN(C)CC4)cc3)nc3ccccc23)ccc1Cl] | NA | NA | | | | | | |
| 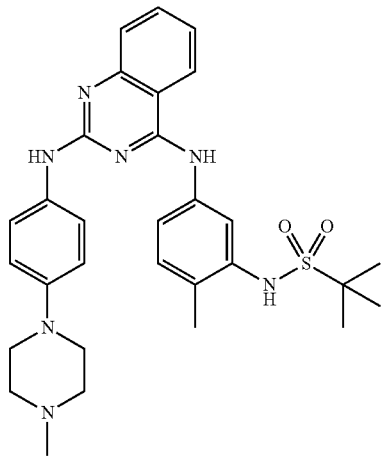 [SMILES: Cc1ccc(Nc2nc(Nc3ccc(N4CCN(C)CC4)cc3)nc3ccccc23)cc1NS(=O)(=O)C(C)(C)C] | 0.47 | NA | 1.13 | 0.636 | 3.2 | 1.8 | NA | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| [structure] | 0.155 | 0.012 | | | | | | |
| [structure] | 0.087 | 0.024 | 0.030 | 0.157 | 0.092 | 0.131 | 1.01 | |
| [structure] | 0.194 | NA | | | | | | |
| [structure] | 3.20 | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 0.581 | 0.0018 | | | | | | |
| *structure* | 0.318 | NA | | | | | | |
| *structure* | 0.206 | NA | | | | | | |
| *structure* | 7.50 | NA | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 0.066 | NA | | | | | | |
| *structure* | 0.42 | 0.0023 | 0.451 | 0.682 | 0.853 | 0.638 | | 0.185 |
| *structure* | 0.118 | 0.004 | 0.073 | 0.448 | 0.366 | 0.23 | | |
| *structure* | 0.0934 | 0.0118 | 0.112 | 0.254 | 0.183 | 0.228 | | 0.313 |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 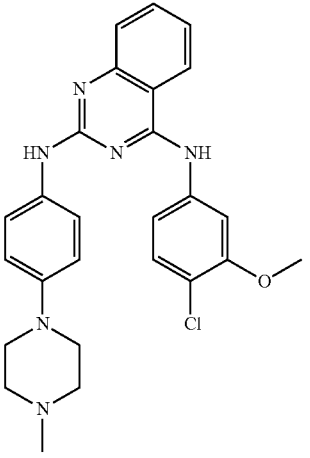 [SMILES: COc1cc(Nc2nc(Nc3ccc(N4CCN(C)CC4)cc3)nc3ccccc23)ccc1Cl] | 6.30 | NA | 5.3 | 0.79 | 8.4 | NA | | NA |
| 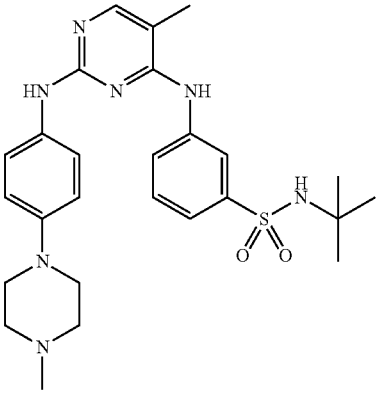 [SMILES: Cc1cnc(Nc2ccc(N3CCN(C)CC3)cc2)nc1Nc1cccc(S(=O)(=O)NC(C)(C)C)c1] | 0.79 | 0.0014 | 0.736 | 0.678 | 1.4 | 1.4 | | 0.220 |
| 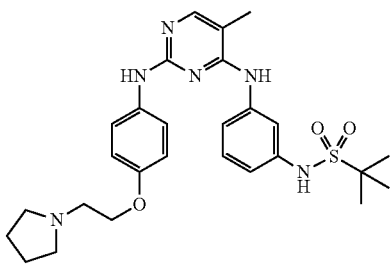 [SMILES: Cc1cnc(Nc2ccc(OCCN3CCCC3)cc2)nc1Nc1cccc(NS(=O)(=O)C(C)(C)C)c1] | 0.42 | 0.0023 | | | | | | |
| 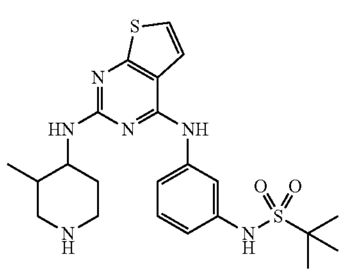 [SMILES: CC1CNCCC1Nc1nc(Nc2cccc(NS(=O)(=O)C(C)(C)C)c2)c2ccsc2n1] | 1.98 | 10 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 2.83 | 10 | | | | | | |
| *structure* | 5.80 | 10 | | | | | | |
| *structure* | 3.27 | 10 | | | | | | |
| *structure* | 2.68 | 10 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 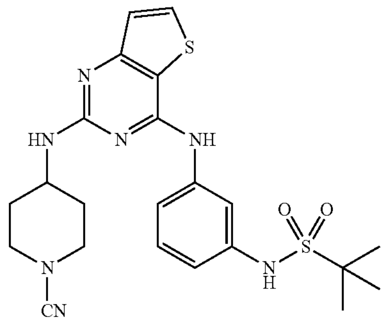 [SMILES: CC(C)(C)S(=O)(=O)Nc1cccc(Nc2nc(NC3CCN(C#N)CC3)nc3ccsc23)c1] | 10 | 10 | | | | | | |
| 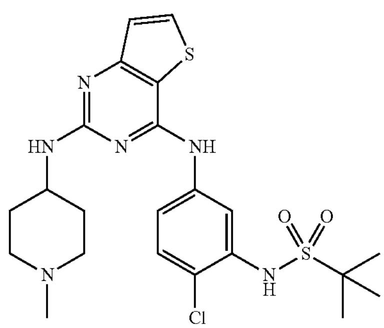 [SMILES: CN1CCC(Nc2nc(Nc3ccc(Cl)c(NS(=O)(=O)C(C)(C)C)c3)c3sccc3n2)CC1] | 0.90 | 10 | | | | | | |
| 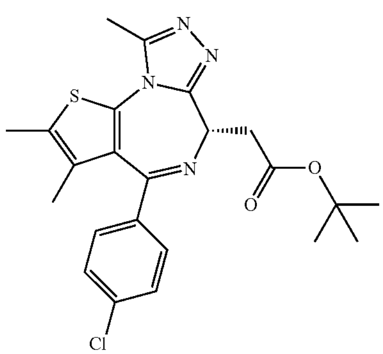 [SMILES: Cc1sc2c(c1C)C(c1ccc(Cl)cc1)=N[C@@H](CC(=O)OC(C)(C)C)c1nnc(C)n1-2] | 0.17 | 10 | | | | | | |
| 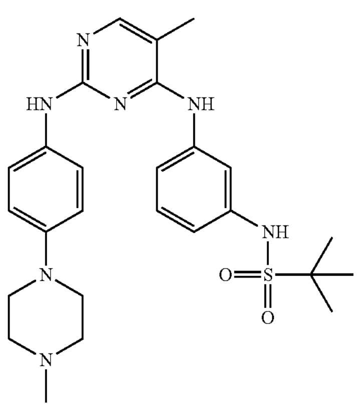 [SMILES: Cc1cnc(Nc2ccc(N3CCN(C)CC3)cc2)nc1Nc1cccc(NS(=O)(=O)C(C)(C)C)c1] | 0.255 | 0.01 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 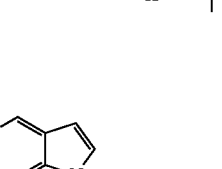 | 10 | 10 | | | | | | |
| 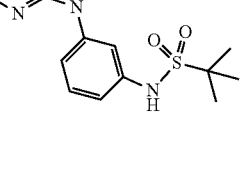 | 0.22 | 0.0074 | 0.175 | 0.70 | 0.27 | 0.696 | 0.243 | 0.127 |
| 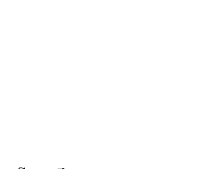 | 10 | 10 | | | | | | |
| 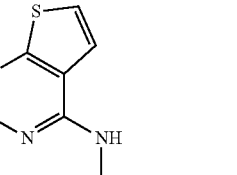 | 3.03 | 10 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 0.87 | 10 | | | | | | |
| *structure* | 0.18 | 8.93 | | | | | | |
| *structure* | 10 | 10 | | | | | | |
| *structure* | 0.94 | 10 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure) | 0.59 | 10 | | | | | | |
| (structure) | 1.542 | 10 | | | | | | |
| (structure) | 5.156 | 10 | | | | | | |
| (structure) | 0.257 | 10 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *[structure]* | 0.22 | 0.007 | 0.073 | 0.448 | 0.366 | 0.23 | | NA |
| *[structure]* | 1.21 | 10 | | | | | | |
| *[structure]* | 1.68 | 0.032 | | | | | | |
| *[structure]* · HCl | 0.122 | 3.01 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 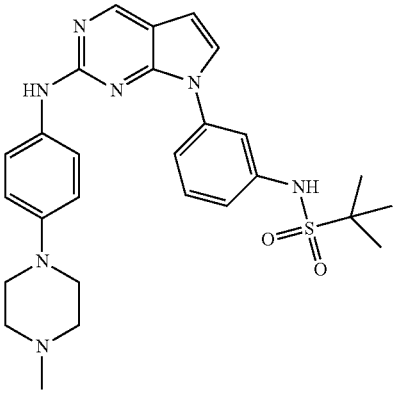 [SMILES: CN1CCN(c2ccc(Nc3ncc4ccn(-c5cccc(NS(=O)(=O)C(C)(C)C)c5)c4n3)cc2)CC1] | 0.242 | 0.0058 | | | | | | |
| 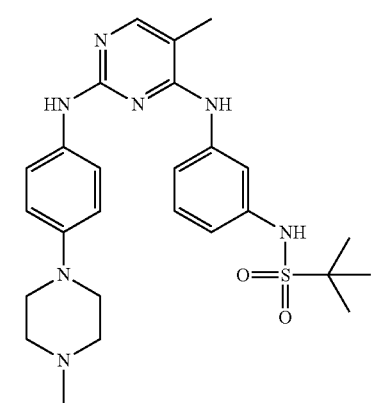 | 0.164 | 0.008 | | | | | | |
| 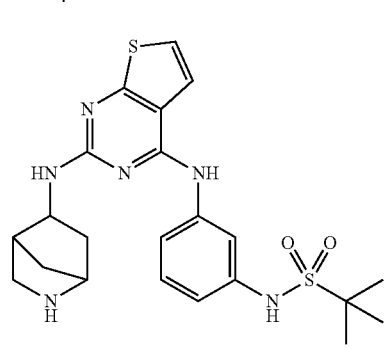 | 0.26 | 4.17 | | | | | | |
| 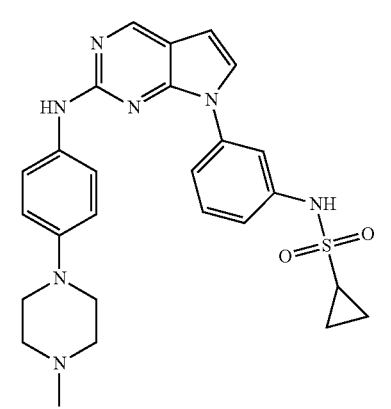 [SMILES: CN1CCN(c2ccc(Nc3ncc4ccn(-c5cccc(NS(=O)(=O)C6CC6)c5)c4n3)cc2)CC1] | 0.355 | 0.0025 | 0.729 | 1.9 | 0.825 | 2.5 | 0.244 | 0.069 |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 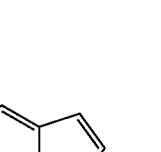 | 1.41 | 0.032 | | | | | | |
| 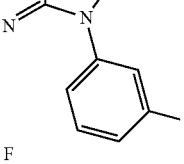 | 0.434 | 0.018 | 0.487 | 2.86 | 0.652 | 1.11 | 0.424 | 0.125 |
| 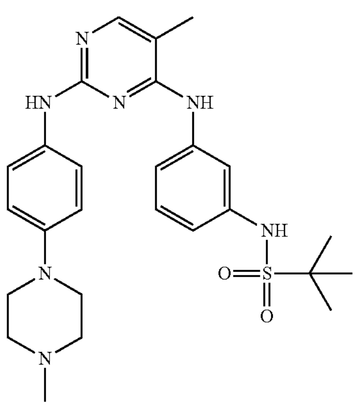 [SMILES: Cc1cnc(Nc2ccc(N3CCN(C)CC3)cc2)nc1Nc1cccc(NS(=O)(=O)C(C)(C)C)c1] | 0.228 | 0.010 | | | | | | |
| 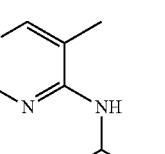 | 1.02 | 0.0082 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 0.152 | 0.012 | 0.254 | 1.58 | 0.5 | 0.632 | 0.418 | 0.067 |
| *structure* | 10 | 10 | | | | | | |
| *structure* | 2.33 | 0.003 | | | | | | |
| *structure* | 1.30 | 0.038 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| | 10 | 0.003 | | | | | | |
| 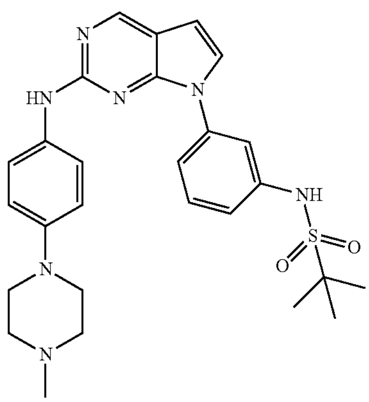 [SMILES: CN1CCN(c2ccc(Nc3ncc4ccn(-c5cccc(NS(=O)(=O)C(C)(C)C)c5)c4n3)cc2)CC1] | 5.01 | 1.66 | | | | | | |
| 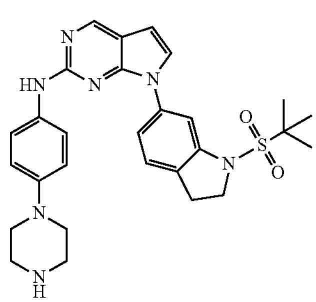 [SMILES: CC(C)(C)S(=O)(=O)N1CCc2ccc(-n3ccc4cnc(Nc5ccc(N6CCNCC6)cc5)nc43)cc21] | 1.94 | 0.04 | | | | | | |
| | 10 | 10 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *(structure)* | 1.13 | 0.008 | | | | | | |
| *(structure)* | 0.28 | 0.009 | | | | | | |
| *(structure)* | 10 | 10 | | | | | | |
| *(structure)* | 0.284 | 1000 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 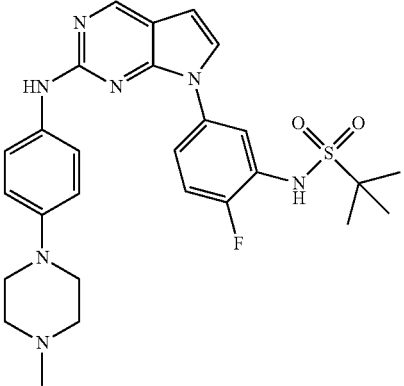 [SMILES: CN1CCN(c2ccc(Nc3ncc4ccn(-c5ccc(F)c(NS(=O)(=O)C(C)(C)C)c5)c4n3)cc2)CC1] | 0.128 | 0.035 | 0.0675 | 0.49 | 0.109 | 0.182 | 0.972 | 0.105 |
| 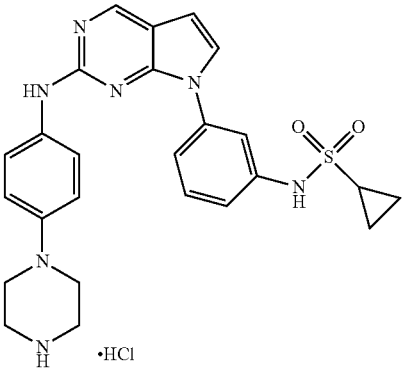 [SMILES: O=S(=O)(Nc1cccc(-n2ccc3cnc(Nc4ccc(N5CCNCC5)cc4)nc32)c1)C1CC1 ; Cl] | 0.677 | 0.002 | 0.574 | 2.961 | 0.914 | 1.21 | 0.188 | 0.015 |
| 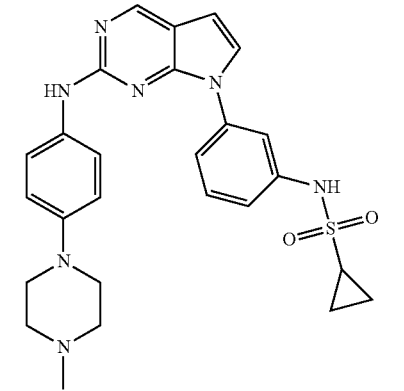 [SMILES: CN1CCN(c2ccc(Nc3ncc4ccn(-c5cccc(NS(=O)(=O)C6CC6)c5)c4n3)cc2)CC1] | 1.46 | 0.0043 | 1.349 | 6.207 | 1.735 | 2.633 | | 0.031 |
| 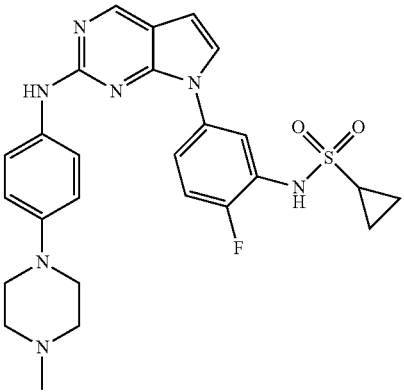 [SMILES: CN1CCN(c2ccc(Nc3ncc4ccn(-c5ccc(Cl)c(NS(=O)(=O)C6CC6)c5)c4n3)cc2)CC1] | 1.49 | 0.0153 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 3.055 | 0.0197 | | | | | | |
| *structure* | 1.043 | 0.0143 | | | | | | |
| *structure* | 5.529 | 0.0244 | | | | | | |
| *structure* | 0.68 | 0.23 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure 1) | 0.641 | 0.176 | | | | | | |
| (structure 2) | 0.24 | 0.0115 | 0.156 | 0.314 | 0.089 | 0.23 | 0.057 | 0.103 |
| (structure 3) | 0.676 | 0.0204 | 0.325 | 1.4 | 0.57 | 0.322 | 0.473 | 0.1 |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 0.394 | 0.01 | | | | | | |
| *structure* | 1.353 | 0.005 | | | | | | |
| *structure* | 0.208 | 0.101 | | | | | | |
| *structure* | 2.2 | 0.031 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 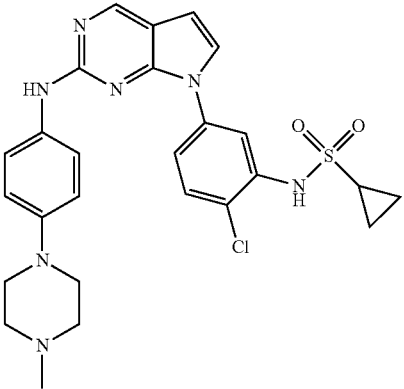 | 1.70 | 0.043 | | | | | | |
| 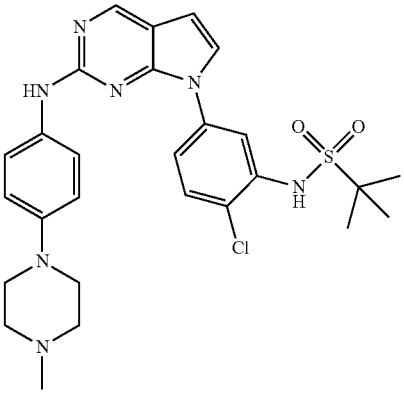 [SMILES: CN1CCN(c2ccc(Nc3ncc4ccn(-c5ccc(Cl)c(NS(=O)(=O)C(C)(C)C)c5)c4n3)cc2)CC1] | 0.481 | 0.165 | | | | | | |
| 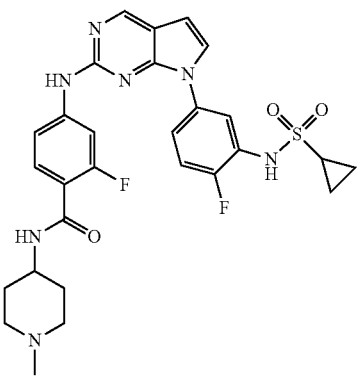 [SMILES: CN1CCC(NC(=O)c2ccc(Nc3ncc4ccn(-c5ccc(F)c(NS(=O)(=O)C6CC6)c5)c4n3)cc2F)CC1] | 0.776 | 0.035 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 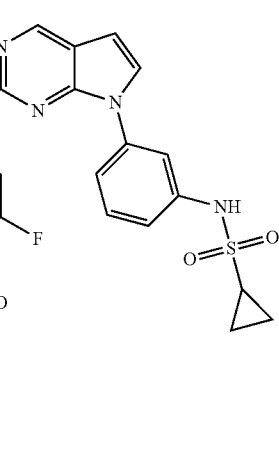 | 0.856 | 0.013 | | | | | | |
| 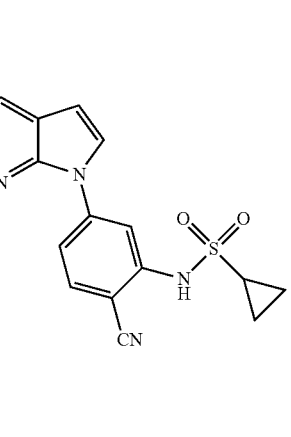 | 1.8 | 0.078 | | | | | | |
| 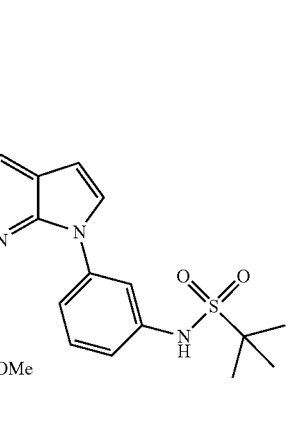 | 0.431 | 0.0052 | 0.13 | 0.743 | 0.161 | 0.363 | 0.293 | 0.082 |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 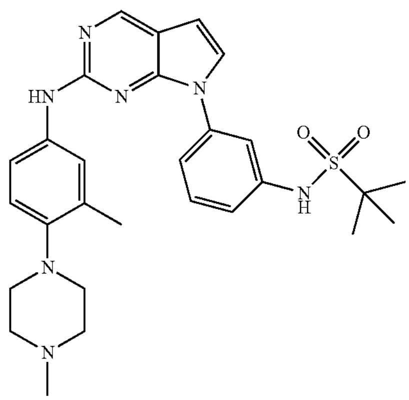 [SMILES: Cc1cc(Nc2ncc3ccn(-c4cccc(NS(=O)(=O)C(C)(C)C)c4)c3n2)ccc1N1CCN(C)CC1] | 0.722 | 0.011 | | | | | | |
| 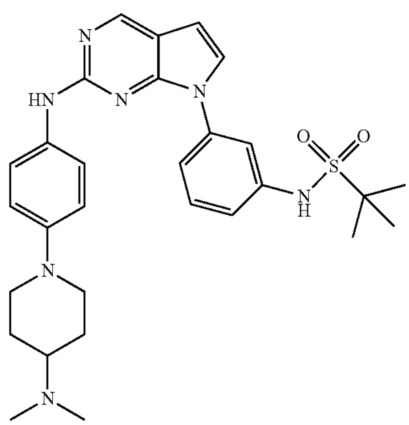 [SMILES: CN(C)C1CCN(c2ccc(Nc3ncc4ccn(-c5cccc(NS(=O)(=O)C(C)(C)C)c5)c4n3)cc2)CC1] | 0.173 | 0.0073 | 0.062 | 0.632 | 0.164 | 0.406 | 0.4 | 0.081 |
| 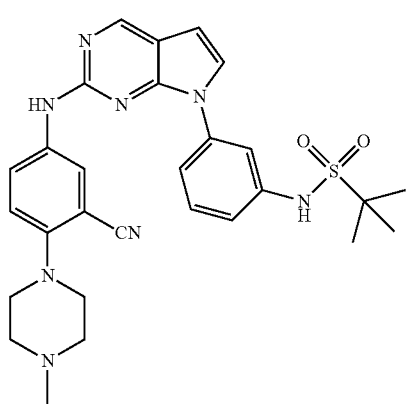 [SMILES: CN1CCN(c2ccc(Nc3ncc4ccn(-c5cccc(NS(=O)(=O)C(C)(C)C)c5)c4n3)cc2C#N)CC1] | 0.378 | 0.0189 | 0.491 | 1.15 | 0.248 | 1 | 1.1 | 0.338 |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 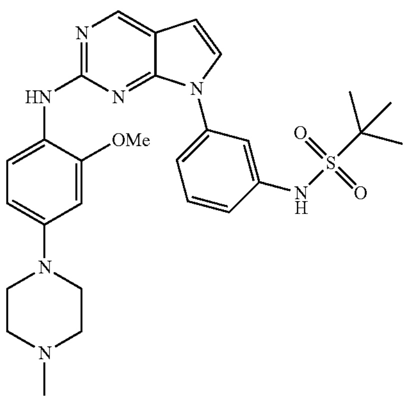 [SMILES: COc1cc(N2CCN(C)CC2)ccc1Nc1ncc2ccn(-c3cccc(NS(=O)(=O)C(C)(C)C)c3)c2n1] | 1.6 | 2.8 | | | | | | |
| 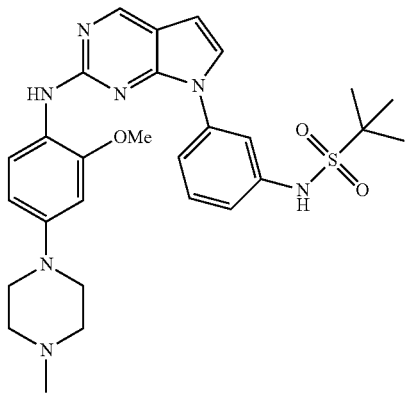 | 0.451 | 0.006 | | | | | | |
| 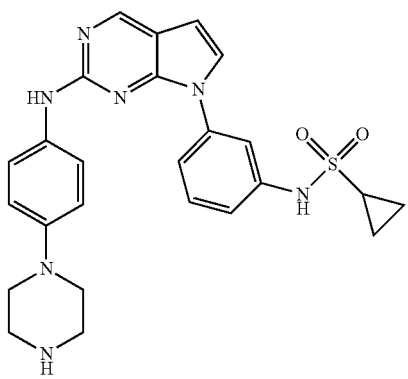 | 0.166 | 0.013 | | | | | | |
| 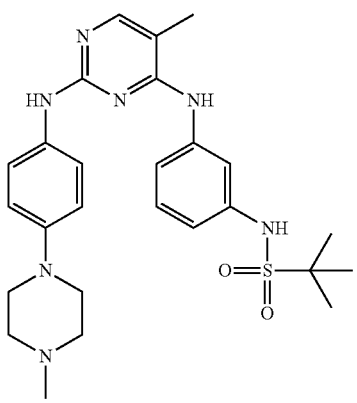 [SMILES: Cc1cnc(Nc2ccc(N3CCN(C)CC3)cc2)nc1Nc1cccc(NS(=O)(=O)C(C)(C)C)c1] | | | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 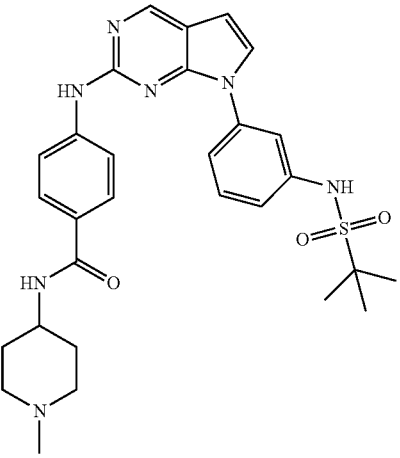 [SMILES: CN1CCC(NC(=O)c2ccc(Nc3ncc4ccn(-c5cccc(NS(=O)(=O)C(C)(C)C)c5)c4n3)cc2)CC1] | 0.407 | 0.026 | | | | | | |
| 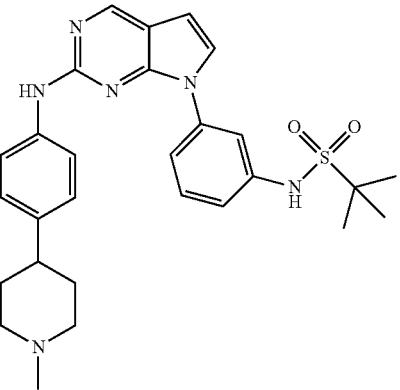 [SMILES: CN1CCC(c2ccc(Nc3ncc4ccn(-c5cccc(NS(=O)(=O)C(C)(C)C)c5)c4n3)cc2)CC1] | 0.581 | 0.074 | | | | | | |
| 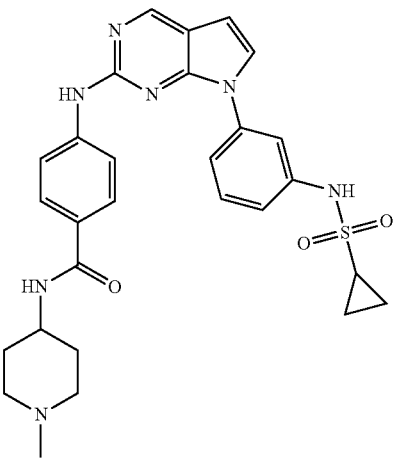 [SMILES: CN1CCC(NC(=O)c2ccc(Nc3ncc4ccn(-c5cccc(NS(=O)(=O)C6CC6)c5)c4n3)cc2)CC1] | 1.9 | 0.044 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 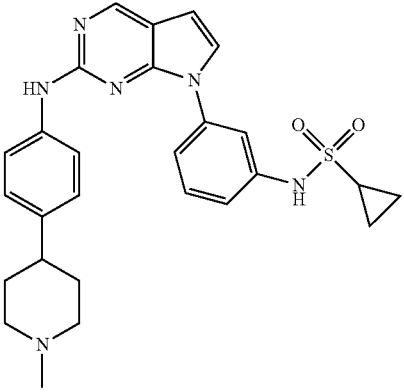 [SMILES: CN1CCC(c2ccc(Nc3ncc4ccn(-c5cccc(NS(=O)(=O)C6CC6)c5)c4n3)cc2)CC1] | 2.72 | 0.051 | | | | | | |
| 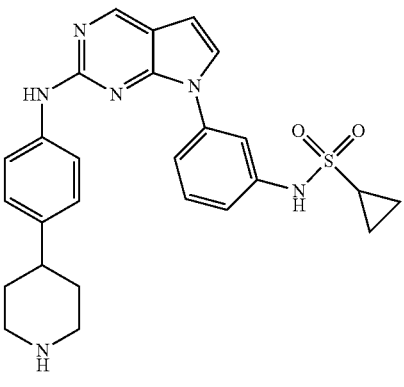 [SMILES: O=S(=O)(Nc1cccc(-n2ccc3cnc(Nc4ccc(C5CCNCC5)cc4)nc32)c1)C1CC1] | 3.21 | 0.071 | | | | | | |
| 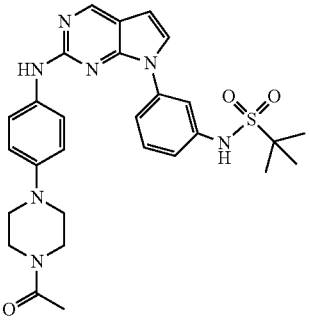 [SMILES: CC(=O)N1CCN(c2ccc(Nc3ncc4ccn(-c5cccc(NS(=O)(=O)C(C)(C)C)c5)c4n3)cc2)CC1] | 2..5 | 0.045 | | | | | | |
| 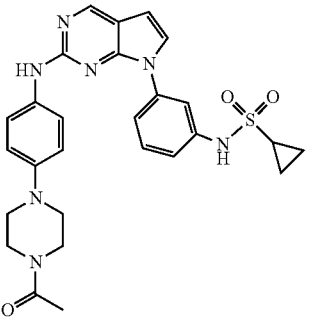 [SMILES: CC(=O)N1CCN(c2ccc(Nc3ncc4ccn(-c5cccc(NS(=O)(=O)C6CC6)c5)c4n3)cc2)CC1] | 5.73 | 24.94 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 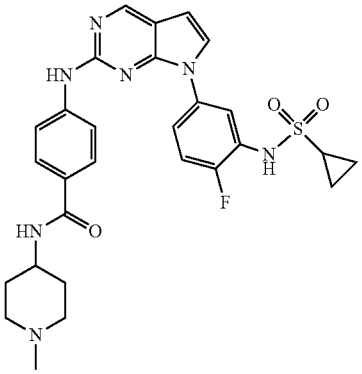 [SMILES: CN1CCC(NC(=O)c2ccc(Nc3ncc4ccn(-c5ccc(F)c(NS(=O)(=O)C6CC6)c5)c4n3)cc2)CC1] | 1.13 | 0.152 | | | | | | |
| 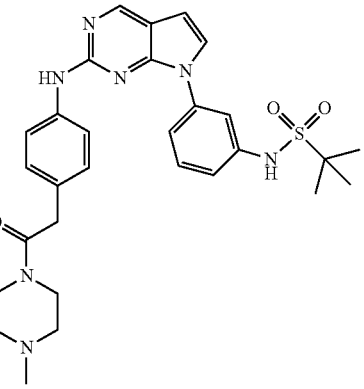 | 0.916 | 0.176 | | | | | | |
| 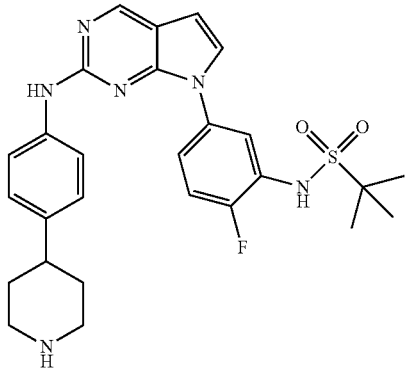 [SMILES: CC(C)(C)S(=O)(=O)Nc1cc(-n2ccc3cnc(Nc4ccc(C5CCNCC5)cc4)nc32)ccc1F] | 0.475 | 1.601 | | | | | | |
| 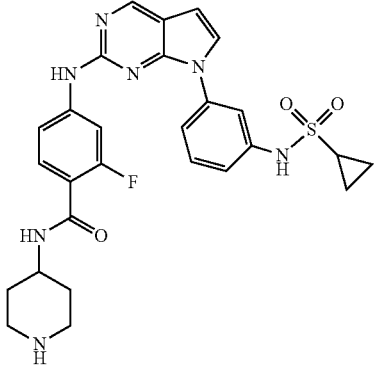 [SMILES: O=C(NC1CCNCC1)c1ccc(Nc2ncc3ccn(-c4cccc(NS(=O)(=O)C5CC5)c4)c3n2)cc1F] | 1.59 | 0.069 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 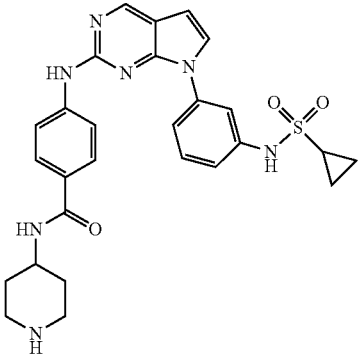 [SMILES: O=C(NC1CCNCC1)c1ccc(Nc2ncc3ccn(-c4cccc(NS(=O)(=O)C5CC5)c4)c3n2)cc1] | 2.1 | 0.04 | | | | | | |
| 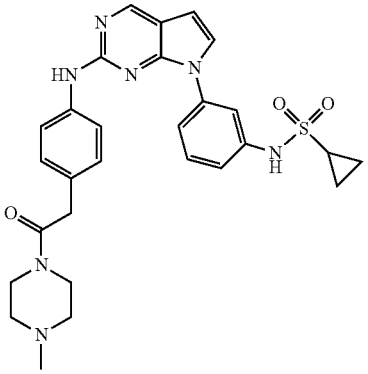 [SMILES: CN1CCN(C(=O)Cc2ccc(Nc3ncc4ccn(-c5cccc(NS(=O)(=O)C6CC6)c5)c4n3)cc2)CC1] | 4.01 | 0.182 | | | | | | |
| 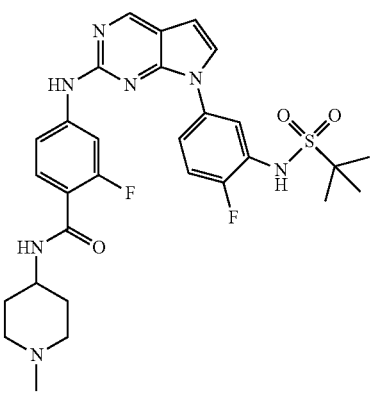 [SMILES: CN1CCC(NC(=O)c2ccc(Nc3ncc4ccn(-c5ccc(F)c(NS(=O)(=O)C(C)(C)C)c5)c4n3)cc2F)CC1] | 0.094 | 359.7 | | | | | | |
| 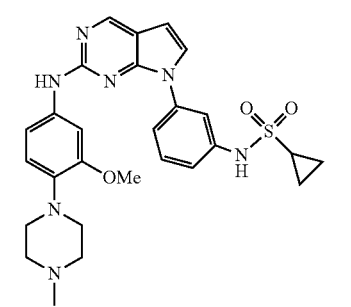 [SMILES: COc1cc(Nc2ncc3ccn(-c4cccc(NS(=O)(=O)C5CC5)c4)c3n2)ccc1N1CCN(C)CC1] | 1.81 | 0.015 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *(structure)* | 10 | 0.008 | | | | | | |
| *(structure)* | 0.866 | 0.014 | | | | | | |
| *(structure)* | 0.235 | 0.043 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *structure* | 0.228 | 0.188 | | | | | | |
| *structure* | 7.075 | 10 | | | | | | |
| *structure* | 10 | 0.011 | | | | | | |
| *structure* | 0.398 | 0.018 | 0.099 | 0.467 | 0.078 | 0.312 | 0.206 | 0.242 |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 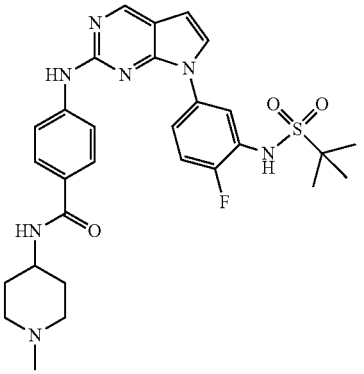 [SMILES: CN1CCC(NC(=O)c2ccc(Nc3ncc4ccn(-c5ccc(F)c(NS(=O)(=O)C(C)(C)C)c5)c4n3)cc2)CC1] | 0.372 | 0.177 | | | | | | |
| 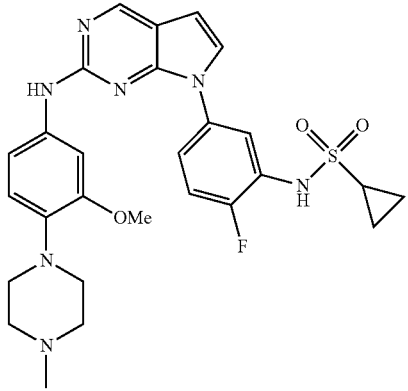 [SMILES: COc1cc(Nc2ncc3ccn(-c4ccc(F)c(NS(=O)(=O)C5CC5)c4)c3n2)ccc1N1CCN(C)CC1] | 0.989 | 0.029 | | | | | | |
| 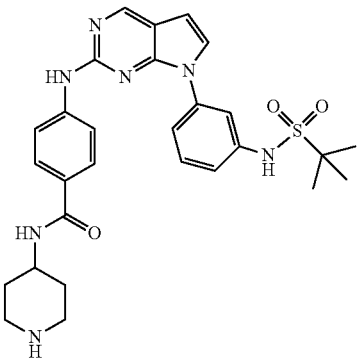 [SMILES: CC(C)(C)S(=O)(=O)Nc1cccc(-n2ccc3cnc(Nc4ccc(C(=O)NC5CCNCC5)cc4)nc32)c1] | 0.649 | 0.024 | | | | | | |
| 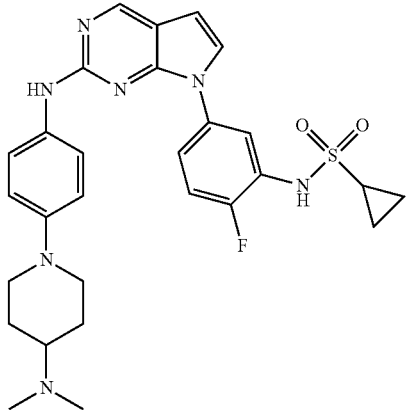 [SMILES: CN(C)C1CCN(c2ccc(Nc3ncc4ccn(-c5ccc(F)c(NS(=O)(=O)C6CC6)c5)c4n3)cc2)CC1] | 1.01 | 0.01 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 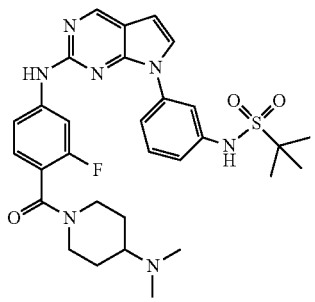 [SMILES: CN(C)C1CCN(C(=O)c2ccc(Nc3ncc4ccn(-c5cccc(NS(=O)(=O)C(C)(C)C)c5)c4n3)cc2F)CC1] | 0.246 | 0.02 | 0.029 | 0.318 | 0.117 | 0.189 | 1.1 | 0.292 |
| 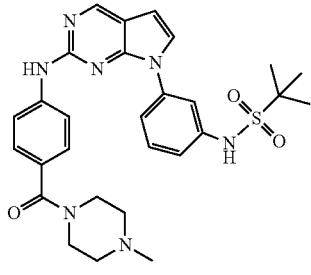 [SMILES: CN1CCN(C(=O)c2ccc(Nc3ncc4ccn(-c5cccc(NS(=O)(=O)C(C)(C)C)c5)c4n3)cc2)CC1] | 0.771 | 0.028 | | | | | | |
| 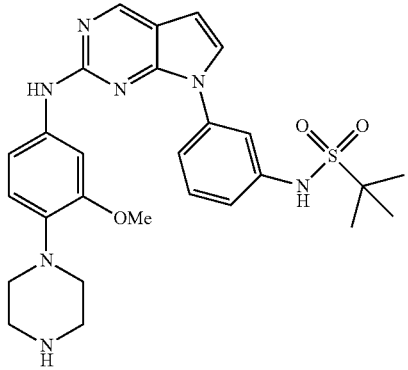 [SMILES: COc1cc(Nc2ncc3ccn(-c4cccc(NS(=O)(=O)C(C)(C)C)c4)c3n2)ccc1N1CCNCC1] | 0.402 | 0.0028 | 0.128 | 0.548 | 0.142 | 0.32 | 0.275 | 0.112 |
| 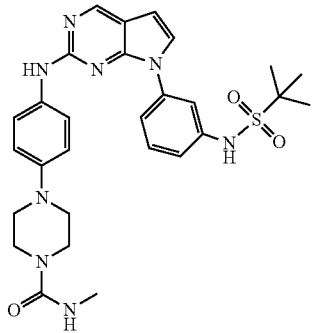 [SMILES: CNC(=O)N1CCN(c2ccc(Nc3ncc4ccn(-c5cccc(NS(=O)(=O)C(C)(C)C)c5)c4n3)cc2)CC1] | 3.2 | 0.019 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 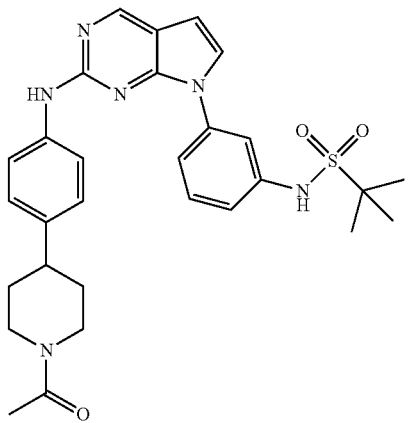 [SMILES: CC(=O)N1CCC(c2ccc(Nc3ncc4ccn(-c5cccc(NS(=O)(=O)C(C)(C)C)c5)c4n3)cc2)CC1] | | 10 | 0.456 | | | | | |
| 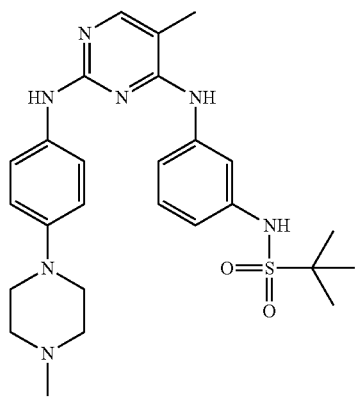 [SMILES: Cc1cnc(Nc2ccc(N3CCN(C)CC3)cc2)nc1Nc1cccc(NS(=O)(=O)C(C)(C)C)c1] | | 0.278 | 0.0066 | | | | | |
| 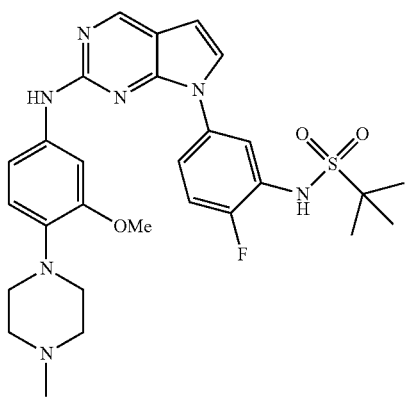 [SMILES: COc1cc(Nc2ncc3ccn(-c4ccc(F)c(NS(=O)(=O)C(C)(C)C)c4)c3n2)ccc1N1CCN(C)CC1] | | 0.272 | 0.09 | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *[structure]* | 10 | 0.14 | | | | | | |
| *[structure]* | 1.8 | 0.008 | | | | | | |
| *[structure]* | 0.774 | 10 | | | | | | |
| *[structure]* | 1.7 | 0.074 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 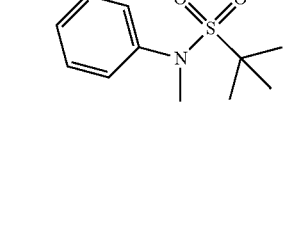 | 1.1 | 0.009 | | | | | | |
| 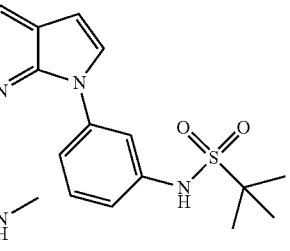 | 0.561 | 0.022 | | | | | | |
| 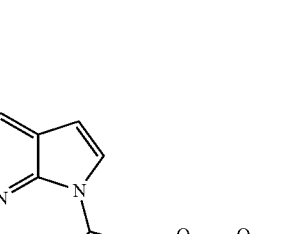 | 0.258 | 0.082 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 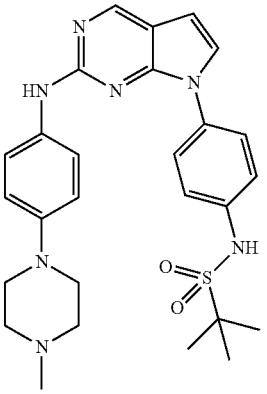 [SMILES: CN1CCN(c2ccc(Nc3ncc4ccn(-c5ccc(NS(=O)(=O)C(C)(C)C)cc5)c4n3)cc2)CC1] | 10 | 0.0007 | | | | | | |
| 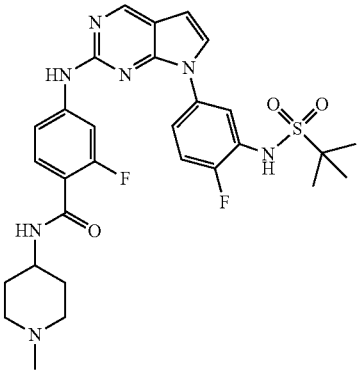 [SMILES: CN1CCC(NC(=O)c2ccc(Nc3ncc4ccn(-c5ccc(F)c(NS(=O)(=O)C(C)(C)C)c5)c4n3)cc2F)CC1] | 0.134 | 0.13 | | | | | | |
| 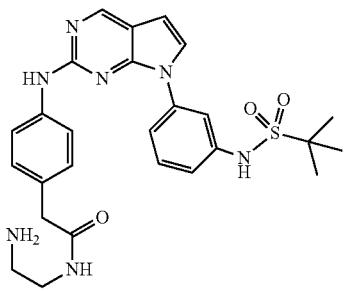 [SMILES: CC(C)(C)S(=O)(=O)Nc1cccc(-n2ccc3cnc(Nc4ccc(CC(=O)NCCN)cc4)nc32)c1] | 0.406 | 0.064 | | | | | | |
| 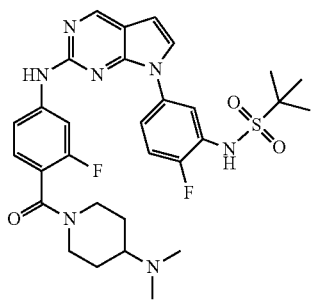 [SMILES: CN(C)C1CCN(C(=O)c2ccc(Nc3ncc4ccn(-c5ccc(F)c(NS(=O)(=O)C(C)(C)C)c5)c4n3)cc2F)CC1] | 0.123 | 0.17 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 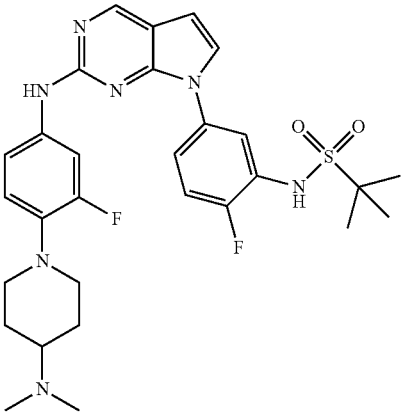 [SMILES: CN(C)C1CCN(c2ccc(Nc3ncc4ccn(-c5ccc(F)c(NS(=O)(=O)C(C)(C)C)c5)c4n3)cc2F)CC1] | 0.063 | 0.027 | 0.088 | 0.231 | 0.049 | 0.14 | 2.1 | 0.193 |
| 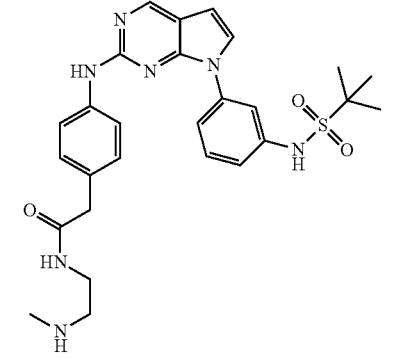 [SMILES: CNCCNC(=O)Cc1ccc(Nc2ncc3ccn(-c4cccc(NS(=O)(=O)C(C)(C)C)c4)c3n2)cc1] | 0.205 | 0.05 | 0.067 | 0.576 | 0.117 | 0.268 | 0.178 | 0.253 |
| 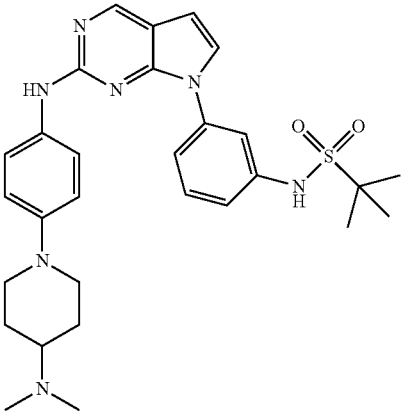 [SMILES: CN(C)C1CCN(c2ccc(Nc3ncc4ccn(-c5cccc(NS(=O)(=O)C(C)(C)C)c5)c4n3)cc2)CC1] | 0.19 | 0.005 | | | | | | |
| 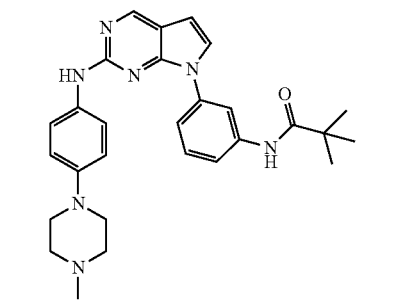 [SMILES: CN1CCN(c2ccc(Nc3ncc4ccn(-c5cccc(NC(=O)C(C)(C)C)c5)c4n3)cc2)CC1] | 10 | 0.054 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 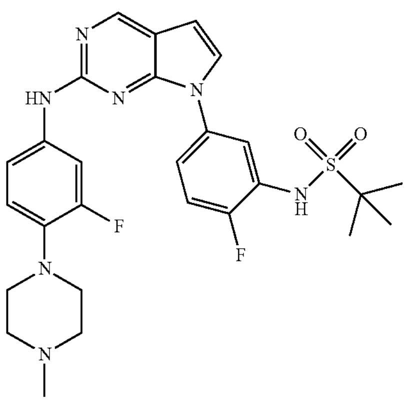 [SMILES: CN1CCN(c2ccc(Nc3ncc4ccn(-c5ccc(F)c(NS(=O)(=O)C(C)(C)C)c5)c4n3)cc2F)CC1] | 0.149 | 0.062 | | | | | | |
| 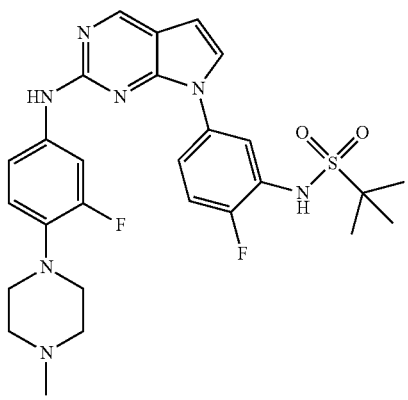 | 0.131 | 0.003 | | | | | | |
| 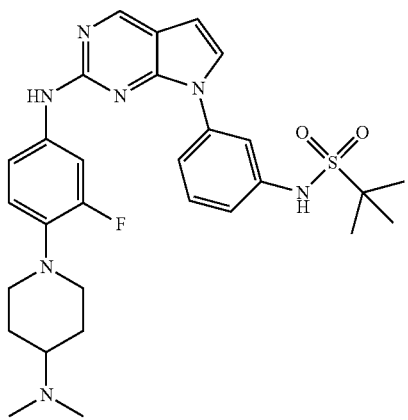 [SMILES: CN(C)C1CCN(c2ccc(Nc3ncc4ccn(-c5cccc(NS(=O)(=O)C(C)(C)C)c5)c4n3)cc2F)CC1] | 0.682 | 0.02 | | | | | | |
| 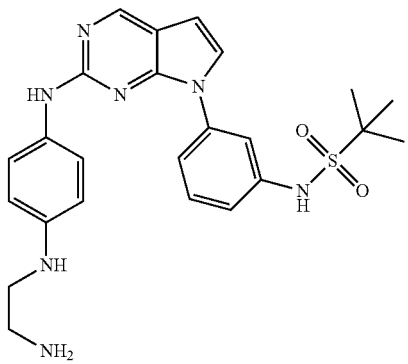 [SMILES: CC(C)(C)S(=O)(=O)Nc1cccc(-n2ccc3cnc(Nc4ccc(NCCN)cc4)nc32)c1] | | | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 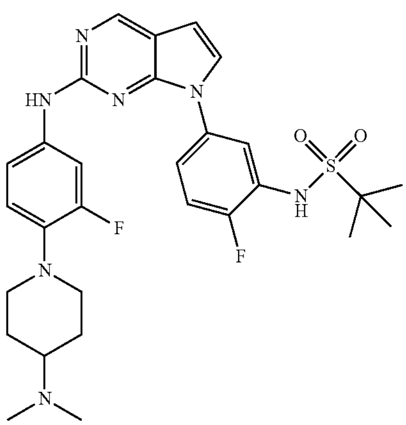 [SMILES: CN(C)C1CCN(c2ccc(Nc3ncc4ccn(-c5ccc(F)c(NS(=O)(=O)C(C)(C)C)c5)c4n3)cc2F)CC1] | 0.153 | 0.027 | | | | | | |
| 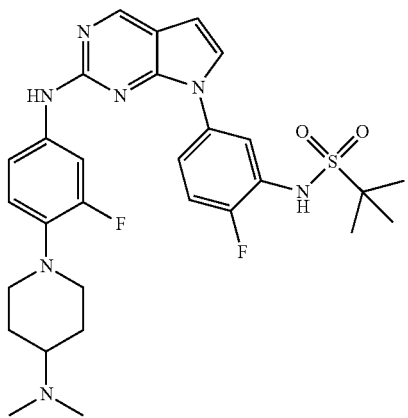 | 0.407 | 0.024 | | | | | | |
| 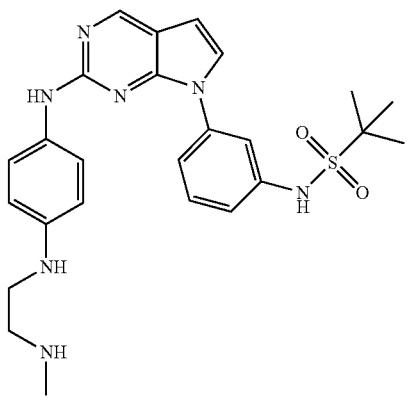 [SMILES: CNCCNc1ccc(Nc2ncc3ccn(-c4cccc(NS(=O)(=O)C(C)(C)C)c4)c3n2)cc1] | 0.316 | 0.0093 | | | | | | |
| 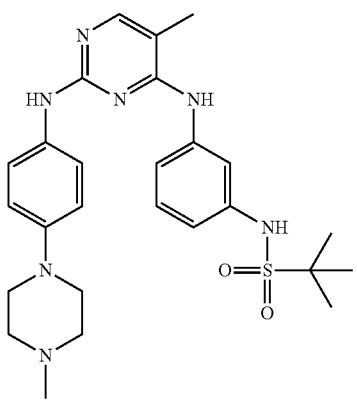 | | | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 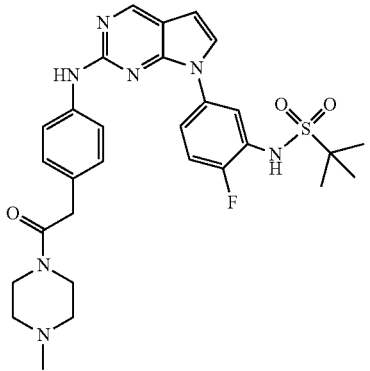 [SMILES: CN1CCN(C(=O)Cc2ccc(Nc3ncc4ccn(-c5ccc(F)c(NS(=O)(=O)C(C)(C)C)c5)c4n3)cc2)CC1] | 0.643 | 0.239 | | | | | | |
| 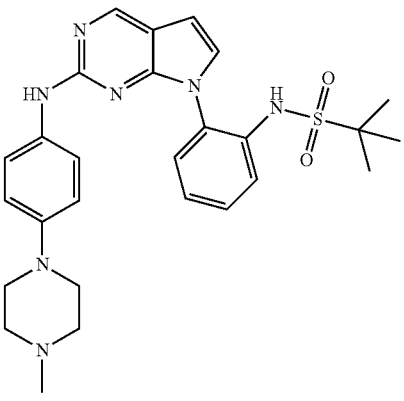 [SMILES: CN1CCN(c2ccc(Nc3ncc4ccn(-c5ccccc5NS(=O)(=O)C(C)(C)C)c4n3)cc2)CC1] | 10 | 2.4 | | | | | | |
| 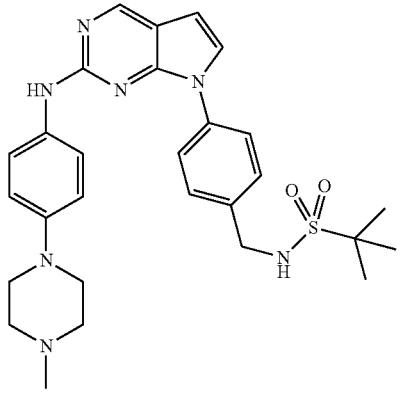 [SMILES: CN1CCN(c2ccc(Nc3ncc4ccn(-c5ccc(CNS(=O)(=O)C(C)(C)C)cc5)c4n3)cc2)CC1] | 10 | 0.00018 | | | | | | |
| 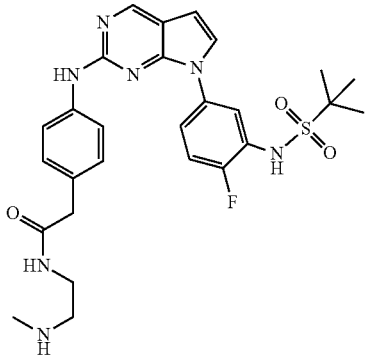 [SMILES: CNCCNC(=O)Cc1ccc(Nc2ncc3ccn(-c4ccc(F)c(NS(=O)(=O)C(C)(C)C)c4)c3n2)cc1] | 0.193 | 0.359 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 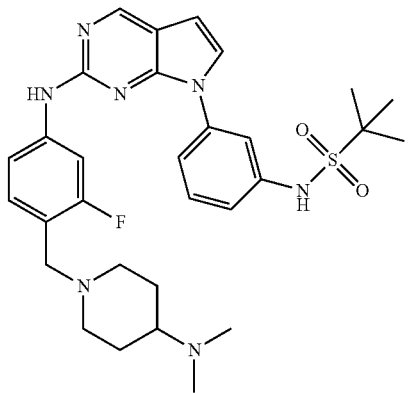 [SMILES: CN(C)C1CCN(Cc2ccc(Nc3ncc4ccn(-c5cccc(NS(=O)(=O)C(C)(C)C)c5)c4n3)cc2F)CC1] | 0.145 | 0.051 | | | | | | |
| 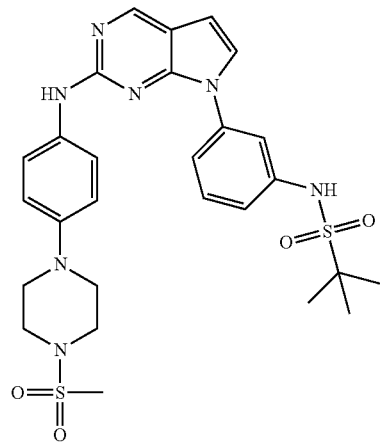 [SMILES: CC(C)(C)S(=O)(=O)Nc1cccc(-n2ccc3cnc(Nc4ccc(N5CCN(S(C)(=O)=O)CC5)cc4)nc32)c1] | 4.6 | 0.04 | | | | | | |
| 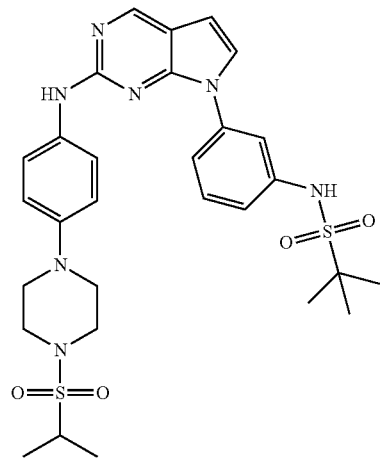 [SMILES: CC(C)S(=O)(=O)N1CCN(c2ccc(Nc3ncc4ccn(-c5cccc(NS(=O)(=O)C(C)(C)C)c5)c4n3)cc2)CC1] | 8.3 | 0.12 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 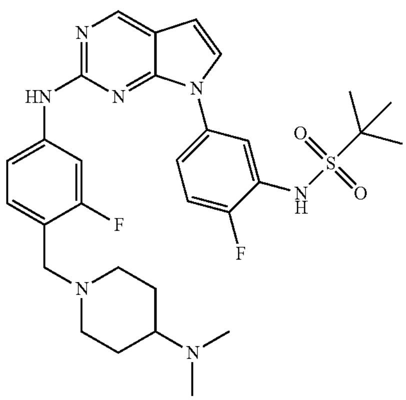 [SMILES: CN(C)C1CCN(Cc2ccc(Nc3ncc4ccn(-c5ccc(F)c(NS(=O)(=O)C(C)(C)C)c5)c4n3)cc2F)CC1] | 0.105 | 0.265 | | | | | | |
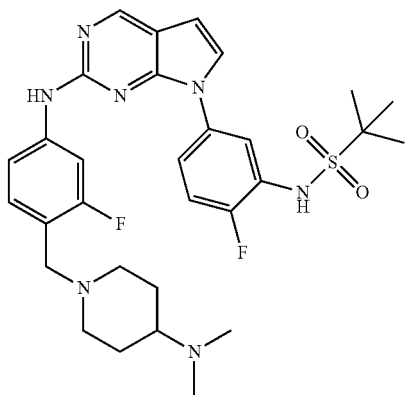
| | 0.138 | 0.01 | | | | | | |
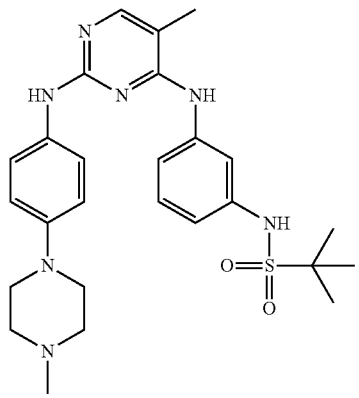
| | 0.131 | 0.003 | | | | | | |
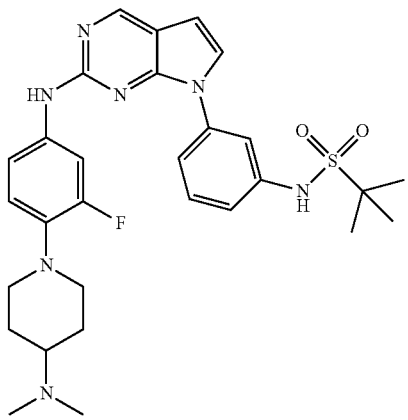 [SMILES: CN(C)C1CCN(c2ccc(Nc3ncc4ccn(-c5cccc(NS(=O)(=O)C(C)(C)C)c5)c4n3)cc2F)CC1]

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 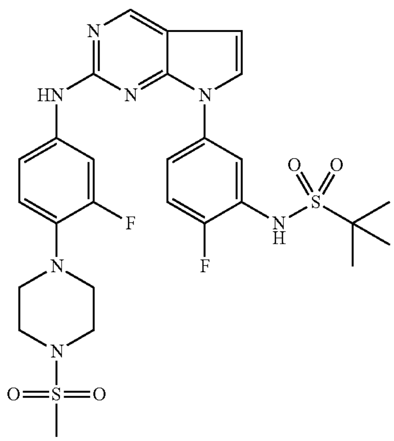 [SMILES: CC(C)(C)S(=O)(=O)Nc1cc(-n2ccc3cnc(Nc4ccc(N5CCN(S(C)(=O)=O)CC5)c(F)c4)nc32)ccc1F] | 1.4 | 0.4 | | | | | | |
| 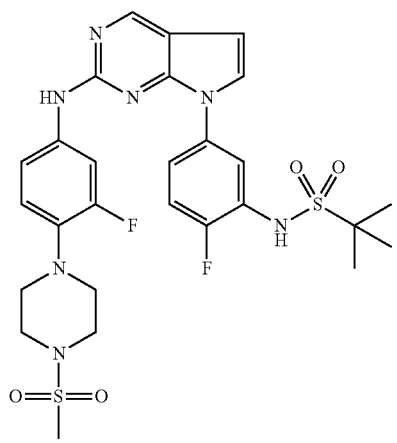 | 0.735 | 0.123 | | | | | | |
| 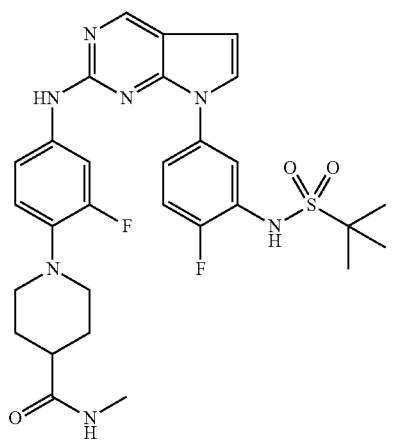 [SMILES: CNC(=O)C1CCN(c2ccc(Nc3ncc4ccn(-c5ccc(F)c(NS(=O)(=O)C(C)(C)C)c5)c4n3)cc2F)CC1] | 1.1 | 0.12 | | | | | | |
| 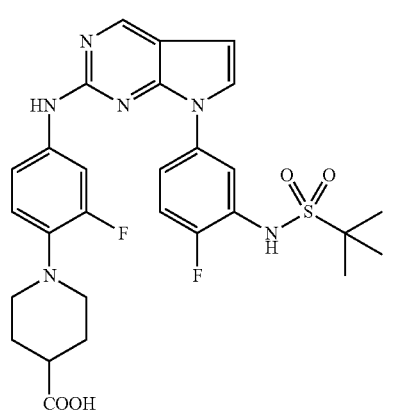 [SMILES: CC(C)(C)S(=O)(=O)Nc1cc(-n2ccc3cnc(Nc4ccc(N5CCC(C(=O)O)CC5)c(F)c4)nc32)ccc1F] | | | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 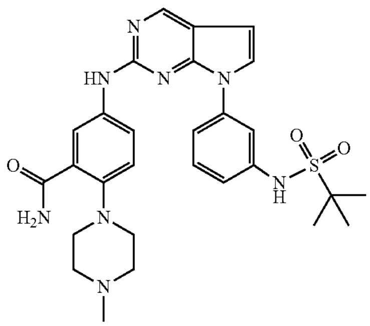 [SMILES: CN1CCN(c2ccc(Nc3ncc4ccn(-c5cccc(NS(=O)(=O)C(C)(C)C)c5)c4n3)cc2C(N)=O)CC1] | 0.577 | 0.072 | | | | | | |
| 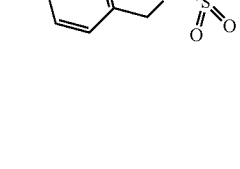 | 8.3 | 0.003 | | | | | | |
| 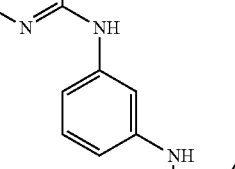 | 0.141 | 0.006 | | | | | | |
| 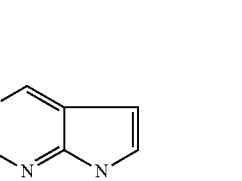 | 0.93 | 0.012 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *(structure)* | 10 | 10 | | | | | | |
| *(structure)* | 0.142 | 0.251 | | | | | | |
| *(structure)* | 0.295 | 0.142 | | | | | | |
| *(structure)* | 0.155 | 0.007 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 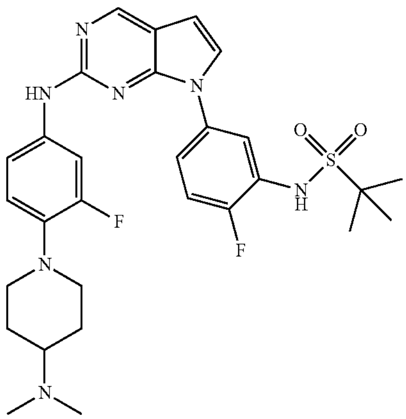 [SMILES: CN(C)C1CCN(c2ccc(Nc3ncc4ccn(-c5ccc(F)c(NS(=O)(=O)C(C)(C)C)c5)c4n3)cc2F)CC1] | 0.063 | 0.027 | | | | | | |
| 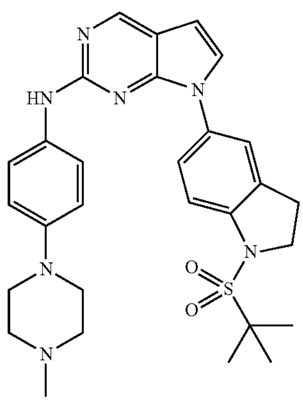 [SMILES: CN1CCN(c2ccc(Nc3ncc4ccn(-c5ccc6c(c5)CCN6S(=O)(=O)C(C)(C)C)c4n3)cc2)CC1] | 10 | 0.0006 | | | | | | |
| 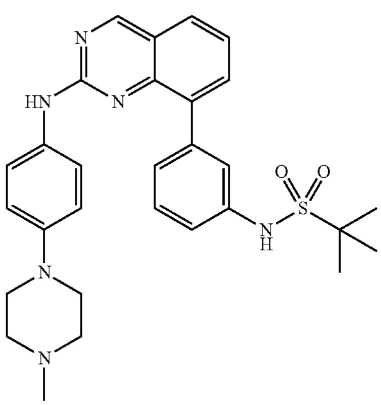 [SMILES: CN1CCN(c2ccc(Nc3ncc4cccc(-c5cccc(NS(=O)(=O)C(C)(C)C)c5)c4n3)cc2)CC1] | 3.8 | 0.01 | | | | | | |
| 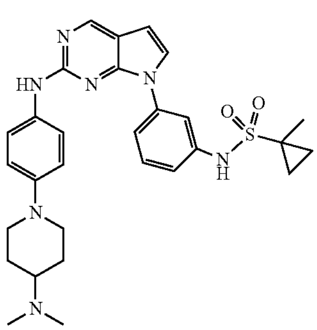 [SMILES: CN(C)C1CCN(c2ccc(Nc3ncc4ccn(-c5cccc(NS(=O)(=O)C6(C)CC6)c5)c4n3)cc2)CC1] | 0.636 | 0.006 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 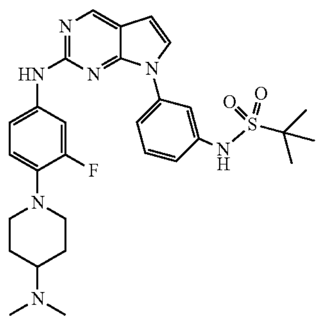 [SMILES: CN(C)C1CCN(c2ccc(Nc3ncc4ccn(-c5cccc(NS(=O)(=O)C(C)(C)C)c5)c4n3)cc2F)CC1] | 0.377 | 0.0044 | | | | | | |
| 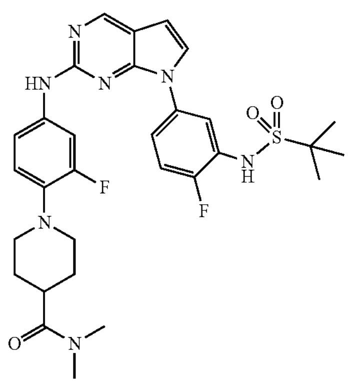 [SMILES: CN(C)C(=O)C1CCN(c2ccc(Nc3ncc4ccn(-c5ccc(F)c(NS(=O)(=O)C(C)(C)C)c5)c4n3)cc2F)CC1] | 0.491 | 0.129 | | | | | | |
| 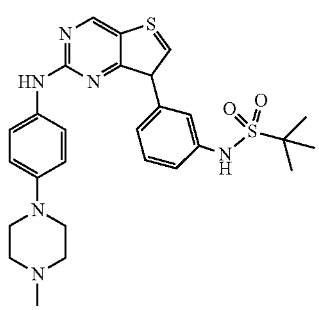 | 0.375 | 0.0048 | | | | | | |
| 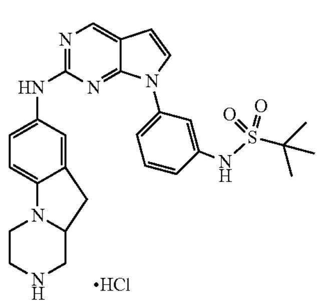 [SMILES: CC(C)(C)S(=O)(=O)Nc1cccc(-n2ccc3cnc(Nc4ccc5c(c4)CC4CNCCN54)nc32)c1 ; Cl] | 0.393 | 0.018 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure) | 0.208 | 0.014 | | | | | | |
| (structure) | 1.2 | 10 | | | | | | |
| (structure) | 0.315 | 10 | | | | | | |
| (structure) | 0.063 | 0.043 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 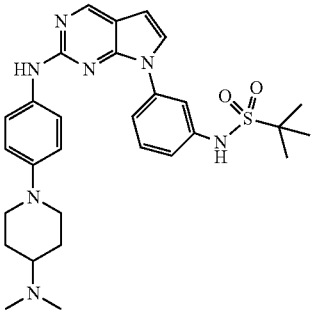 [SMILES: CN(C)C1CCN(c2ccc(Nc3ncc4ccn(-c5cccc(NS(=O)(=O)C(C)(C)C)c5)c4n3)cc2)CC1] | 0.229 | 0.0065 | | | | | | |
| 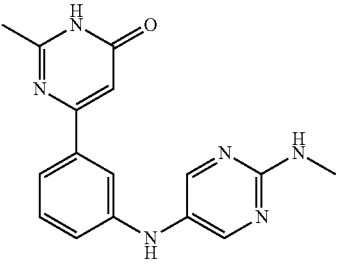 | NA | NA | | | | | | |
| 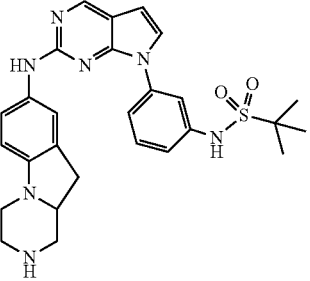 [SMILES: CC(C)(C)S(=O)(=O)Nc1cccc(-n2ccc3cnc(Nc4ccc5c(c4)CC4CNCCN54)nc32)c1] | 0.306 | 0.013 | | | | | | |
| 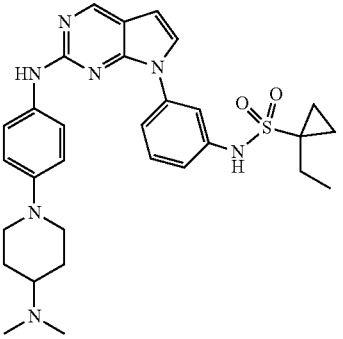 [SMILES: CCC1(S(=O)(=O)Nc2cccc(-n3ccc4cnc(Nc5ccc(N6CCC(N(C)C)CC6)cc5)nc43)c2)CC1] | 1.4 | 0.0047 | | | | | | |
| 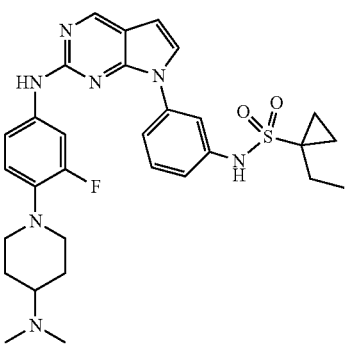 [SMILES: CCC1(S(=O)(=O)Nc2cccc(-n3ccc4cnc(Nc5ccc(N6CCC(N(C)C)CC6)c(F)c5)nc43)c2)CC1] | 1.5 | 0.005 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 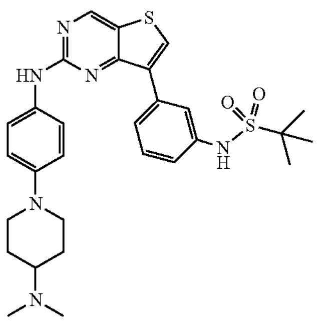 [SMILES: CN(C)C1CCN(c2ccc(Nc3ncc4scc(-c5cccc(NS(=O)(=O)C(C)(C)C)c5)c4n3)cc2)CC1] | 0.368 | 0.003 | | | | | | |
| 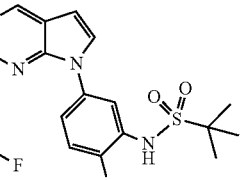 | 0.143 | 0.083 | | | | | | |
| 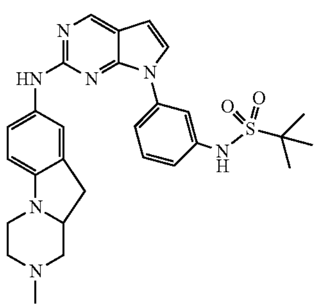 [SMILES: CN1CCN2c3ccc(Nc4ncc5ccn(-c6cccc(NS(=O)(=O)C(C)(C)C)c6)c5n4)cc3CC2C1] | 0.366 | 0.014 | | | | | | |
| 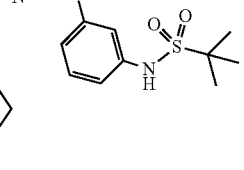 | 0.963 | 0.024 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 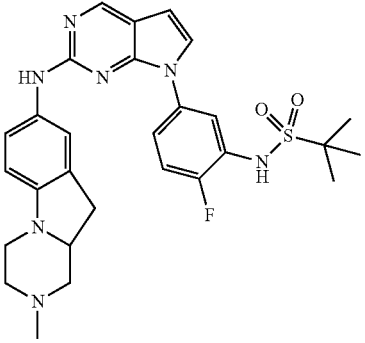 [SMILES: CN1CCN2c3ccc(Nc4ncc5ccn(-c6ccc(F)c(NS(=O)(=O)C(C)(C)C)c6)c5n4)cc3CC2C1] | 0.321 | 0.137 | | | | | | |
| 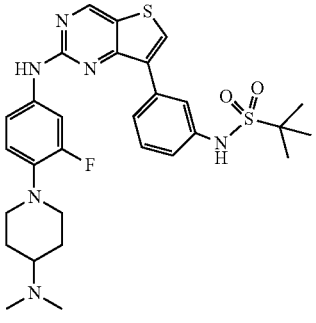 [SMILES: CN(C)C1CCN(c2ccc(Nc3ncc4scc(-c5cccc(NS(=O)(=O)C(C)(C)C)c5)c4n3)cc2F)CC1] | 0.297 | 0.004 | | | | | | |
| 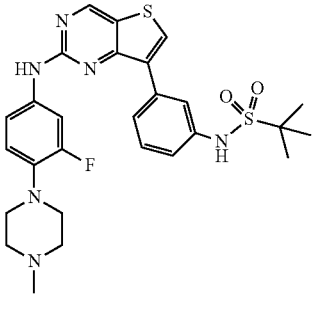 [SMILES: CN1CCN(c2ccc(Nc3ncc4scc(-c5cccc(NS(=O)(=O)C(C)(C)C)c5)c4n3)cc2F)CC1] | 0.393 | 0.018 | | | | | | |
| 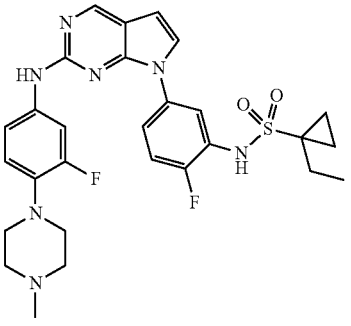 [SMILES: CCC1(S(=O)(=O)Nc2cc(-n3ccc4cnc(Nc5ccc(N6CCN(C)CC6)c(F)c5)nc43)ccc2F)CC1] | 1.5 | 0.103 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 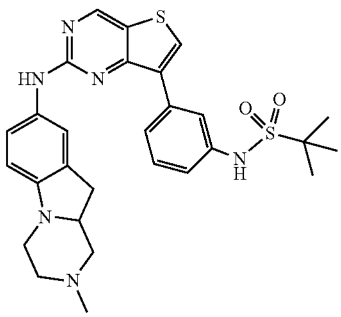 [SMILES: CN1CCN2c3ccc(Nc4ncc5scc(-c6cccc(NS(=O)(=O)C(C)(C)C)c6)c5n4)cc3CC2C1] | 0.607 | 0.002 | | | | | | |
| 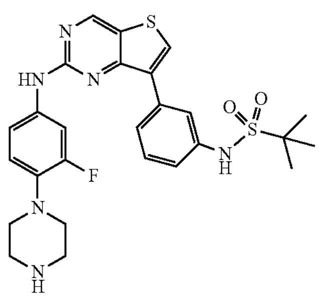 [SMILES: CC(C)(C)S(=O)(=O)Nc1cccc(-c2csc3cnc(Nc4ccc(N5CCNCC5)c(F)c4)nc23)c1] | 0.295 | 0.002 | 0.193 | 0.506 | 0.181 | 0.308 | 0.169 | 0.061 |
| 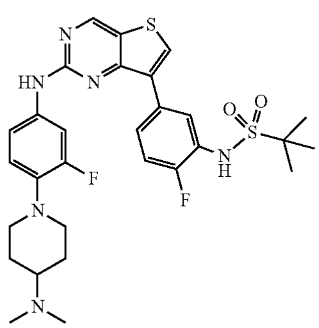 [SMILES: CN(C)C1CCN(c2ccc(Nc3ncc4scc(-c5ccc(F)c(NS(=O)(=O)C(C)(C)C)c5)c4n3)cc2F)CC1] | 0.108 | 0.008 | 0.091 | 0.292 | 0.11 | 0.177 | 0.927 | 0.097 |
| 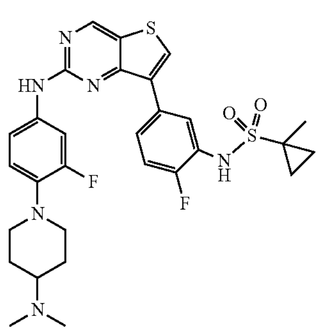 [SMILES: CN(C)C1CCN(c2ccc(Nc3ncc4scc(-c5ccc(F)c(NS(=O)(=O)C6(C)CC6)c5)c4n3)cc2F)CC1] | 0.233 | 0.011 | 0.203 | 0.605 | 0.196 | 0.329 | 0.734 | 0.06 |
| 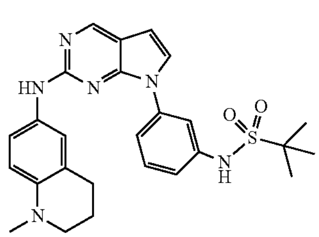 [SMILES: CN1CCCc2cc(Nc3ncc4ccn(-c5cccc(NS(=O)(=O)C(C)(C)C)c5)c4n3)ccc21] | 0.8 | 0.07 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure) | 0.248 | 0.02 | | | | | | |
| (structure) | 0.06 | 0.033 | 0.064 | 0.216 | 0.059 | 0.118 | 2.1 | 0.272 |
| (structure) | 0.228 | 0.036 | | | | | | |
| (structure) | 0.125 | 0.076 | | | | | | |
| (structure) | 0.248 | 0.0096 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure) | 0.174 | 0.008 | | | | | | |
| (structure) | 3.2 | 0.035 | | | | | | |
| (structure) | 0.318 | 0.005 | | | | | | |
| (structure) | 0.162 | 0.051 | | | | | | |
| (structure) | 0.3 | 0.006 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 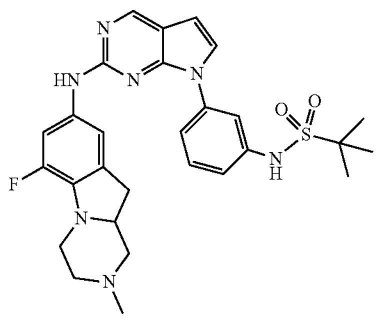 [SMILES: CN1CCN2c3c(F)cc(Nc4ncc5ccn(-c6cccc(NS(=O)(=O)C(C)(C)C)c6)c5n4)cc3CC2C1] | 0.571 | 0.014 |  |  |  |  |  |  |
| 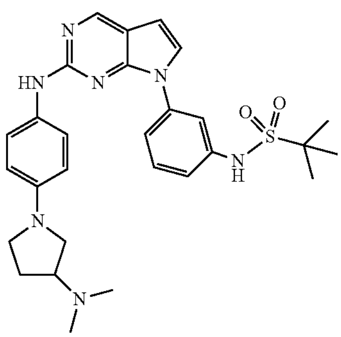 [SMILES: CN(C)C1CCN(c2ccc(Nc3ncc4ccn(-c5cccc(NS(=O)(=O)C(C)(C)C)c5)c4n3)cc2)C1] | 0.854 | 0.037 |  |  |  |  |  |  |
| 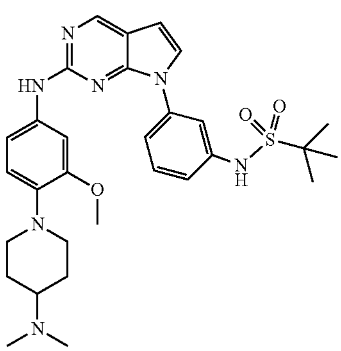 [SMILES: COc1cc(Nc2ncc3ccn(-c4cccc(NS(=O)(=O)C(C)(C)C)c4)c3n2)ccc1N1CCC(N(C)C)CC1] | 0.421 | 0.002 |  |  |  |  |  |  |
| 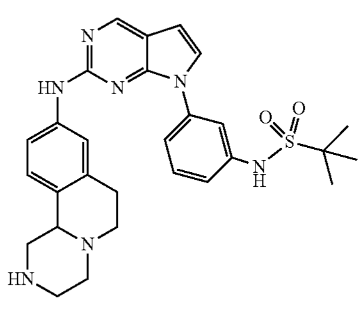 [SMILES: CC(C)(C)S(=O)(=O)Nc1cccc(-n2ccc3cnc(Nc4ccc5c(c4)CCN4CCNCC54)nc32)c1] | 0.75 | 0.037 |  |  |  |  |  |  |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 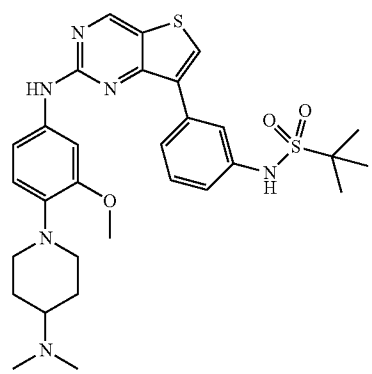 [SMILES: COc1cc(Nc2ncc3scc(-c4cccc(NS(=O)(=O)C(C)(C)C)c4)c3n2)ccc1N1CCC(N(C)C)CC1] | 0.56 | 0.001 | | | | | | |
| 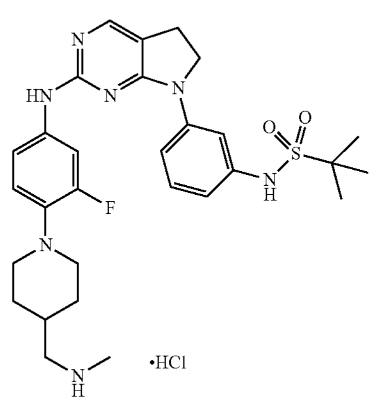 [SMILES: CNCC1CCN(c2ccc(Nc3ncc4c(n3)N(c3cccc(NS(=O)(=O)C(C)(C)C)c3)CC4)cc2F)CC1 ; Cl] | 0.58 | 0.009 | | | | | | |
| 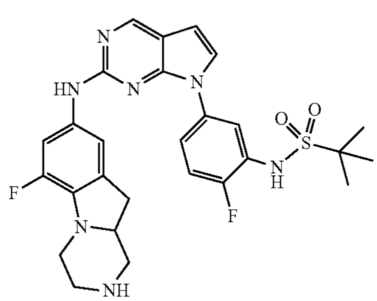 [SMILES: CC(C)(C)S(=O)(=O)Nc1cc(-n2ccc3cnc(Nc4cc(F)c5c(c4)CC4CNCCN54)nc32)ccc1F] | 0.079 | 0.04 | 0.085 | 0.235 | 0.081 | 0.185 | 3.7 | 0.206 |
| 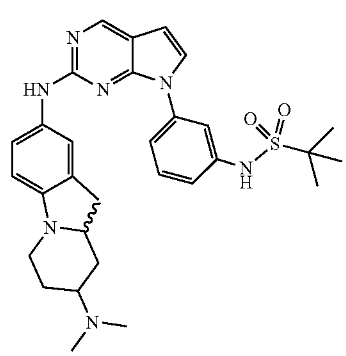 [SMILES: CN(C)C1CCN2c3ccc(Nc4ncc5ccn(-c6cccc(NS(=O)(=O)C(C)(C)C)c6)c5n4)cc3CC2C1] | 0.268 | 0.008 | | | | | | |

TABLE 6-continued

| Structure | BRD4(1) IC50 (µM) | JAK2 IC50 (µM) | BRD4(2) IC50 (µM) | BRD2(1) IC50 (µM) | BRD3(1) IC50 (µM) | BRDT(1) IC50 (µM) | JAK1 IC50 (µM) | JAK3 IC50 (µM) |
|---|---|---|---|---|---|---|---|---|
| [structure] | 0.105 | 0.012 | | | | | | |
| [structure] | 0.356 | 0.004 | | | | | | |
| [structure] | 0.357 | 0.006 | | | | | | |
| [structure] | 0.337 | 0.022 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| (structure) | 0.431 | 0.002 | | | | | | |
| (structure) | 0.234 | 0.029 | | | | | | |
| (structure) | 0.298 | 0.012 | | | | | | |
| (structure) | 1.8 | 0.007 | | | | | | |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 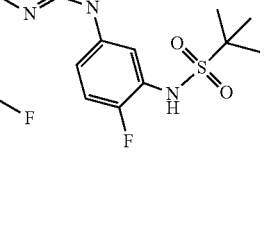 | 0.383 | 0.056 | | | | | | |
| 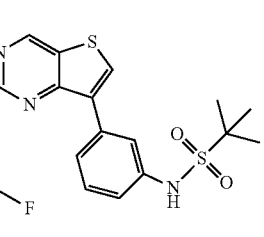 | 0.766 | 0.005 | | | | | | |
| 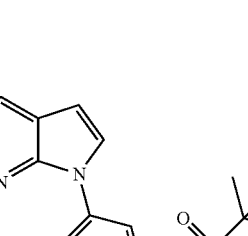 | 0.538 | 0.017 | | | | | | |
| 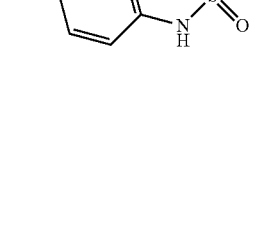 | 0.123 | 0.039 | 0.086 | 0.36 | 0.097 | 0.185 | 1.5 | 0.173 |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 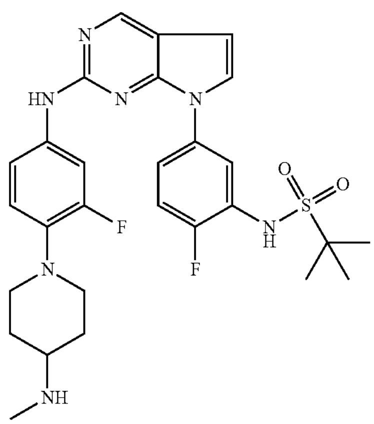 [SMILES: CNC1CCN(c2ccc(Nc3ncc4ccn(-c5ccc(F)c(NS(=O)(=O)C(C)(C)C)c5)c4n3)cc2F)CC1] | 0.15 | 0.052 | 0.088 | 0.42 | | 0.302 | 9.9 | 0.608 |
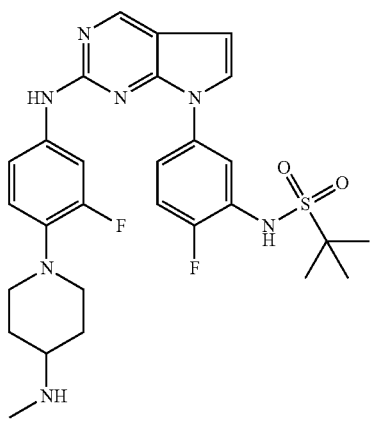
| | 0.192 | 0.01 | 0.092 | 0.67 | 0.154 | 0.223 | 1.2 | 0.082 |
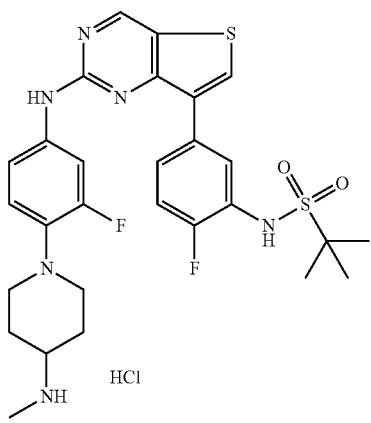 [SMILES: CNC1CCN(c2ccc(Nc3ncc4scc(-c5ccc(F)c(NS(=O)(=O)C(C)(C)C)c5)c4n3)cc2F)CC1 ; Cl]
| | 0.308 | 0.021 | | | | | | |
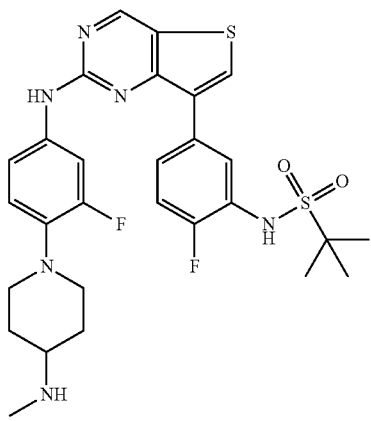 [SMILES: CNC1CCN(c2ccc(Nc3ncc4scc(-c5ccc(F)c(NS(=O)(=O)C(C)(C)C)c5)c4n3)cc2F)CC1]

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| *[structure]* | 2.3 | 0.05 | | | | | | |
| *[structure]* | 0.22 | 0.007 | | | | | | |
| *[structure]* | 0.125 | 0.052 | 0.054 | 0.473 | 0.158 | 0.268 | 0.992 | 0.403 |
| *[structure]* | 0.082 | 0.028 | 0.054 | 0.369 | 0.123 | 0.194 | 0.587 | 0.334 |

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| 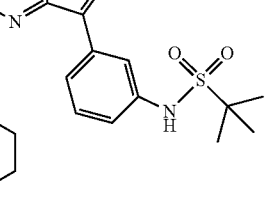 | 0.109 | 0.002 | 0.131 | 0.489 | 0.1 | 0.281 | 0.044 | 0.018 |
| 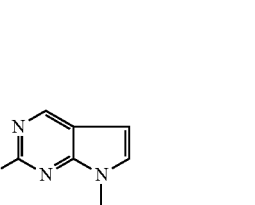 | 0.115 | 0.061 | 0.12 | 0.353 | 0.083 | 0.292 | 10 | 0.285 |
| 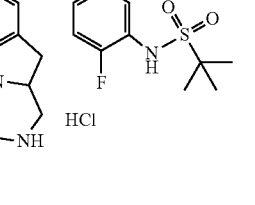 | 0.2 | 0.027 | | | | | | |
| 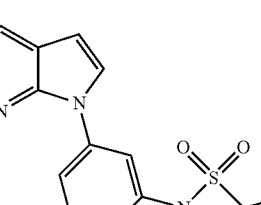 | 1.3 | 0.079 | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| | | | | | | | | |
| | | | | | | | | |
| | | | | | | | | |
| | | | | | | | | |

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
| | | | | | | | | |
| | | | | | | | | |
| | | | | | | | | |
| | | | | | | | | |

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|

TABLE 6-continued
| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|
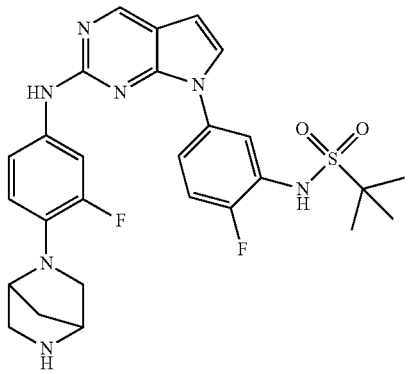 [SMILES: CC(C)(C)S(=O)(=O)Nc1cc(-n2ccc3cnc(Nc4ccc(N5CC6CC5CN6)c(F)c4)nc32)ccc1F]
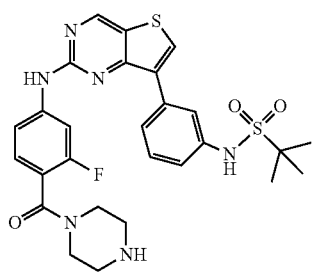 [SMILES: CC(C)(C)S(=O)(=O)Nc1cccc(-c2csc3cnc(Nc4ccc(C(=O)N5CCNCC5)c(F)c4)nc23)c1]
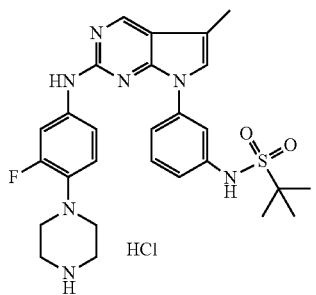 [SMILES: Cc1cn(-c2cccc(NS(=O)(=O)C(C)(C)C)c2)c2nc(Nc3ccc(N4CCNCC4)c(F)c3)ncc12 ; Cl]
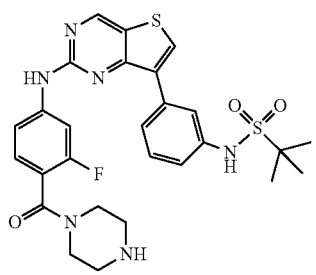 [SMILES: CC(C)(C)S(=O)(=O)Nc1cccc(-c2csc3cnc(Nc4ccc(C(=O)N5CCNCC5)c(F)c4)nc23)c1]

TABLE 6-continued

| Structure | BRD4(1) IC50 (μM) | JAK2 IC50 (μM) | BRD4(2) IC50 (μM) | BRD2(1) IC50 (μM) | BRD3(1) IC50 (μM) | BRDT(1) IC50 (μM) | JAK1 IC50 (μM) | JAK3 IC50 (μM) |
|---|---|---|---|---|---|---|---|---|

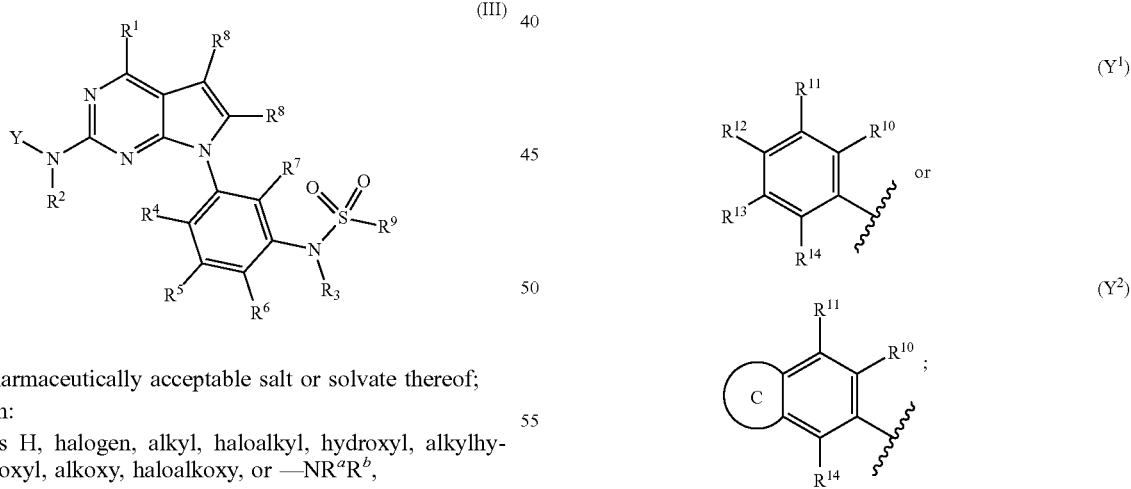

What is claimed is:

1. A compound of formula (III):

or a pharmaceutically acceptable salt or solvate thereof; wherein:

$R^1$ is H, halogen, alkyl, haloalkyl, hydroxyl, alkylhydroxyl, alkoxy, haloalkoxy, or —NR$^a$R$^b$, $R^2$ and $R^3$ are each independently H or alkyl;

$R^4$ and $R^5$ are each independently H, halogen, hydroxyl or alkyl;

$R^6$ and $R^7$ are each independently H, halogen, hydroxyl or alkyl; or alternatively, $R^6$ and $R^3$ together or $R^7$ and $R^3$ together forms a saturated, unsaturated, or partially saturated, 5- or 6-membered ring;

$R^6$ is H, halogen, or alkyl;

$R^9$ is alkyl, cycloalkyl, or aryl, wherein cycloalkyl and aryl is optionally substituted with one or more of halogen or alkyl;

Y is selected from in $Y^1$ and $Y^2$, $R^{19}$ and $R^{14}$ are each independently H, halogen, hydroxyl, alkyl, or alkoxy;

in $Y^1$, $R^{11}$, $R^{12}$ and $R^{13}$ are each independently H, halogen, alkyl, alkoxy, heterocyclyl, —(CH$_2$)n-C(O)NR$^a$R$^c$, —(CH$_2$)n-NR$^a$C(O)R$^d$, —(CH$_2$)n-C(O)(CH$_2$)n-, —NR$^a$R$^b$, —NR$^a$-alkylene-NR$^a$R$^b$, or —(CH$_2$)n-C(O)NR$^a$-alkylene-NR$^a$R$^b$; or in $Y^2$, $R^{11}$ is H, halogen, hydroxyl or alkyl; in $Y^2$, ring C is a monocyclic, bicyclic, or tricyclic 5- to 12-membered heterocycle containing at least one atom selected from N, O, or S, wherein ring C is optionally substituted with $R^{15}$;

$R^a$ and $R^b$ are each independently, H or alkyl;

$R^c$ is H, alkyl, -alkyl-$NR^aR^b$, or heterocyclyl;

$R^d$ is alkyl, -alkyl-$NR^aR^b$, or heterocyclyl;

wherein heterocycyl in $R^{11}$, $R^{12}$, $R^{13}$, $R^c$, and $R^d$ is each independently optionally substituted with $R^{15}$;

$R^{15}$ is halogen, hydroxyl, alkyl, alkylhydroxyl, oxo, —C(O)-alkyl, —C(O)$OR^a$; —$NR^aC(O)$alkyl, —$(CH_2)_n$—C(O)$NR^aR^b$, $NR^aR^b$; or —$S(O)_n$-alkyl, and n is 0, 1, or 2 wherein, at least one of $R^{11}$ and $R^{13}$ is a halogen.

2. The compound of claim 1, wherein $R^2$ and $R^3$ are each H or $C_1$-$C_3$ alkyl.

3. The compound of claim 1, wherein $R^4$ and $R^5$ are each H.

4. The compound of claim 1, wherein $R^6$ and $R^7$ are each independently H or halogen.

5. The compound of claim 1, wherein $R^6$ and $R^3$ together forms a saturated, unsaturated, or partially saturated, 5- or 6-membered ring.

6. The compound of claim 5, wherein, $R^6$ and $R^3$ together forms a saturated 5-membered ring.

7. The compound of claim 1, wherein, $R^{10}$ and $R^4$ are each H.

8. The compound of claim 1, wherein Y is $Y^1$.

9. The compound of claim 8, wherein one of $R^{11}$, $R^{12}$ and $R^{13}$ is an optionally substituted heterocyclyl.

10. The compound of claim 9, wherein the heterocyclyl is selected from piperidine, piperazine, hexahydropyrimidine, morpholine, tetrahydropyran, thiane, or thiomorpholine, each optionally substituted.

* * * * *